(12) United States Patent
Minko et al.

(10) Patent No.: US 9,289,505 B2
(45) Date of Patent: Mar. 22, 2016

(54) COMPOSITIONS AND METHODS FOR DELIVERING NUCLEIC ACID MOLECULES AND TREATING CANCER

(75) Inventors: Tamara Minko, Somerset, NJ (US); Lorna Rodriguez-Rodriguez, East Brunswick, NJ (US); Olga B. Garbuzenko, Highland Park, NJ (US); Oleh Taratula, West Windsor, NJ (US); Vatsal Shah, New Bruswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 13/817,054

(22) PCT Filed: Aug. 17, 2011

(86) PCT No.: PCT/US2011/048078
§ 371 (c)(1),
(2), (4) Date: Jul. 10, 2013

(87) PCT Pub. No.: WO2012/024396
PCT Pub. Date: Feb. 23, 2012

(65) Prior Publication Data
US 2013/0302257 A1 Nov. 14, 2013

Related U.S. Application Data

(60) Provisional application No. 61/374,413, filed on Aug. 17, 2010.

(51) Int. Cl.
*A61K 47/48* (2006.01)
*C12N 15/87* (2006.01)

(52) U.S. Cl.
CPC ..... *A61K 47/48192* (2013.01); *A61K 47/48215* (2013.01); *A61K 47/48246* (2013.01); *A61K 47/48346* (2013.01); *C12N 15/87* (2013.01); *C12N 2810/854* (2013.01)

(58) Field of Classification Search
None
See application file for complete search history.

(56) References Cited

U.S. PATENT DOCUMENTS

| 7,642,048 | B2 * | 1/2010 | Gabrin et al. ........... 435/4 |
| 2008/0112916 | A1 | 5/2008 | Wagner et al. |
| 2008/0193384 | A1 | 8/2008 | Willard et al. |
| 2008/0280813 | A1 | 11/2008 | Minko et al. |

FOREIGN PATENT DOCUMENTS

| WO | 2007/006700 | 1/2007 |
| WO | 2007006700 | 1/2007 |

OTHER PUBLICATIONS

Qi, et al. (May 29, 2009 Epub) "PEG-conjugated PAMAM dendrimers mediate efficient intramuscular gene expression", American Association of Pharmaceutical Scientists Journal, 11(3): 395-405.*
Yoo, et al. (1999) "PAMAM dendrimers as delivery agents for antisense oligonucleotides", Pharmaceutical Research, 16(2): 1799-804 (Abstract Only).*
Choi, et al. (2004) "Enhanced transfection efficiency of PAMAM dendrimer by surface modification with L-arginine", Journal of Controlled Release, 99(3): 445-56.*
Dong, et al. (Apr. 21, 2009) "Doxorubicin and Paclitaxel-Loaded Lipid-Based Nanoparticles Overcome Multidrug Resistance by Inhibiting P-Glycoprotein and Depleting ATP", Cancer Research, 69(9): 3918-26.*
Szakacs, et al. (2006) "Targeting Multidrug Resistance in Cancer", Nature Reviews: Drug Discovery, 5(3): 219-34.*
Kim, et al. (May 15, 2009) "siRNA-based targeting of antiapoptotic genes can reverse chemoresistance in P-glycoprotein expressing chondrosarcoma cells", Molecular Cancer, 8, Article 28: pp. 1-10.*
Beh, et al. (2009, online Dec. 15, 2008) "Efficient Delivery of Bcl-2-Targeted siRNA Using Cationic Polymer Nanoparticles: Downregulating mRNA Expression Level and Sensitizing Cancer Cells to Anticancer Drug", Biomacromolecules, 10(1): 41-48.*
Chisholm, et aol. (Mar. 3, 2009 online) "Cancer-Specific Transgene Expression Mediated by Systemic Injection of Nanoparticles", Cancer Research: 69(6): 2655-62.*
Chanda, et al. (2007) "Targeted Proapoptotic Anticancer Drug Delivery System", Molecular Pharmaceutics, 4(5): 668-78.*
Garbuzenko et al. Intratracheal versus intravenous liposomal delivery of siRNA, antisense oligonucleotides and anticancer drug. Pharm Res. 2009, 382-94, 26(2).
Chandna et al. Multifunctional tumor-targeted polymer-peptide-drug delivery system for treatment of primary and metastatic cancers. Pharm Res. 2010, 2296-306, 27(11).
Saad et al. Co-delivery of siRNA and an anticancer drug for treatment of multidrug-resistant cancer. Nanomedicine (Lond). 2008, 761-76, 3(6).
Betigeri et al. Non-viral systemic delivery of siRNA or antisense oligonucleotides targeted to Jun N-terminal kinase 1 prevents cellular hypoxic damage. Drug Deliv Trans! Res. 2011, 13-24, 1(1).
Chen et al. Co-delivery of doxorubicin and Bcl-2 siRNA by mesoporous silica nanoparticles enhances the efficacy of chemotherapy in multidrug-resistant cancer cells. Small. 2009, 2673-7, 5(23).
Garbuzenko et al. Inhibition of lung tumor growth by complex pulmonary delivery of drugs with oligonucleotides as suppressors of cellular resistance. Proc Natl Acad Sci U S A. 2010, 10737-42, 107(23).
Patil et al. Multifunctional triblock Nanocarrier (PAMAM-PEG-PLL) for the efficient intracellular siRNA delivery and gene silencing. ACS Nano. 2011, 1877-87, 5(3).

(Continued)

*Primary Examiner* — Robert M Kelly
(74) *Attorney, Agent, or Firm* — Robert C. Netter, Jr.; Dann, Dorfman, Herrell & Skillman

(57) ABSTRACT

The present invention provides compositions and methods for the delivery of nucleic acids to a cell. The present invention additionally provides compositions and methods for the treatment of a disease or disorder, particularly cancer. In a particular embodiment, the composition comprises at least one pharmaceutically acceptable carrier and at least one liposome or dendrimer comprising at least two chemotherapeutic agents with different mechanisms of action and at least two inhibitors of cellular drug resistance.

4 Claims, 38 Drawing Sheets

(56) References Cited

OTHER PUBLICATIONS

Figure 1D:
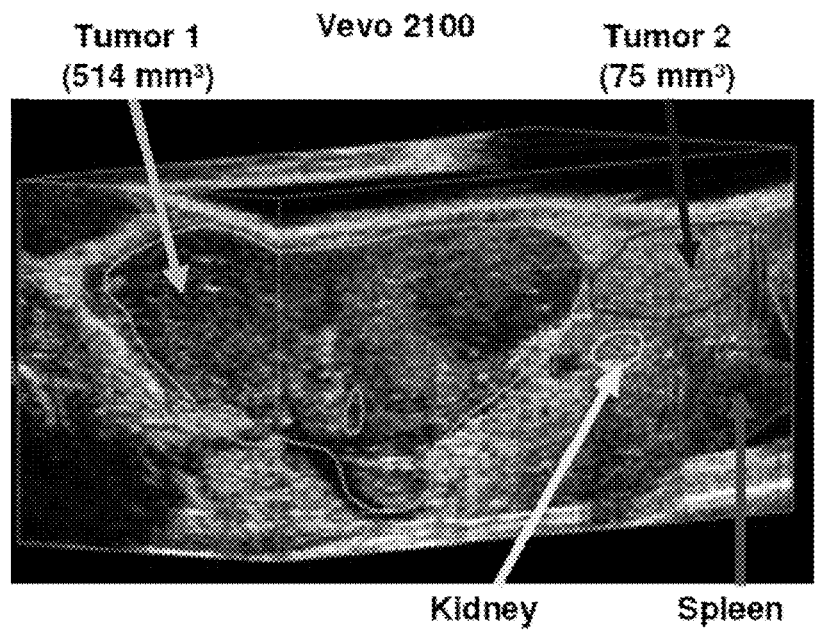

Taratula et al. Multifunctional nanomedicine platform for cancer specific delivery of siRNA by superparamagnetic iron oxide nanoparticles-dendrimer complexes. Curr Drug Deliv. 2011, 59-69, 8(1).

Taratula et al. Surface-Engineered Targeted PPI Dendrimer for Efficient Intracellular and Intratumoral siRNA Delivery. J Control Release. 2009, 284-93, 140(3).

* cited by examiner

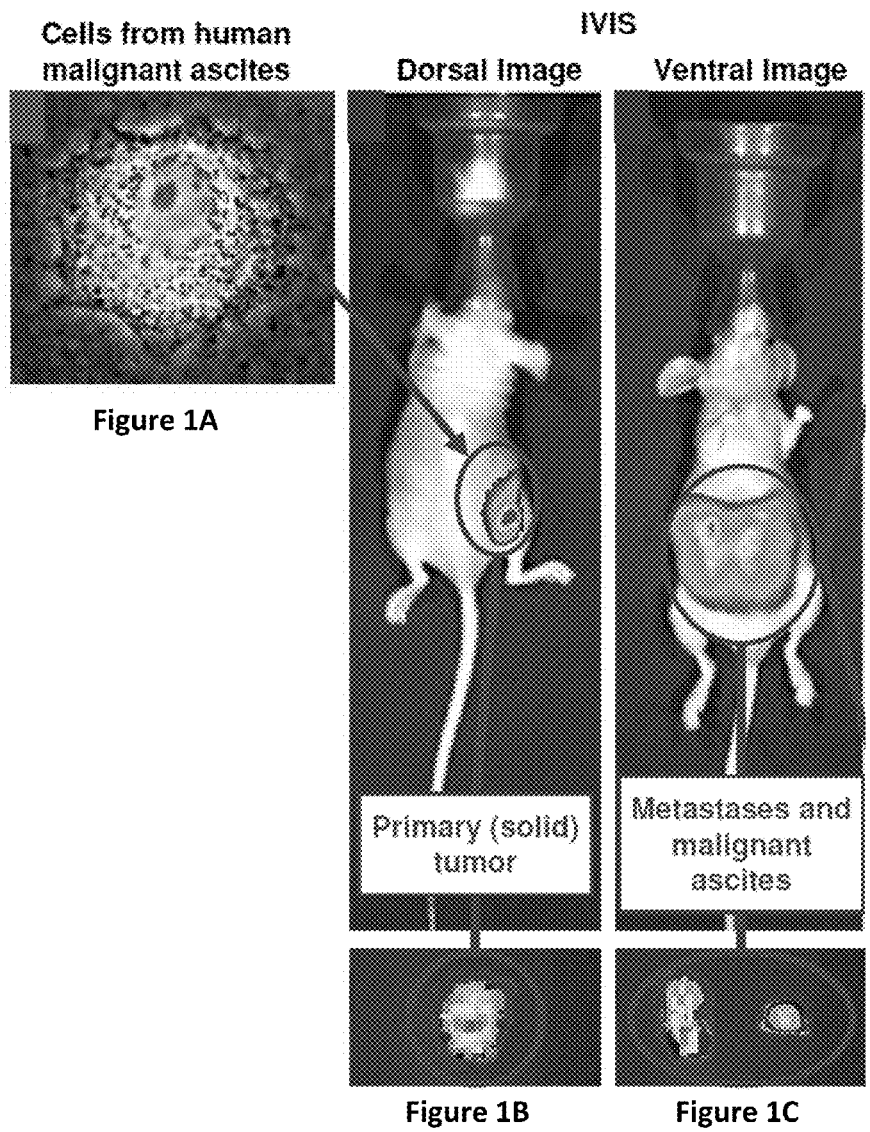

Figure 4A P-glycoprotein
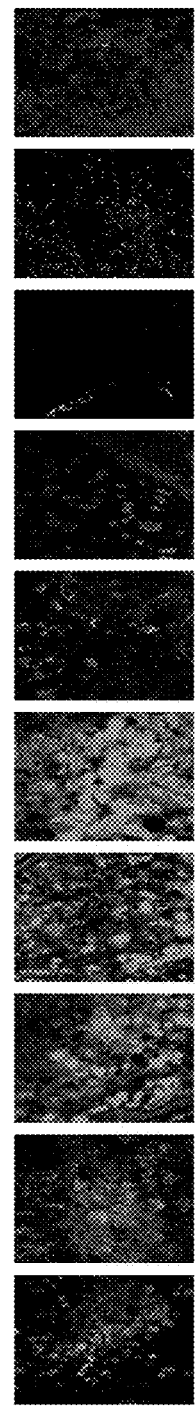
Figure 4B BCL2
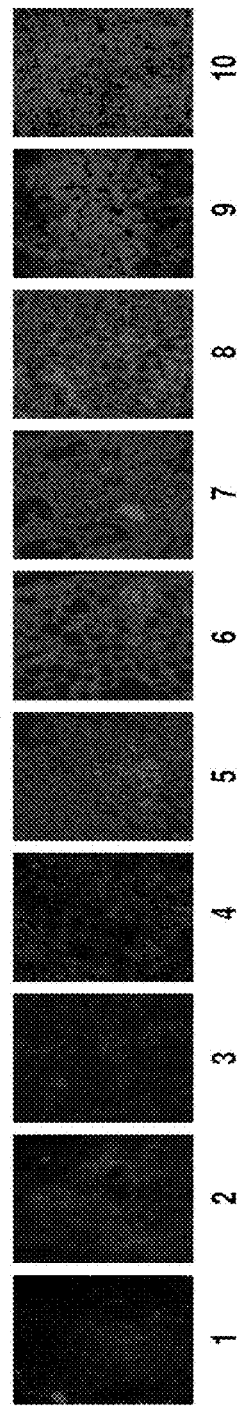
Figure 4C Caspase 3

Figure 17A
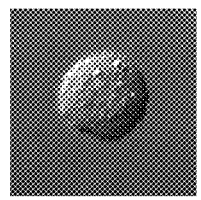
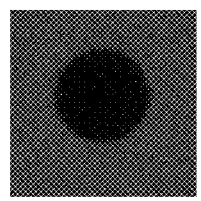
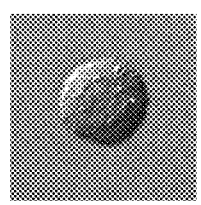
LIGHT
FLUORESCENCE
LIGHT + FLUORESCENCE
Figure 17B
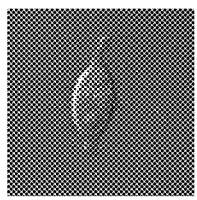
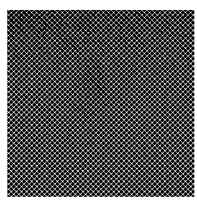
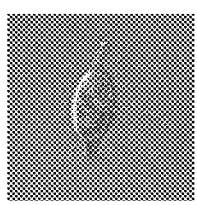
TOP →
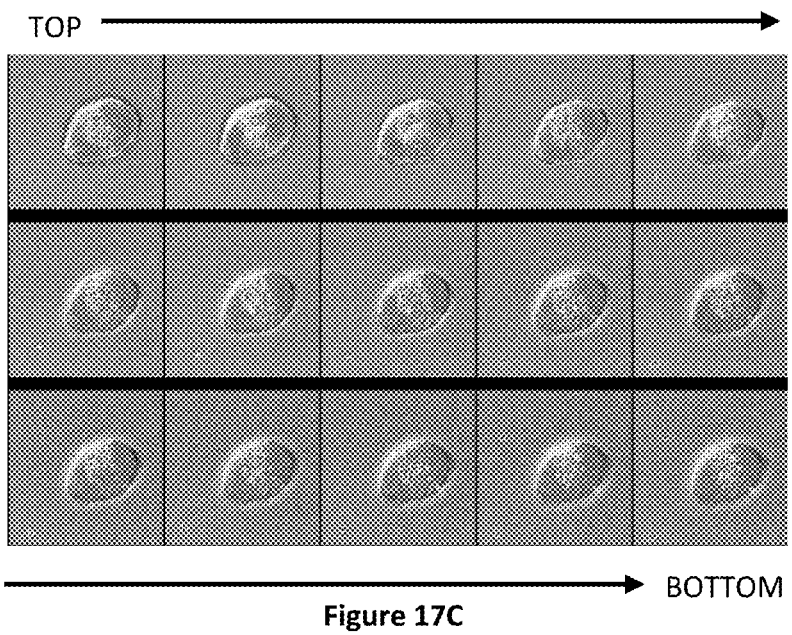
→ BOTTOM
Figure 17C

A. Cooperative condensation of siRNA with 5nm SPIO and PPI G5
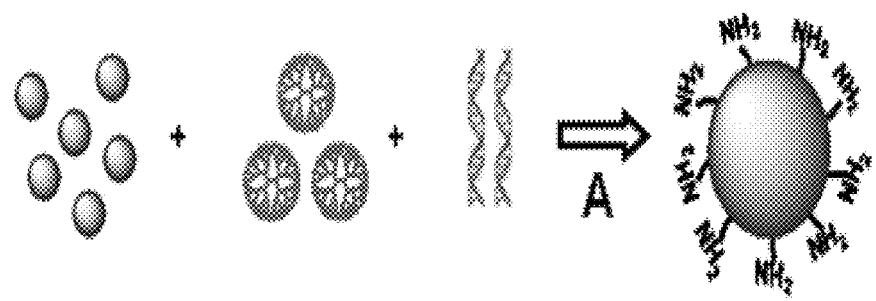
| 5 nm SPIO nanoparticles | PPI G5 dendrimers | siRNA | SPIO-PPI G5-siRNA complexes |
B. PEGylation
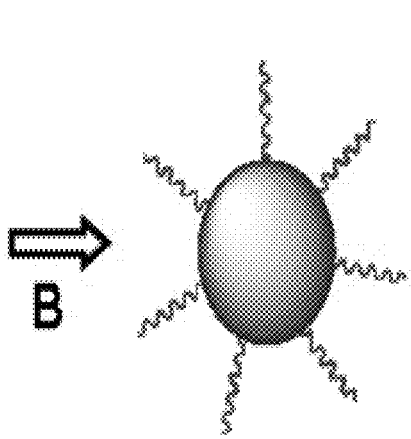
C. Targeting by LHRH peptide
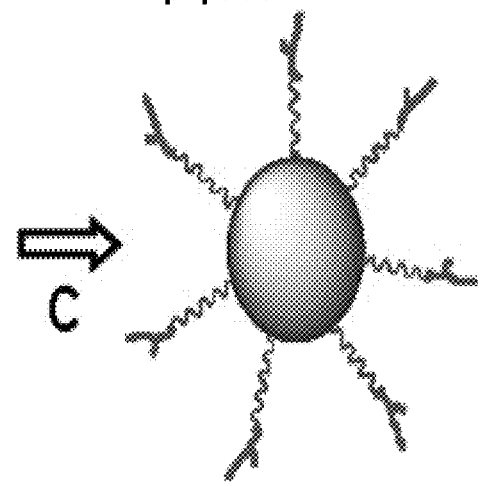
∿∿∿ PEG-MAL   Figure 24   Y LHRH Figure 27A
Figure 27B
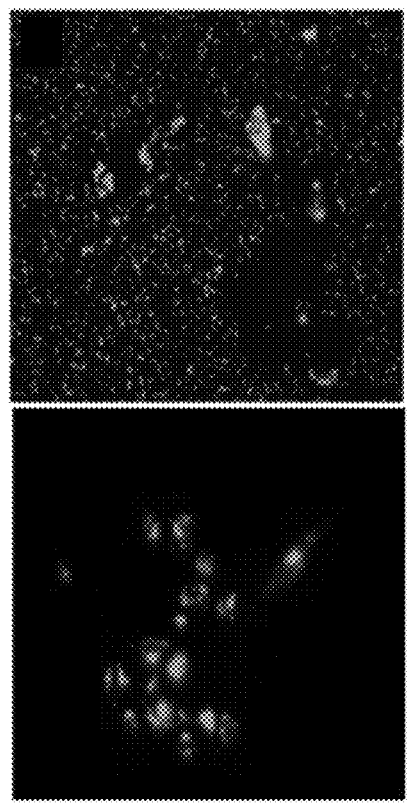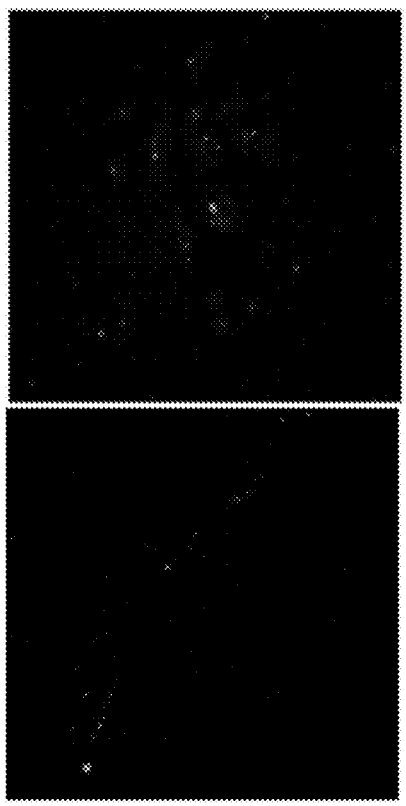
Figure 27C
Figure 27D

SEQUENCE LISTING

```
<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Synthetic sequence

<400> SEQUENCE: 1
ttcaagatcc atcccgacct cgcg                                          24

<210> SEQ ID NO 2
<211> LENGTH: 20
<212> TYPE: DNA
<213> ORGANISM: Artificial Sequence
<220> FEATURE:
<223> OTHER INFORMATION: Synthetic sequence

<400> SEQUENCE: 2
cagcgtgcgc catccttccc                                               20

<210> SEQ ID NO 3
<211> LENGTH: 9
<212> TYPE: PRT
<213> ORGANISM: Artificial Sequence
<220> FEATURE:
<223> OTHER INFORMATION: Synthetic sequence
<220> FEATURE:
<221> NAME/KEY: SITE
<222> LOCATION: 6
<223> OTHER INFORMATION: D-amino acid

<400> SEQUENCE: 3

Gln His Trp Ser Tyr Lys Leu Arg Pro
1               5

<210> SEQ ID NO 4
<211> LENGTH: 21
<212> TYPE: DNA
<213> ORGANISM: Artificial Sequence
<220> FEATURE:
<223> OTHER INFORMATION: Synthetic sequence

<400> SEQUENCE: 4
gugaagucaa caugccugct t                                             21

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence

<400> SEQUENCE: 5
gcaggcaugu ugacuucact t                                             21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ggattgtggc cttctttgag                                               20
```

```
<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ccaaactgag cagagtcttc                                                  20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
acccccactg aaaaagatga                                                  20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
atcttcaaac ctccatgatg                                                  20

<210> SEQ ID NO 10
<211> LENGTH: 21
<212> TYPE: DNA
<213> ORGANISM: Artificial Sequence
<220> FEATURE:
<223> OTHER INFORMATION: Synthetic sequence

<400> SEQUENCE: 10
ccucgggcug ugcucuuuut t                                                21

<210> SEQ ID NO 11
<211> LENGTH: 21
<212> TYPE: DNA
<213> ORGANISM: Artificial Sequence
<220> FEATURE:
<223> OTHER INFORMATION: Synthetic sequence

<400> SEQUENCE: 11
aaaagagcac agcccgaggt t                                                21
```

COMPOSITIONS AND METHODS FOR DELIVERING NUCLEIC ACID MOLECULES AND TREATING CANCER This application is §371 application of PCT/US2011/048078, filed Aug. 17, 2011, which claims priority under 35 U.S.C. §119(e) to U.S. Provisional Patent Application No. 61/374,413, filed Aug. 17, 2010. The entire disclosure of each of the foregoing applications is incorporated by reference herein.

Incorporated herein by reference in its entirety is the Sequence Listing being concurrently submitted via EFS-Web as an ASCII text file named SEQLIST.txt, created Feb. 13, 2013, and having a size of 2,457 bytes.

This invention was made with government support under grant Nos. CA138533, CA111766, and CA100098 awarded by the National Institutes of Health, National Cancer Institute. The government has rights in the invention.

FIELD OF THE INVENTION

The present invention relates generally to methods of delivering a nucleic acid molecule to patient. The present invention also relates to compositions and methods for the treatment of cancer.

BACKGROUND OF THE INVENTION

Ovarian cancer is one of the most common causes of cancer death from gynecologic malignancy in the industrialized world. Standard treatment involves aggressive cytoreductive (debulking) surgery followed by chemotherapy. Ovarian cancer may spread to the lining of the abdominal cavity as intraperitoneal metastases (carcinomatosis) and leads to ascites. In general, carcinomatosis and ascites indicate a more advanced stage of the disease that usually requires extensive high dose chemotherapy (Berkenblit et al. (2005) J. Reprod. Med., 50:426-438; Kawaguchi et al. (2005) Curr. Drug Targets Cardiovasc. Haematol. Disord., 5:39-64). Furthermore, tumor cells from malignant ascites are more invasive and resistant to chemotherapy when compared with primary ovarian tumors (Lane et al. (2010) J. Ovarian Res., 3:1; Tang et al. (2010) Neoplasia 12, 128-138; Veatch et al. (1994) Int. J. Cancer 58:393-399). The precise mechanisms underlying the formation of ascites in ovarian cancer are unknown. However, it is known that the success of chemotherapeutic treatment of primary ovarian cancer and especially tumor cells growing in ascitic fluid is limited by the intrinsic and acquired resistance of cancer cells to chemotherapy (Lane et al. (2010) J. Ovarian Res., 3:1; Tang et al. (2010) Neoplasia 12, 128-138; Veatch et al. (1994) Int. J. Cancer 58:393-399; Li et al. (2009) BMC Cancer 9:323). Such resistance requires the use of multiple chemotherapeutic agents thus increasing the rate of severe adverse side effects of therapy on healthy organs and tissues.

The main mechanisms of multidrug resistance are common to most cancers and include "pump" and "nonpump" resistance (Liu et al. (1998) Gynecol. Oncol., 70:398-403; Minko et al. (2004) Curr. Drug Targets 5:389-406; Pakunlu et al. (2003) Pharm. Res., 20:351-359; Pakunlu et al. (2004) Cancer Res., 64:6214-6224; Krasznai et al. (2005) Anticancer Res., 25:1187-1192). Pump resistance is caused by membrane transporters that pump out the anticancer agents from cells, decreasing the intracellular drug concentration and thereby the efficacy of the treatment. The main mechanism of nonpump resistance is an activation of cellular antiapoptotic defense. Effective treatment of advanced multidrug resistant primary ovarian tumors and their intraperitoneal metastases may be possible only by suppressing simultaneously at least two main types of cellular resistance and by inducing cell death using several anticancer agents with different mechanisms of action. Such an objective can be best achieved if several anticancer agents are simultaneously delivered specifically to the tumor in combination with other active components that perform different functions for enhancing cellular uptake and efficiency of drugs in cancer cells, limiting adverse side effects, and preventing the development of drug resistance and metastases.

SUMMARY OF THE INVENTION

In accordance with the instant invention, methods of treating, preventing, or inhibiting cancer in a patient are provided. In a particular embodiment, the method comprises administering to a patient at least one chemotherapeutic agent (particularly at least two chemotherapeutic agents with different mechanisms of action) and at least one, particularly at least two, inhibitors of cellular drug resistance (e.g., inhibitors of pump resistance and/or inhibitors of nonpump resistance). In yet another embodiment, the chemotherapeutic agents and the inhibitors of cellular drug resistance are contained within a drug delivery system (DDS) that utilizes a nanocarrier (e.g., a liposome or dendrimer such as a poly(propyleneimine) (PPI) dendrimer). The DDS may comprise at least one targeting ligand, particularly at least one cancer targeting ligand, e.g., Luteinizing Hormone-Releasing Hormone (LHRH) or an analog thereof.

According to another aspect of the instant invention, methods of delivering a nucleic acid, particularly an siRNA or an antisense molecule, to a cell are provided. In a particular method, these methods are used in coordination with the above therapeutic methods. In a particular embodiment, the methods of delivering an siRNA or antisense molecule comprise A) forming a complex comprising siRNA and an antisense molecule and a dendrimer (e.g., a poly(propyleneimine) (PPI) dendrimer) and B) contacting a cell (in vitro or in vivo) with the complex. In a particular embodiment, the PPI dendrimer is a generation four (G4) or five (G5) dendrimer. In yet another embodiment, the siRNA or antisense molecule is a therapeutic molecule (e.g., an inhibitor of cellular drug resistance) and the delivery of the siRNA or antisense molecule is used to treat a disease or disorder (e.g., delivered to a subject). In a particular embodiment, the disease or disorder is cancer. The complex may further comprise a targeting ligand (e.g., cancer targeting ligand) for directing the dendrimer to a specific cell type (e.g., cancer cells). In a particular embodiment, the targeting ligand is linked to the dendrimer via a polyethylene glycol linker. In a particular embodiment, the targeting ligand is luteinizing hormone-releasing hormone (LHRH) or an analog thereof. The complex may further comprise at least one chemotherapeutic agent. The complex may further comprise an imaging agent. Compositions comprising at least one molecule of siRNA complexed with the dendrimer and at least one pharmaceutically acceptable carrier are provided.

According to another aspect of the instant invention, compositions comprising a liposome or dendrimer comprising at least one chemotherapeutic agents (particularly at least two chemotherapeutic agents with different mechanisms of action), at least one, particularly at least two, inhibitors of cellular drug resistance (e.g., inhibitors of pump resistance and/or inhibitors of nonpump resistance), and at least one pharmaceutically acceptable carrier are provided. In another embodiment, the liposome or dendrimer comprise all of the above components or part of the above components. In certain embodiment, the siRNA molecules are contained within the dendrimers.

According to another aspect of the instant invention, a compound comprising a polyamidoamine (PAMAM) dendrimer, polyethylene glycol (PEG), and poly-L-lysine is provided. The compound is an effective carrier of nucleic acid molecules such as siRNA and antisense molecules. Compositions comprising the compound, at least one pharmaceutically acceptable carrier, and, optionally, at least one siRNA or antisense molecule are also encompassed by the instant invention. Methods of delivering an siRNA or antisense molecule to a cell method comprising forming a complex the above compound are also provided.

BRIEF DESCRIPTIONS OF THE DRAWING

Figure 1E:
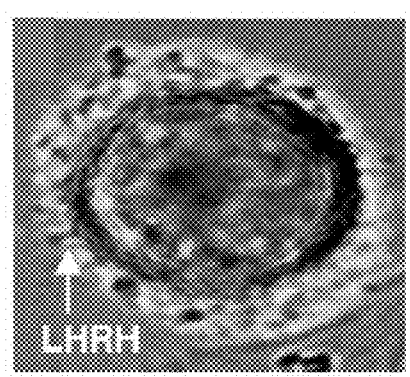
Figure 1F:
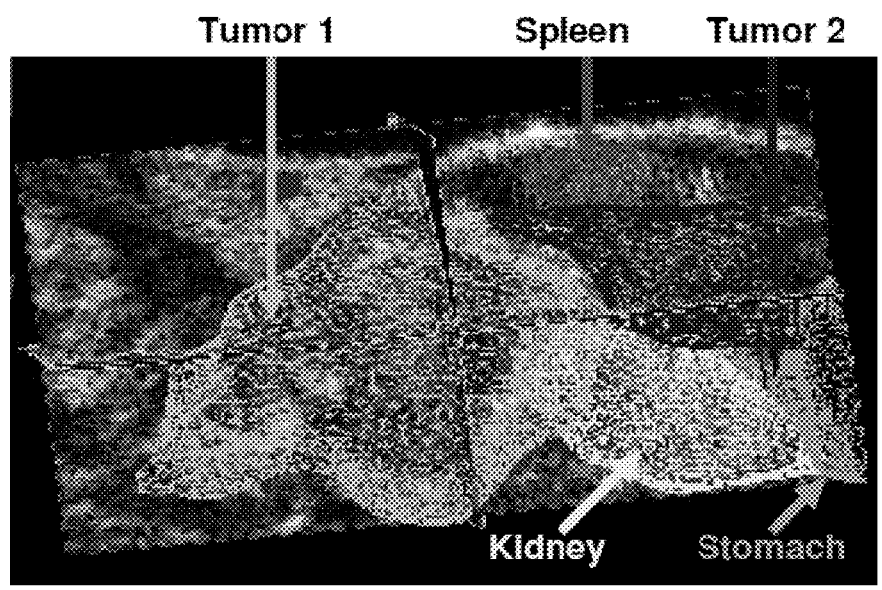
Figure 1G:
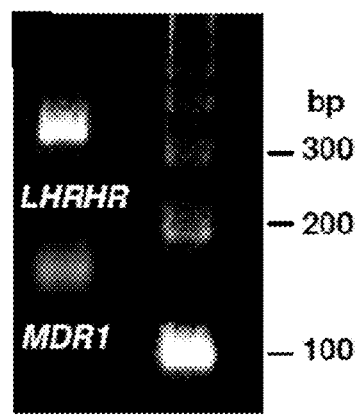
Figure 1H:
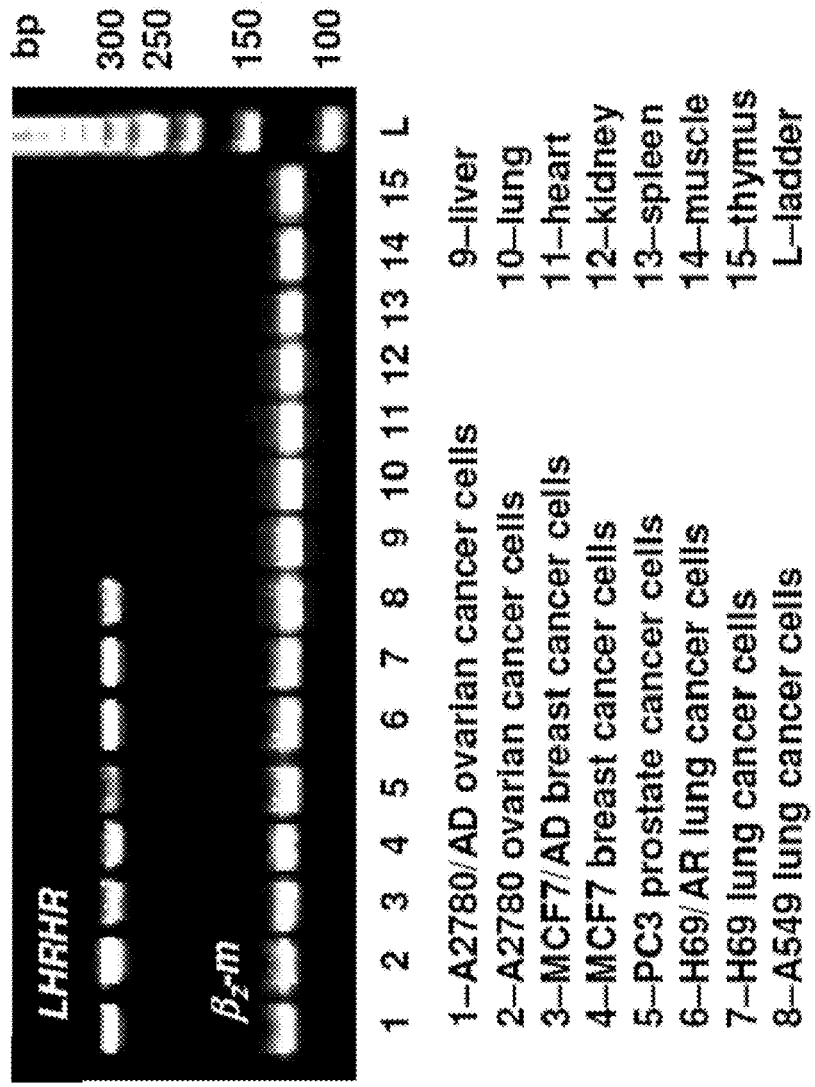
Figure 1I:
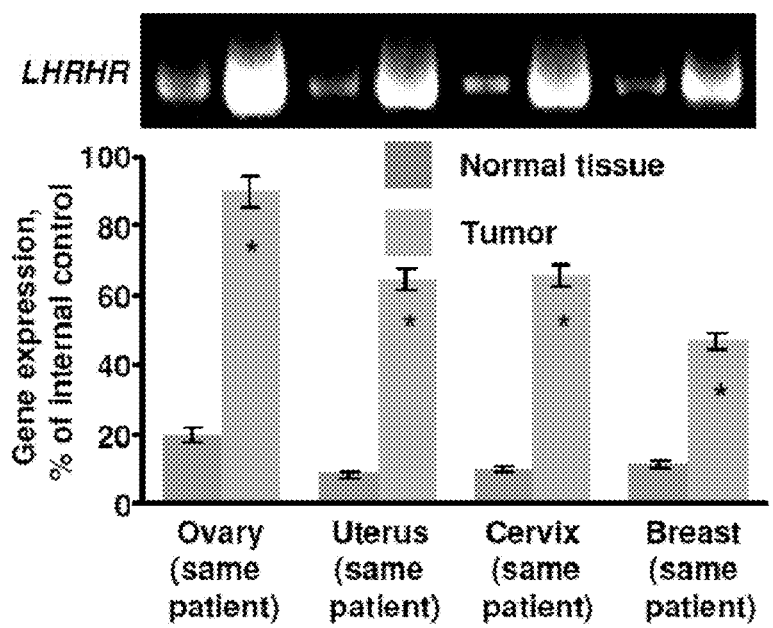
Figure 1J:
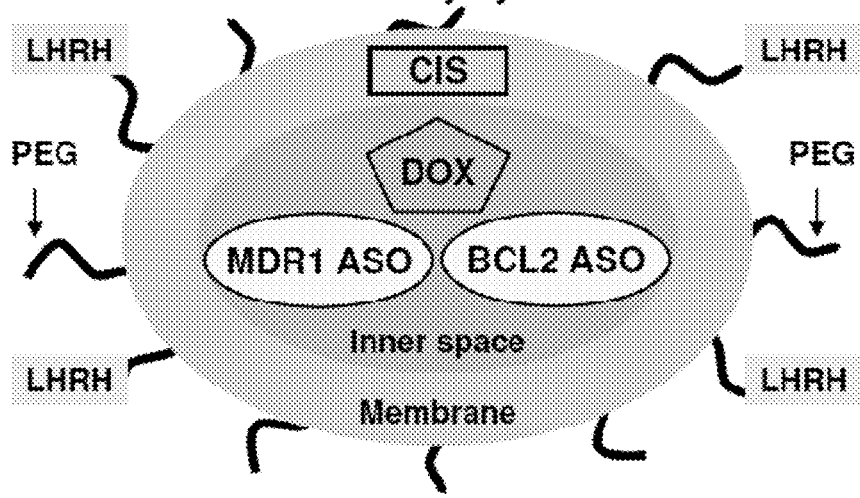

FIG. 1A is a representative image of cells isolated from human malignant ascites and transfected with luciferase or green fluorescent protein. Cells isolated from human malignant ascites were injected into the flanks of nude mice resulting in the formation of solid primary tumor (FIG. 1B) and intraperitoneal metastases (FIGS. 1C, 1D, and 1F). Typical bioluminescent (FIGS. 1B and 1C, IVIS imaging system) and ultrasound (FIGS. 1D and 1F, Vevo 2100® imaging system) images of a live anesthetized mouse with primary and metastatic tumors. FIG. 1E shows the expression of LHRH receptors (LHRHR) in the plasma membrane of cells isolated from human malignant ascites obtained from patients with ovarian carcinoma. The cells were incubated with LHRH peptide labeled by Rhodamine (red fluorescence). FIG. 1G shows the expression of LHRHR and MDR1 gene encoding P-glycoprotein in cells isolated from human malignant ascites. FIGS. 1H and 1I are representative images of gel electrophoresis and quantitation of RT-PCR products of gene encoding LHRHR. Means±S.D. are shown. *$P<0.05$ when compared with healthy tissues from the same patient. FIG. 1J is a schematic of a multifunctional tumor-targeted liposomal delivery system.

Figure 2:
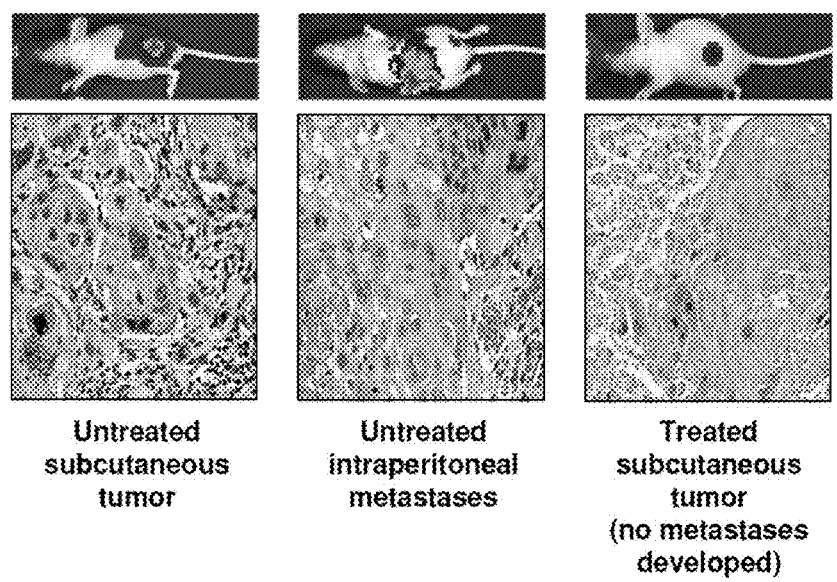

FIG. 2 shows the histology of tumor and intraperitoneal metastases. Treatment of aggressive subcutaneous tumor with combination therapy (LHRH-Lip-DOX-BCL2-MDR1 ASO+LHRH-Lip-CIS-BCL2-MDR1 ASO) led to the significant changes in histopathological pattern of the developed solid subcutaneous and metastatic tumors. Upper panels: typical IVIS images of mice bearing subcutaneous xenografts of human malignant ascites. The tumor was accompanied by the development of intraperitoneal metastases. Bottom panels: typical microscopy images of tumor tissues and intraperitoneal metastases stained with hematoxylin-eosin.

Figure 3A:
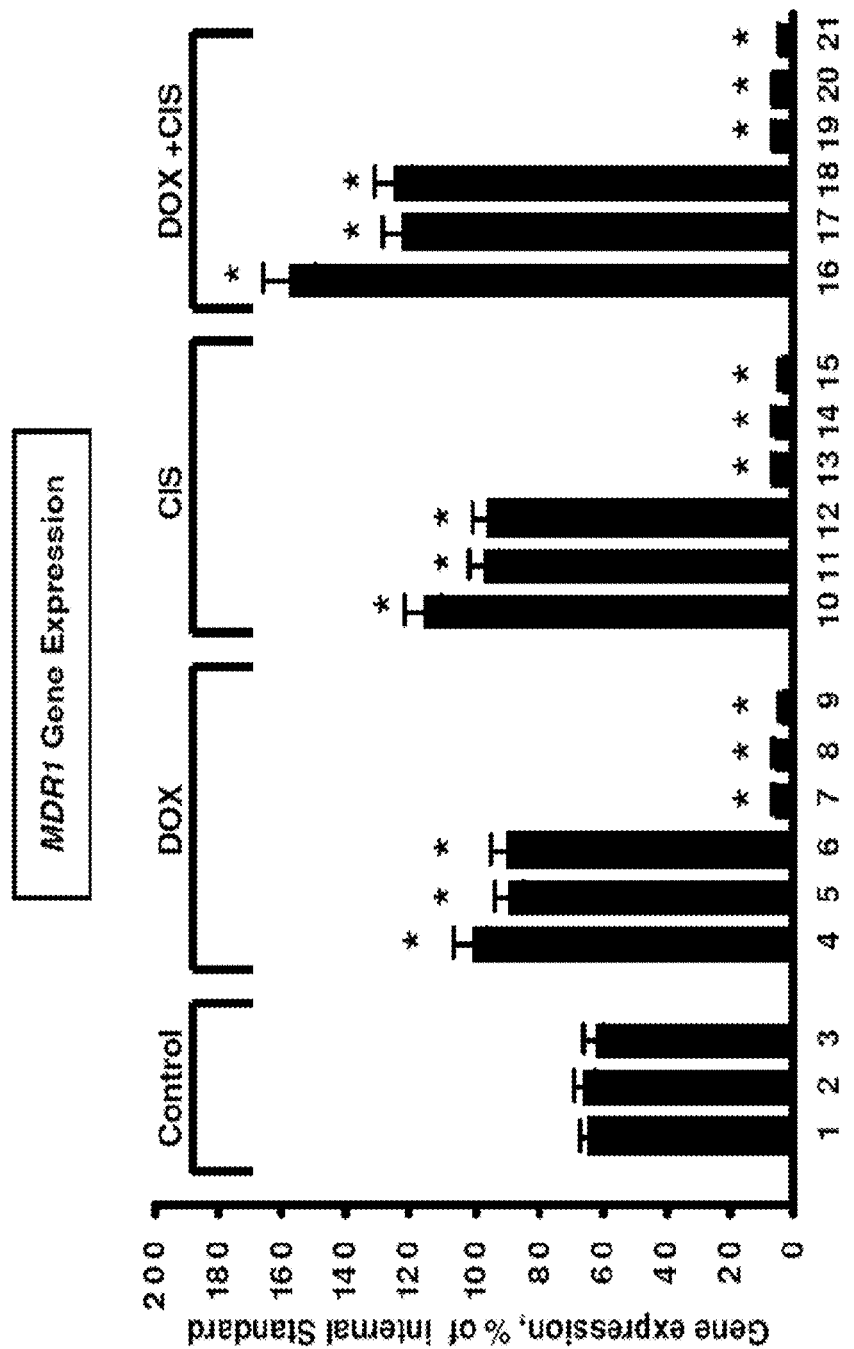
Figure 3B:
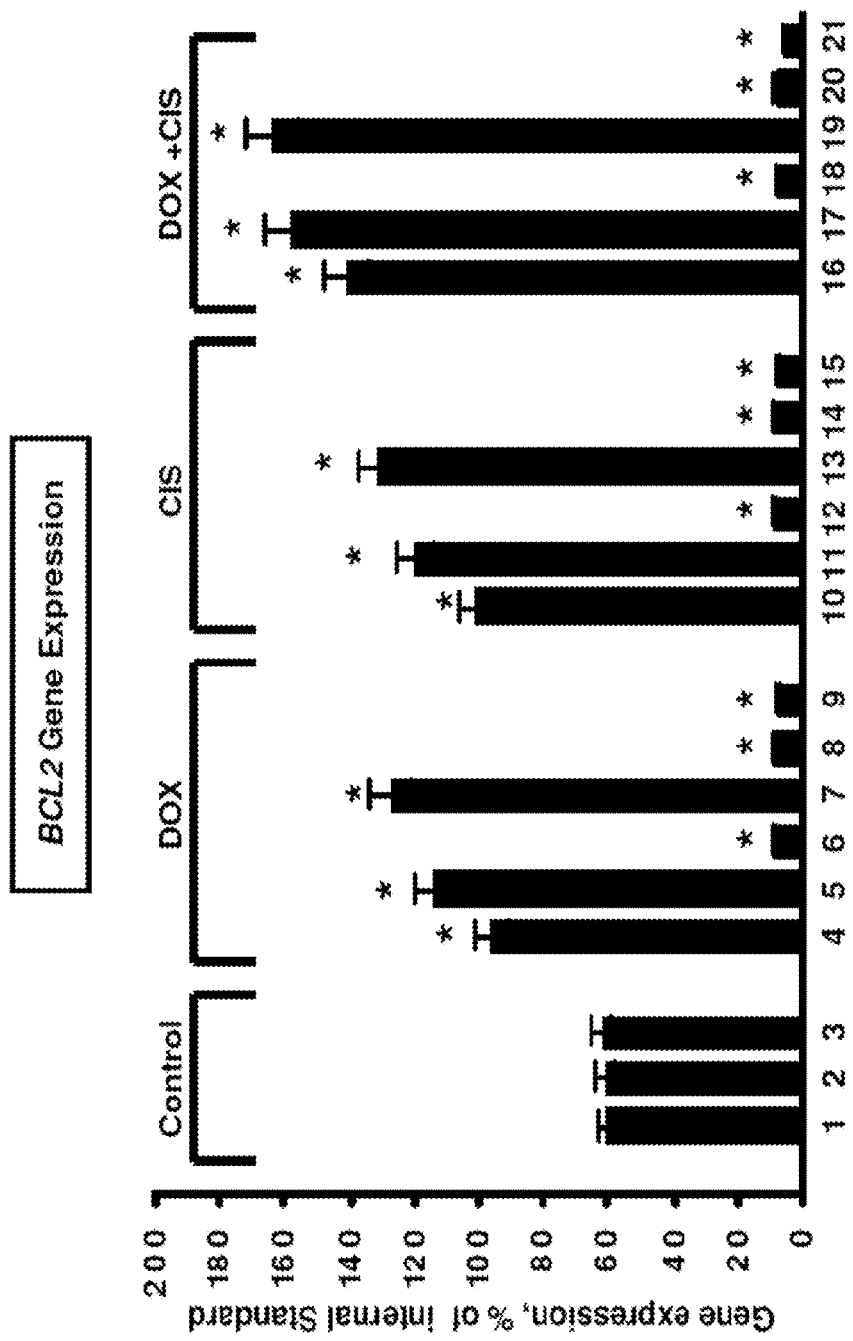

FIG. 3 demonstrates the gene expression in subcutaneous tumors. FIG. 3A shows MDR1 gene expression and FIG. 3B shows BCL2 gene expression. Mice bearing xenografts of human malignant ascites were treated 8 times within 30 days with the following substances: (1) Saline (untreated control); (2) Liposomes (Lip); (3) LHRH; (4) Doxorubicin (DOX); (5) Lip-DOX; (6) Lip-DOX-BCL2 ASO; (7) Lip-DOX-MDR1 ASO; (8) Lip-DOX-BCL2-MDR1 ASO; (9) LHRH-Lip-DOX-BCL2-MDR1 ASO; (10) Cisplatin (CIS); (11) Lip-CIS; (12) Lip-CIS-BCL2 ASO; (13) Lip-CIS-MDR1 ASO; (14) Lip-CIS-BCL2-MDR1 ASO; (15) LHRH-Lip-CIS-BCL2-MDR1 ASO; (16) DOX+CIS; (17) Lip-DOX+Lip-CIS; (18) Lip-DOX-BCL2 ASO+Lip-CIS-BCL2 ASO; (19) Lip-DOX-MDR1 ASO+Lip-CIS-MDR1 ASO; (20) Lip-DOX-BCL2-MDR1 ASO+Lip-CIS-BCL2-MDR1 ASO; (21) LHRH-Lip-DOX-BCL2-MDR1 ASO+LHRH-Lip-CIS-BCL2-MDR1 ASO. Means±S.D. are shown. *$P<0.05$ when compared with untreated control.

FIG. 4 shows the protein expression in subcutaneous tumors. Typical images of tumor tissue sections stained with antibody against P-glycoprotein (FIG. 4A), BCL2 (FIG. 4B) and Caspase 3 (FIG. 4C) proteins. High intensity of the color indicates high protein concentration. Mice bearing xenografts of human malignant ascites were treated 8 times within 30 days with the following substances: (1) Saline (untreated control); (2) DOX+CIS; (3) Lip-DOX; (4) Lip-CIS; (5) Lip-DOX+Lip-CIS; (6) Lip-DOX-BCL2-MDR1-ASO; (7) LHRH-Lip-CIS-BCL2-MDR1-ASO; (8) LHRH-Lip-DOX-BCL2-MDR1-ASO; (9) LHRH-Lip-CIS-BCL2-MDR1-ASO; (10) LHRH-Lip-DOX-BCL2-MDR1-ASO+LHRH-Lip-CIS-BCL2-MDR1-ASO.

Figure 5:
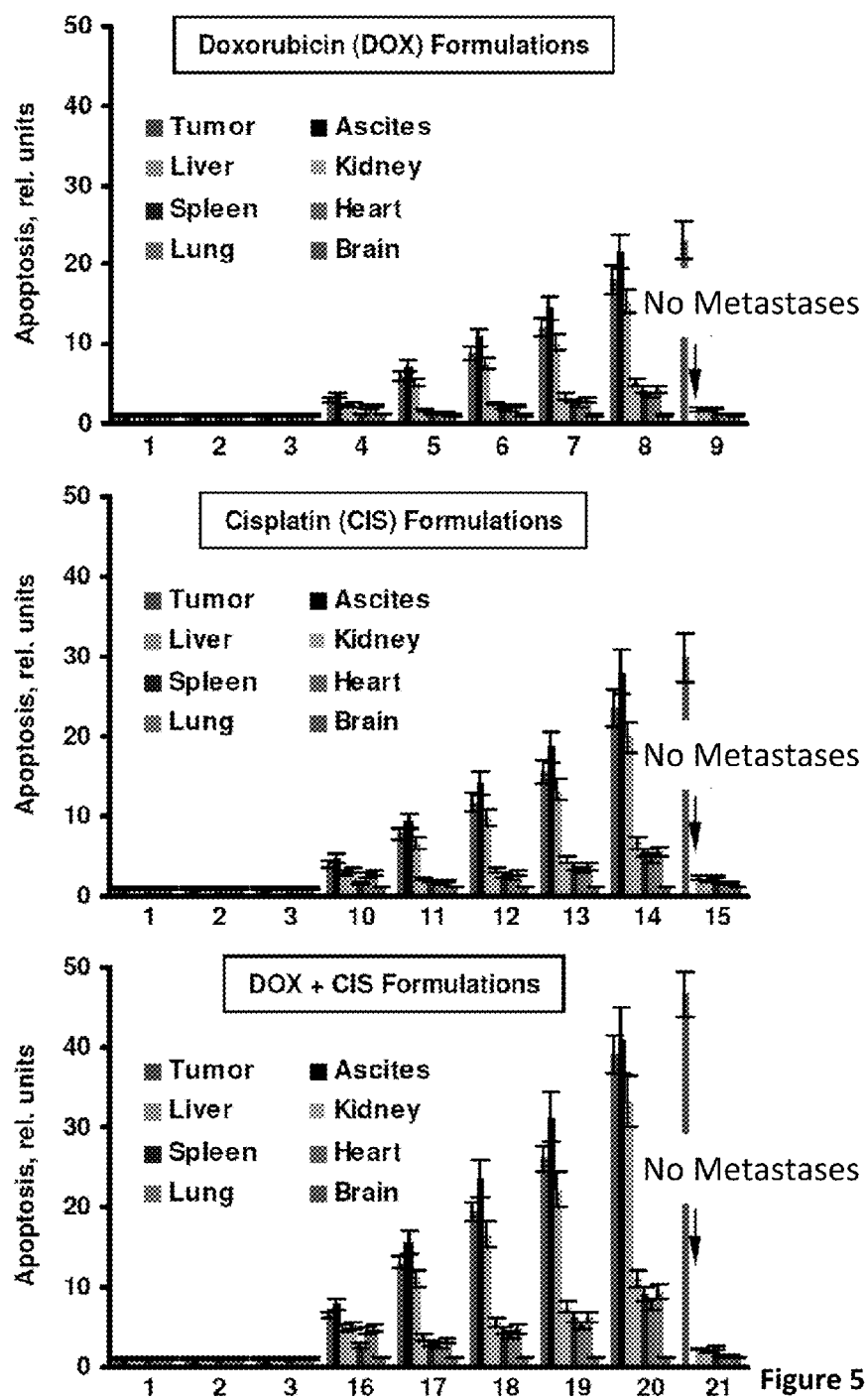

FIG. 5 provides graphs of the apoptosis induction in subcutaneous tumors and intraperitoneal metastases. Mice bearing xenografts of human malignant ascites were treated 8 times within 30 days with the following substances: (1) Saline (untreated control); (2) Liposomes (Lip); (3) LHRH; (4) DOX; (5) Lip-DOX; (6) Lip-DOX-BCL2 ASO; (7) Lip-DOX-MDR1 ASO; (8) Lip-DOX-BCL2-MDR1 ASO; (9) LHRH-Lip-DOX-BCL2-MDR1 ASO; (10) CIS; (11) Lip-CIS; (12) Lip-CIS-BCL2 ASO; (13) Lip-CIS-MDR1 ASO; (14) Lip-CIS-BCL2-MDR1 ASO; (15) LHRH-Lip-CIS-BCL2-MDR1 ASO; (16) DOX+CIS; (17) Lip-DOX+Lip-CIS; (18) Lip-DOX-BCL2 ASO+Lip-CIS-BCL2 ASO; (19) Lip-DOX-MDR1 ASO+Lip-CIS-MDR1 ASO; (20) Lip-DOX-BCL2-MDR1 ASO+Lip-CIS-BCL2-MDR1 ASO; (21) LHRH-Lip-DOX-BCL2-MDR1 ASO+LHRH-Lip-CIS-BCL2-MDR1 ASO. Means±S.D. are shown.

Figure 6A:
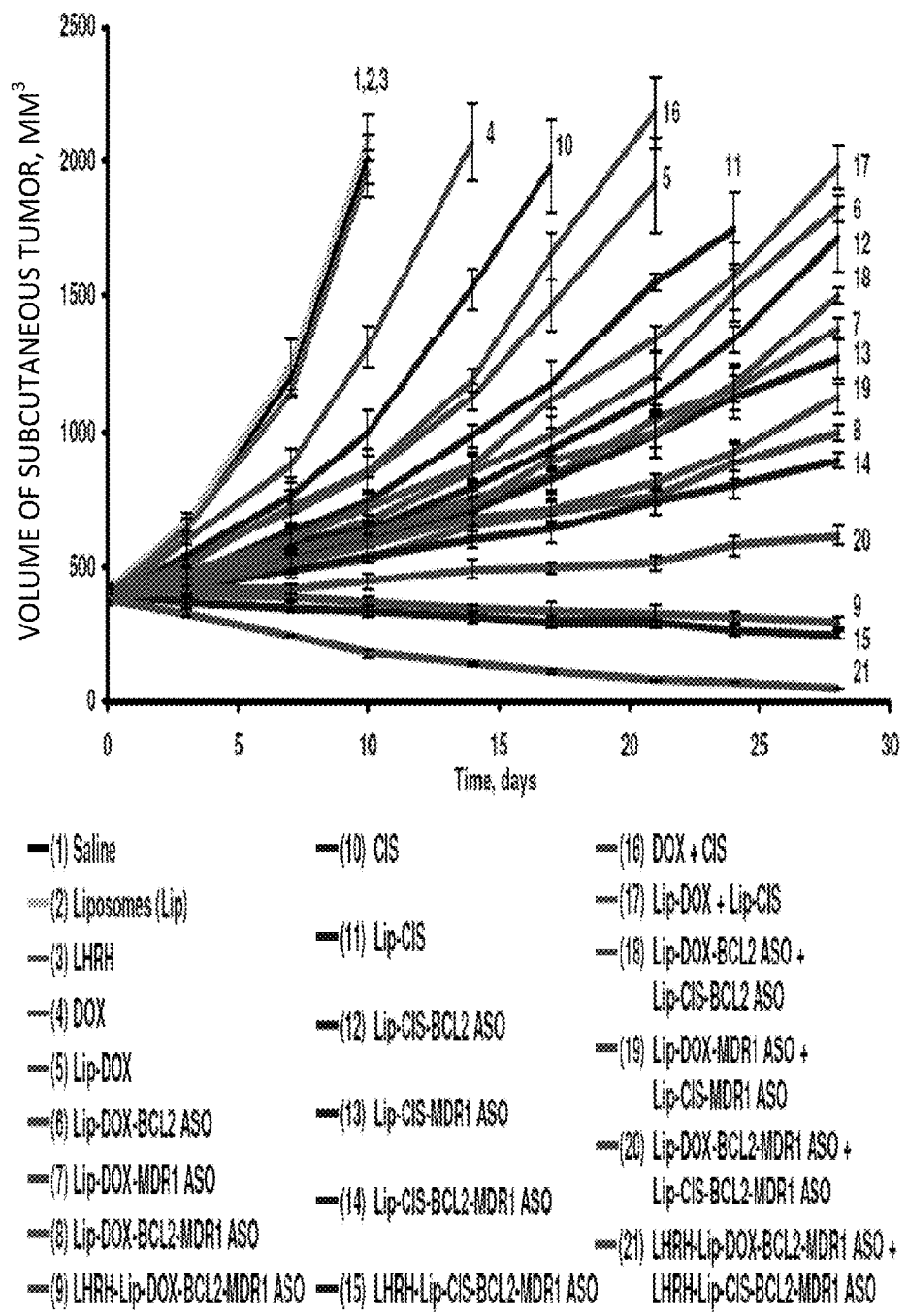
Figure 6B:
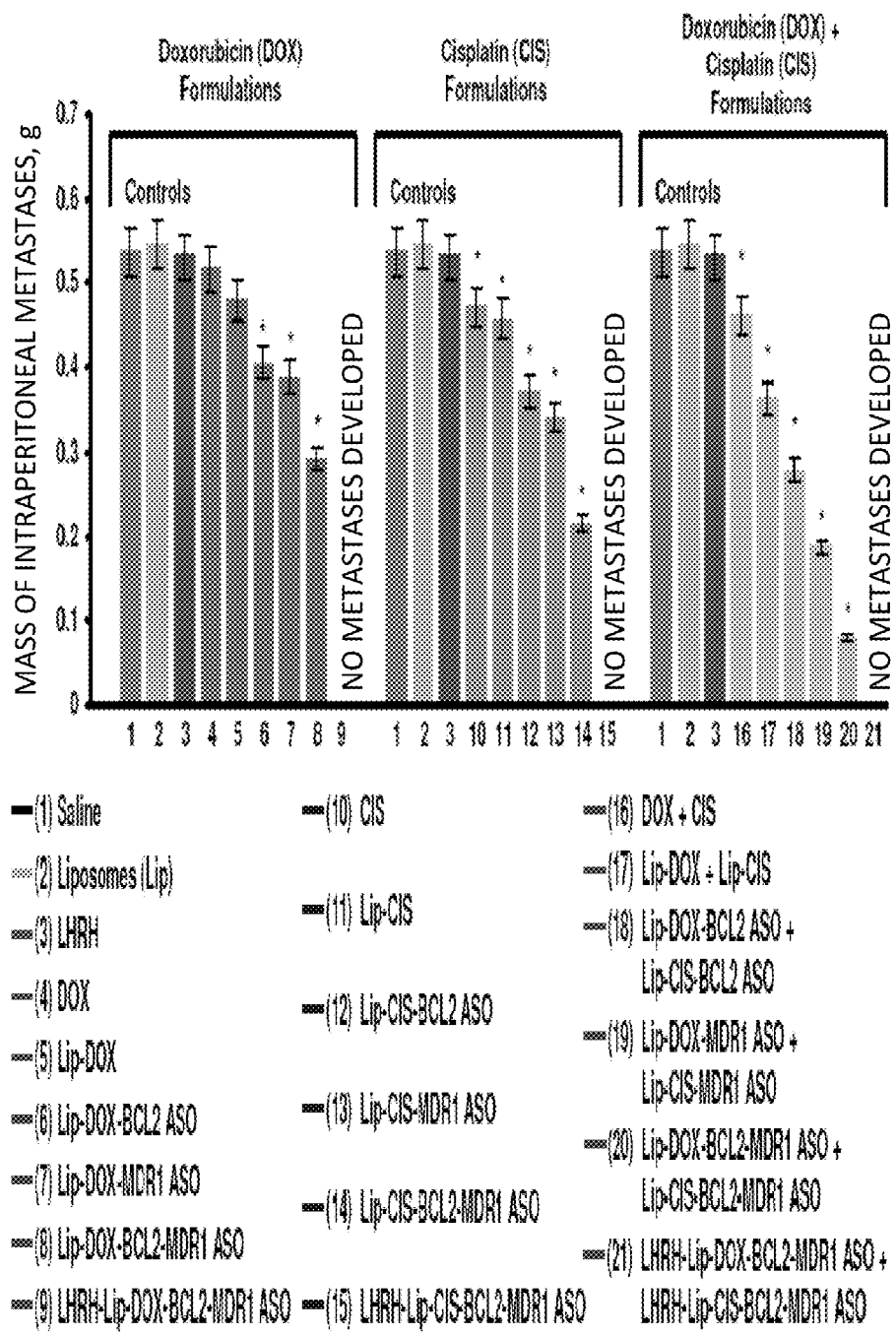

FIG. 6 demonstrates the treatment with tumor-targeted complex delivery systems containing two anticancer drugs with different mechanisms of action and suppressors of pump and nonpump cellular drug resistance substantially inhibits the growth of subcutaneous tumor and prevents the development of intraperitoneal metastases. Cancer cells were isolated from malignant ascites obtained from patients with ovarian carcinoma and injected subcutaneously into the flanks of nude mice. When the tumors reached a size of about 0.3 cm$^3$ (15-20 days after transplantation), mice were treated maximum 8 times within 30 days with substances indicated. FIG. 6A represents tumor growth during the treatment and FIG. 6B represents the mass of intraperitoneal metastases at the end of the treatment. Means±S.D. are shown. *$P<0.05$ when compared with untreated tumor (saline).

Figure 7A:
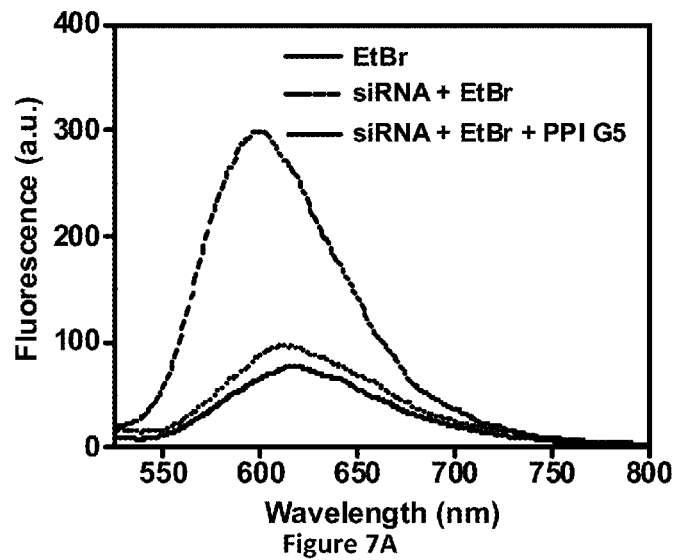
Figure 7B:
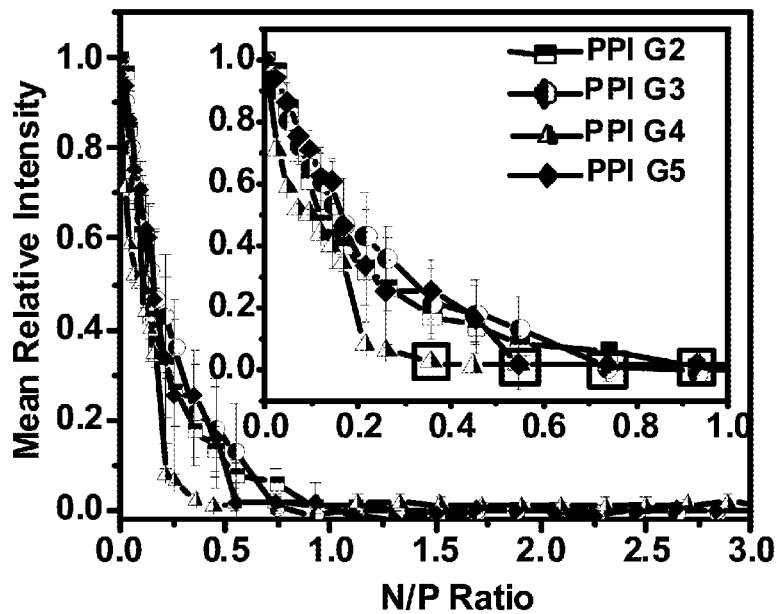

FIG. 7A provides a representative fluorescence spectra of EtBr alone, EtBr after complexation with siRNA and EtBr after displacement from siRNA by PPI G5 (N/P=2.4). FIG. 7B shows EtBr dye displacement assay by PPI dendrimers. The inset provides an enlargement of the graphs in the vicinity of N/P ratios which represent the apparent ends of complexation. The highlighted areas on the graphs demonstrate the N/P ratios, which correspond to the apparent end of siRNA complexion by PPI G2, PPI G3, PPI G4 and PPI G5. Means±SD are shown.

Figure 8A:
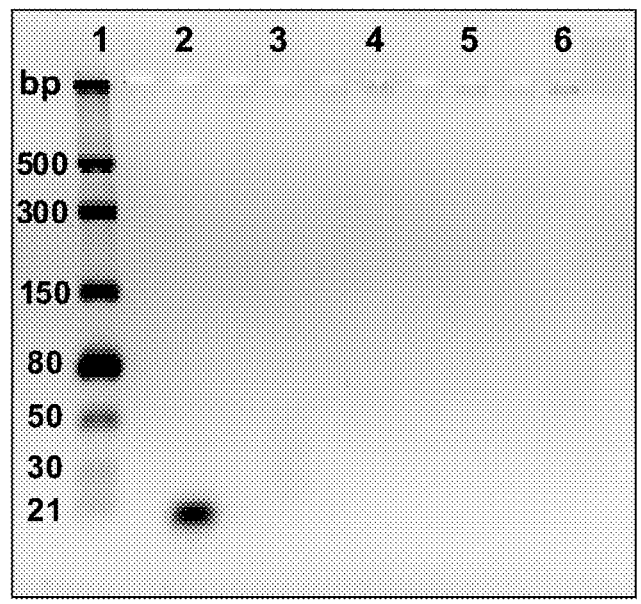
Figure 8B:
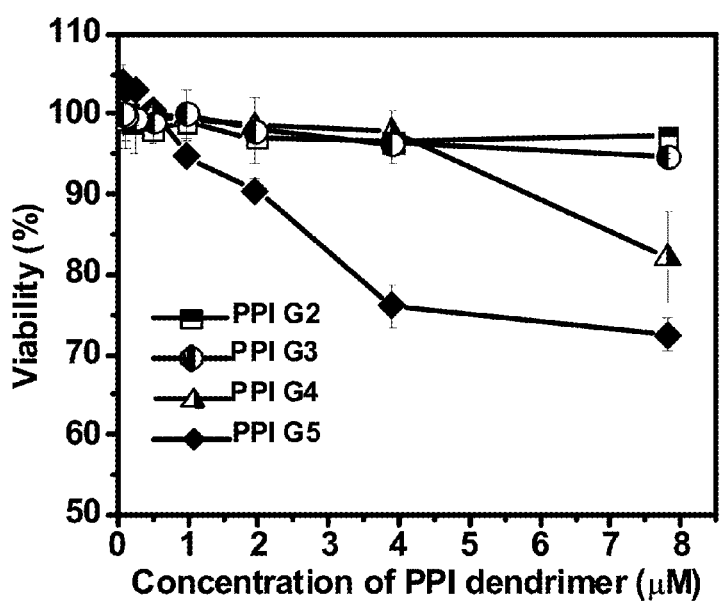

FIG. 8A shows an evaluation of the siRNA complexion with PPI dendrimers by gel retardation assay. (1) RNA size ladder; (2) naked siRNA; (3) siRNA+PPI G2, (4) siRNA+PPI G3, (5) siRNA+PPI G4, (6) siRNA+PPI G5. FIG. 8B provides the viability profile of A549 human lung cancer cells incubated for 24 hours with PPI dendrimers of different generation (from 2 to 5). Means±SD are shown.

FIG. 9 provides representative AFM images of complexes formed by siRNA in the presence of (FIG. 9A) PPI G2, (FIG. 9B) PPI G3, (FIG. 9C) PPI G4, and (FIG. 9D) PPI G5 dendrimers after 30 minutes of complexation. The bar represents 400 nm in FIGS. 9A-9D and 200 nm in the inset.

Figure 10A:
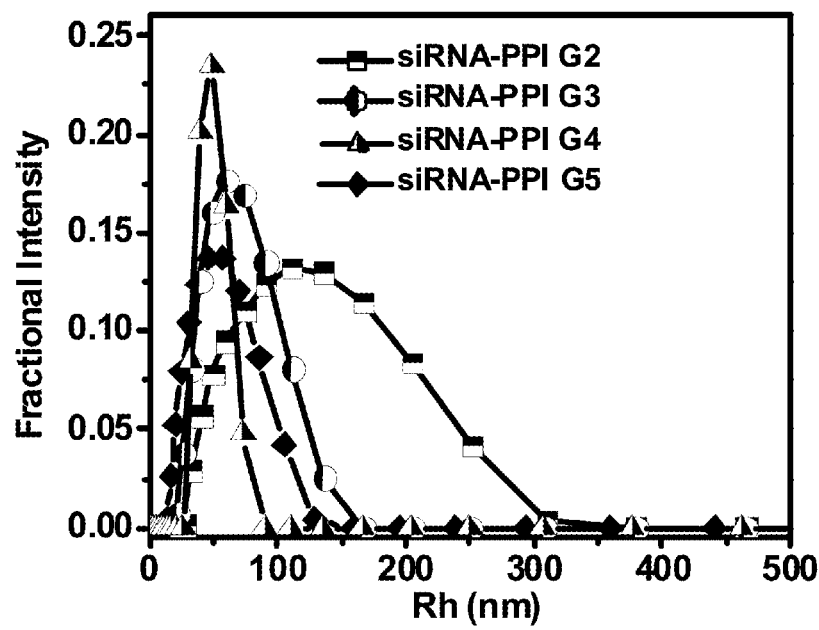
Figure 10B:
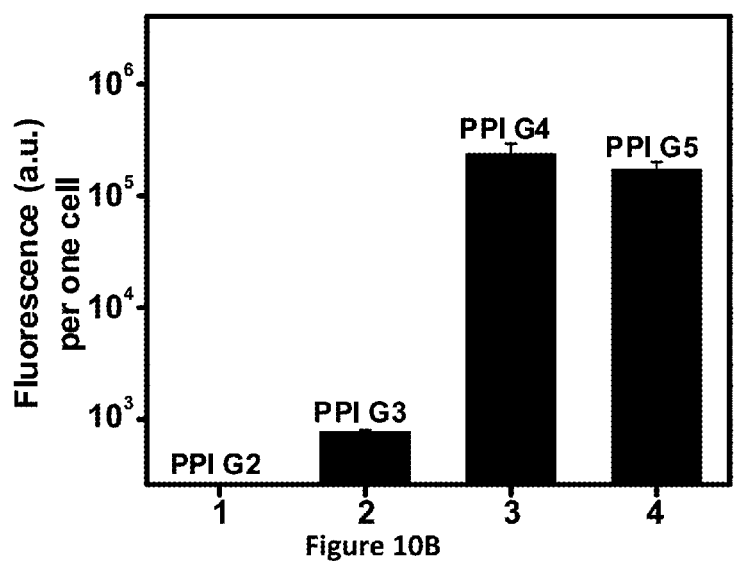

FIG. 10A provides representative curves which demonstrate the size distribution of siRNA-PPI G2, siRNA-PPI G3, siRNA-PPI G4 and siRNA-PPI G5 complexes measured by DLS. Rh is the hydrodynamic radius. FIG. 10B shows the internalization of siRNA complexed with (1) PPI G2; (2) PPI G3; (3) PPI G4 and (4) PPI G5 dendrimers by A549 human lung cancer cells. Intracellular fluorescence intensity of FAM-labelled siRNA was estimated based on fluorescence microscopy images recorded under the same experimental conditions.

Figures 11A, 11B, 11C, 11D, 11E:
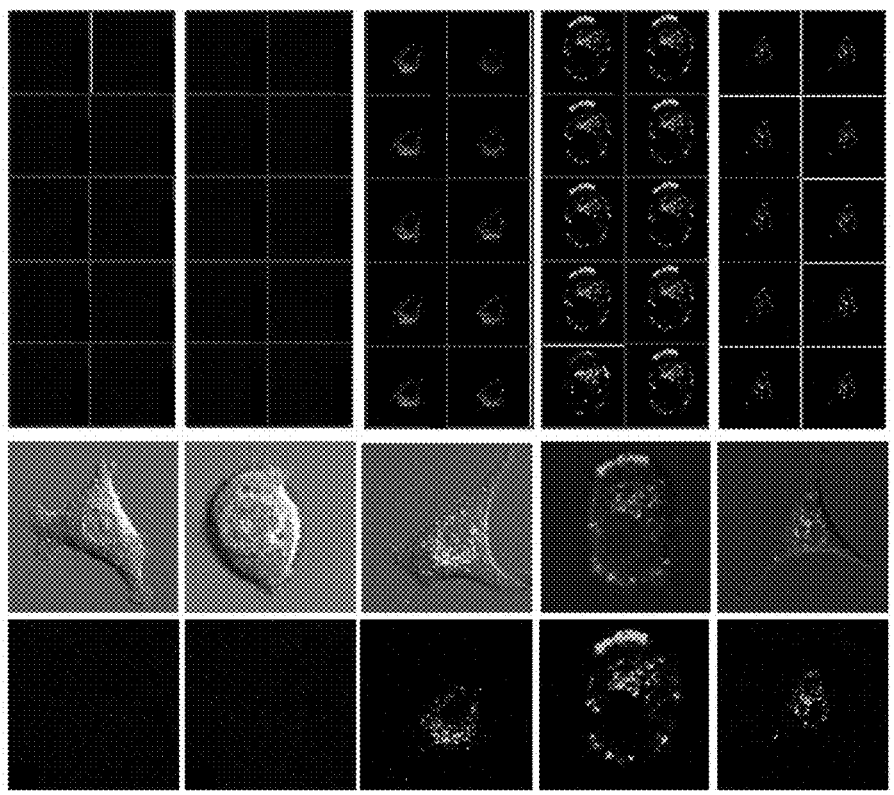

FIG. 11 provides confocal microscopy images (from left to right: fluorescence, superimposed light and fluorescence, z-series) of A549 human lung cancer cells incubated for 24 hours with (FIG. 11A) naked siRNA; (FIG. 11B) siRNA-PPI G2; (FIG. 11C) siRNA-PPI G3; (FIG. 11D) siRNA-PPI G4 and (FIG. 11E) siRNA-PPI G5. Z-series represents fluorescence images from top to the bottom of the cell.

Figure 12A:
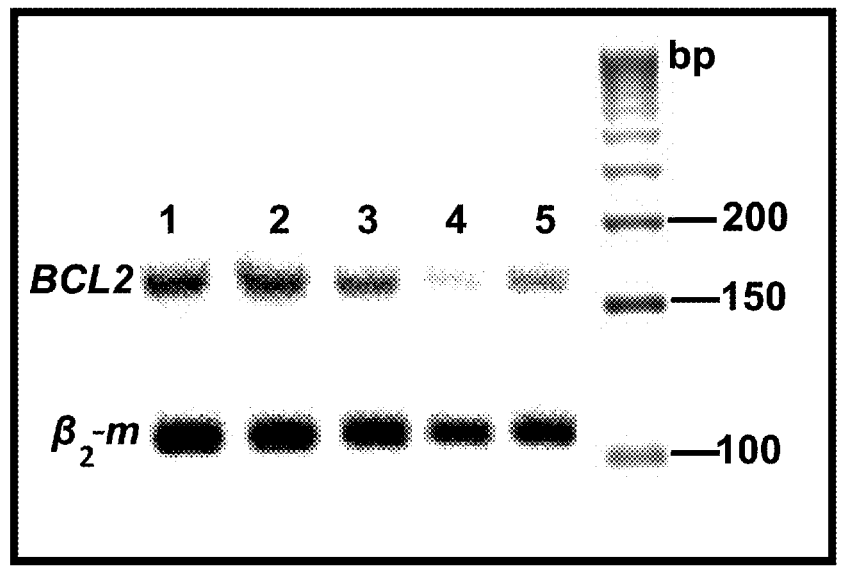
Figure 12B:
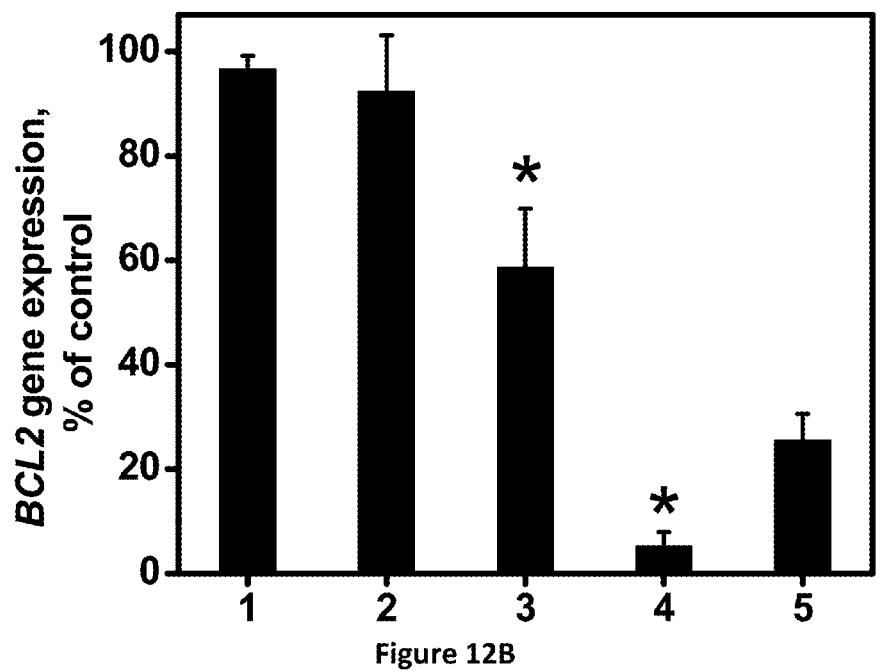

FIG. 12 shows the effect of incubation of A549 human lung cancer cells with (1) medium (control); (2) siRNA-PPI G2; (3) siRNA-PPI G3 (4) siRNA-PPI G4 and (5) siRNA-PPI G5 on the expression of BCL2 mRNA. FIG. 12A provides a typical image of RT-PCR products. FIG. 12B shows gene expression calculated as the ratio of BCL2 RT-PCR product to the internal standard ($\beta_2$-m). Means±SD are shown. *P<0.05 when compared with control.

Figure 13A:
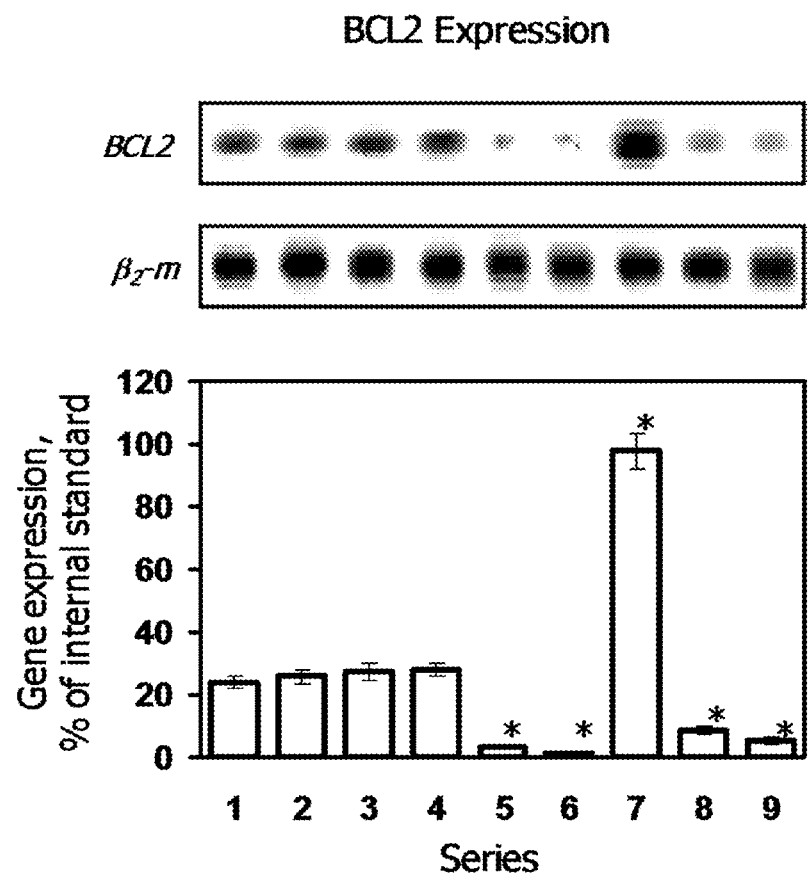
Figure 13B:
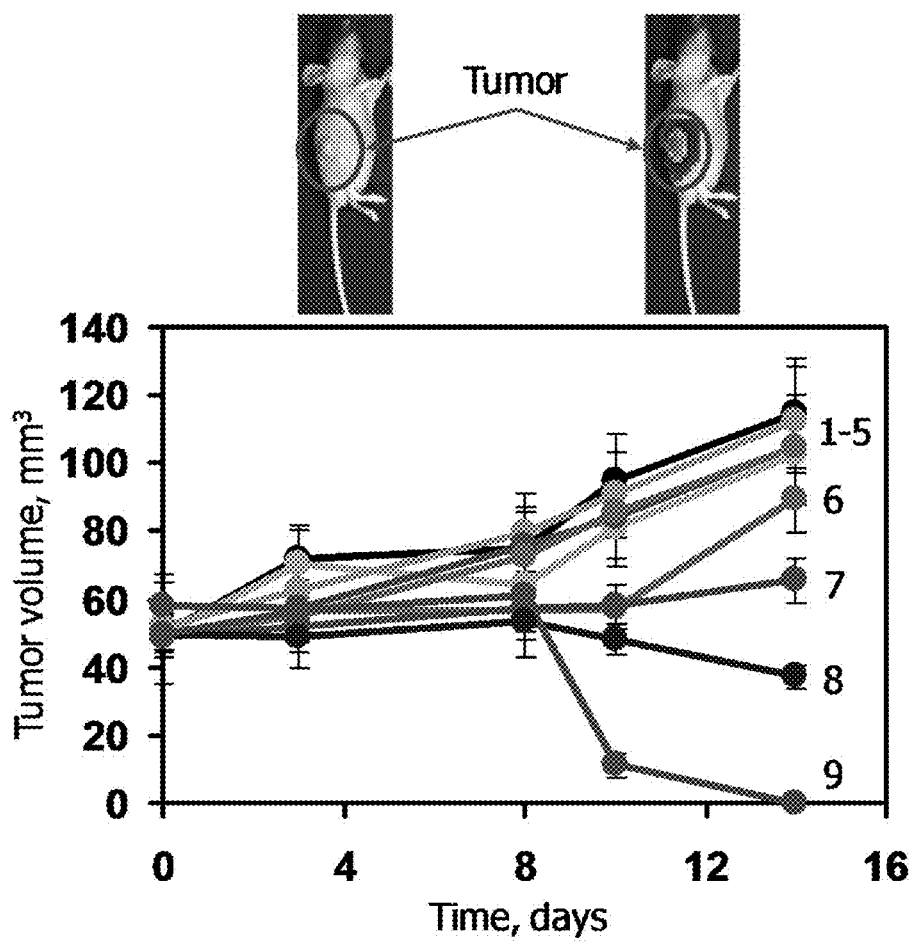

FIG. 13A shows the expression of BCL2 and the expression calculated as the ratio to the internal standard ($\beta_2$-m). FIG. 13B provides a graph of tumor volume over time with the various treatments: (1) Control (saline); (2) PPI dendrimer; (3) LHRH; (4) Naked siRNA targeted to BCL2 mRNA; (5) BCL2 siRNA-PPI-DTBP-PEG; (6) LHRH-BCL2 siRNA-PPI-DTBP-PEG; (7) Free CIS; (8) BCL2 siRNA-PPI-DTBP-PEG+CIS; (9) LHRH-BCL2 siRNA-PPI-DTBP-PEG+CIS. *P<0.05 when compared with control.

Figure 14:
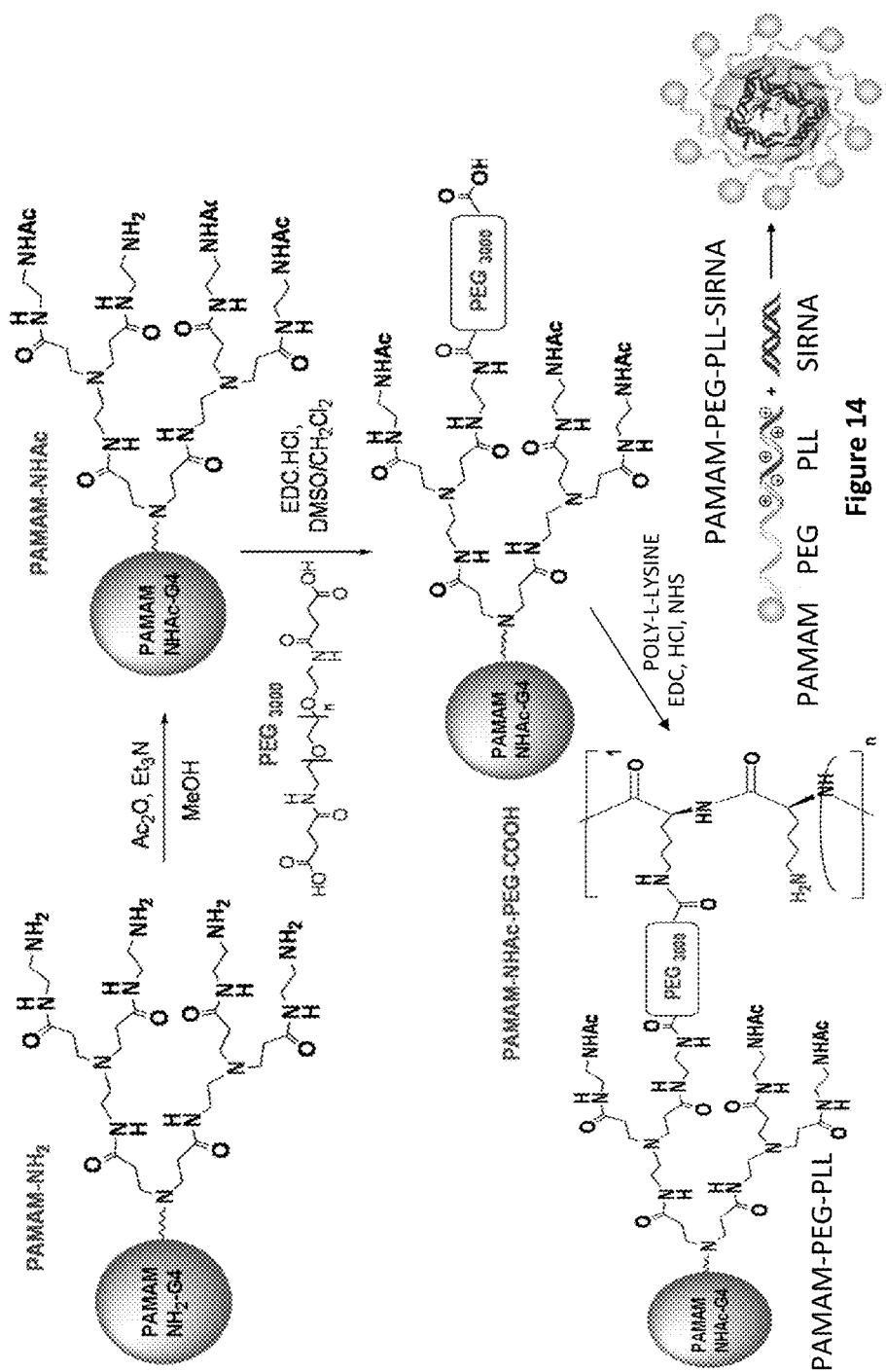

FIG. 14 provides a schematic of the synthesis of triblock PAMAM-PEG-PLL nanocarrier.

Figure 15A:
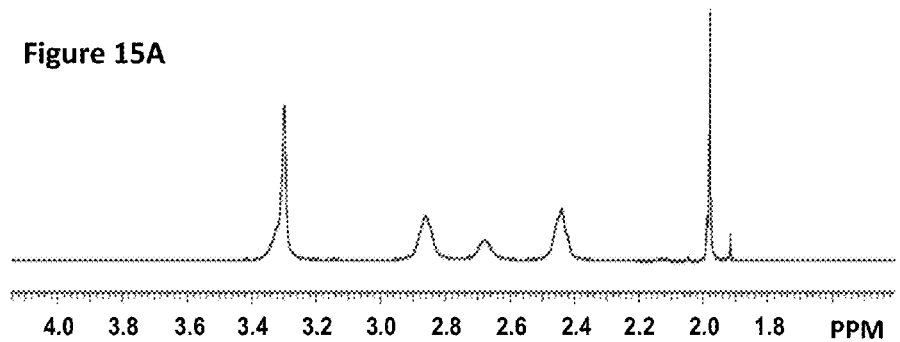
Figure 15B:
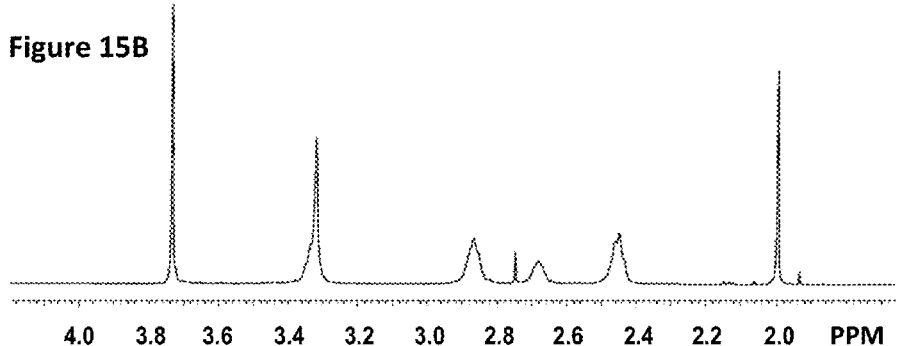

FIG. 15 provides representative $^1$H-NMR spectra in $D_2O$ of PAMAM-NHAc (FIG. 15A); PAMAM-PEG-COOH (FIG. 15B); PAMAM-PEG-PLL (FIG. 15C); and PLL-PEG-OMe (FIG. 15D).

Figure 16A:
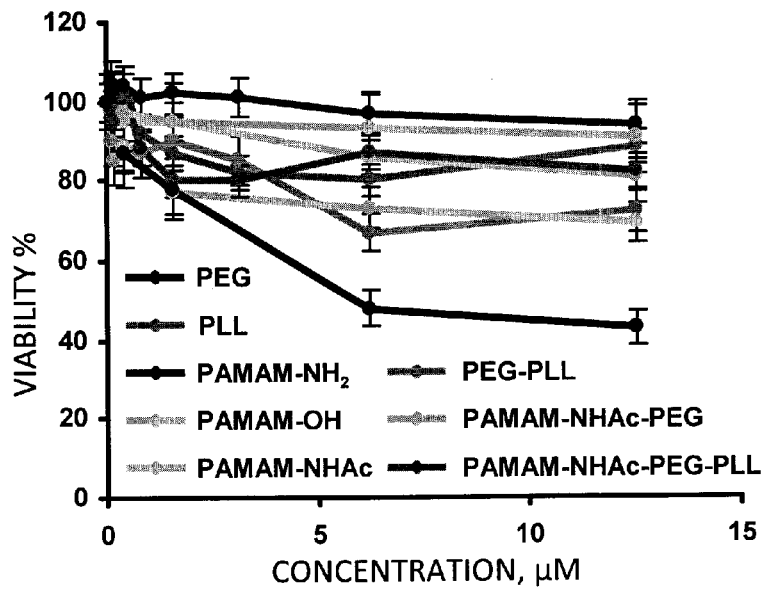
Figure 16B:
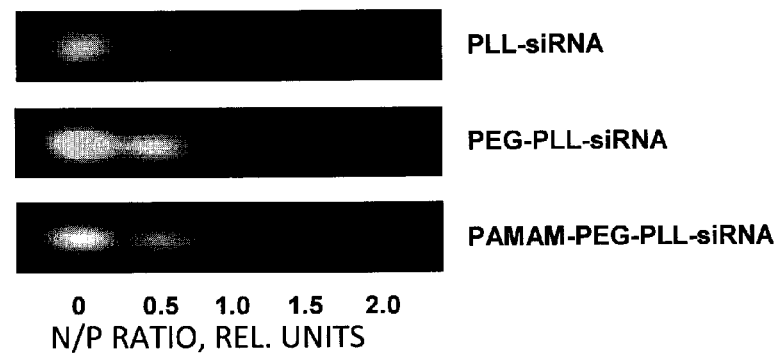
Figure 16C:
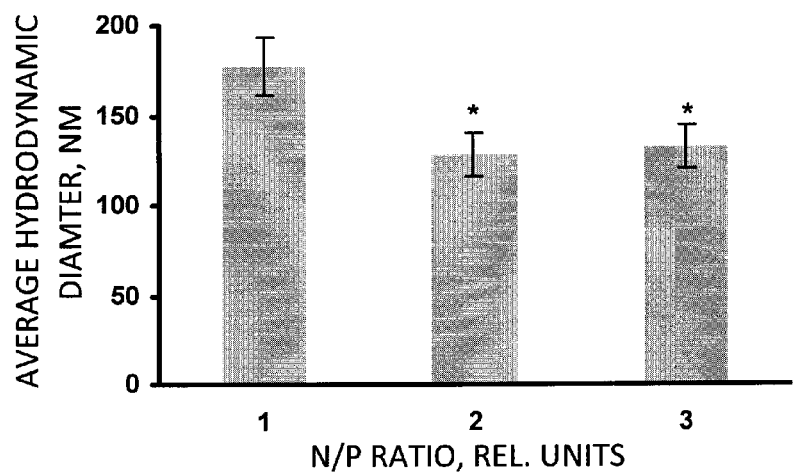

FIG. 16 provides the characterization of different nanocarriers and their complexes with siRNA. FIG. 16A shows the viability of human cancer cells incubated with carriers indicated. Means±SD are shown. FIG. 16B provides representative images of agarose gel electrophoresis of siRNA complexes with different carriers. FIG. 16C provides average hydrodynamic diameter of PAMAM-NHAc-PEG-PLL-siRNA complexes formed at different N/P ratio. Means±SD are shown. *P<0.05 when compared with N/P ratio equal to 1.

FIG. 17 shows the cellular uptake and localization of naked siRNA and PAMAM-PEG-PLL-siRNA complexes. Representative confocal microscopy images of cancer cells incubated with fluorophore labeled siRNA (siGLO Red, red fluorescence): naked siRNA (FIG. 17A); PAMAM-PEG-PLL-siRNA (FIG. 17B); and optical sections z-series of cells incubated with PAMAM-PEG-PLL-siRNA (FIG. 17C).

Figure 18A:
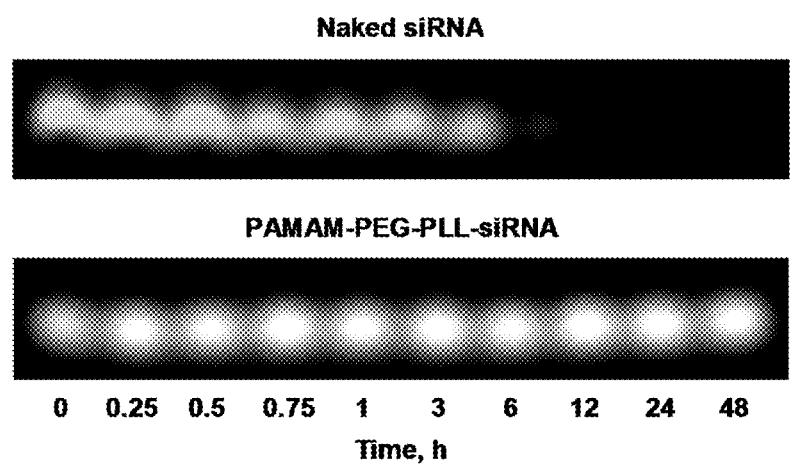
Figure 18B:
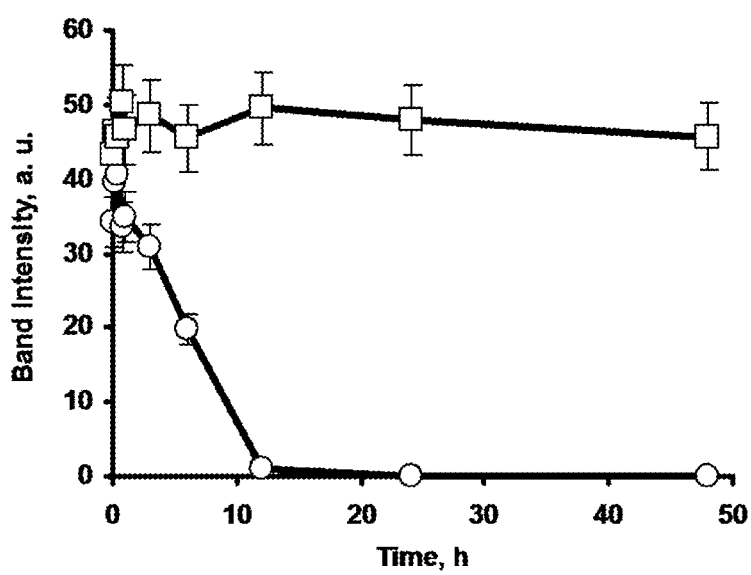

FIG. 18 shows the serum stability of naked and complexated siRNA. FIG. 18A provides representative images of agarose gel electrophoreses of naked siRNA and PAMAM-PEG-PLL-siRNA complexes. FIG. 18B provides a quantitative analysis of band intensity. Means±SD are shown.

Figure 19:
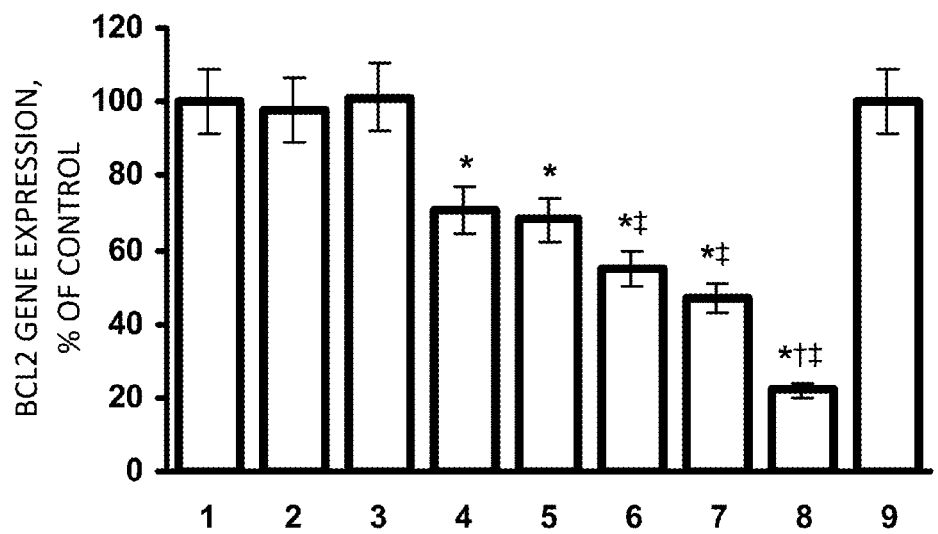

FIG. 19 shows the expression of BCL2 gene in A2780 human ovarian cancer cells incubated with: 1, control (fresh media); 2, naked BCL2 siRNA; 3, naked non-specific siRNA; 4, PAMAM-BCL2 siRNA; 5, PAMAM-PEG-BCL2 siRNA; 6, PLL-BCL2 siRNA; 7, PEG-PLL-BCL2 siRNA; 8, PAMAP-PEG-PLL-BCL2 siRNA; 9, PAMAP-PEG-PLL-BCL2 non-specific siRNA. Means±SD are shown. *P<0.05 when compared with control. †P<0.05 when compared with PLL-siRNA. ‡<0.05 when compared with PAMAM-siRNA.

Figure 20:
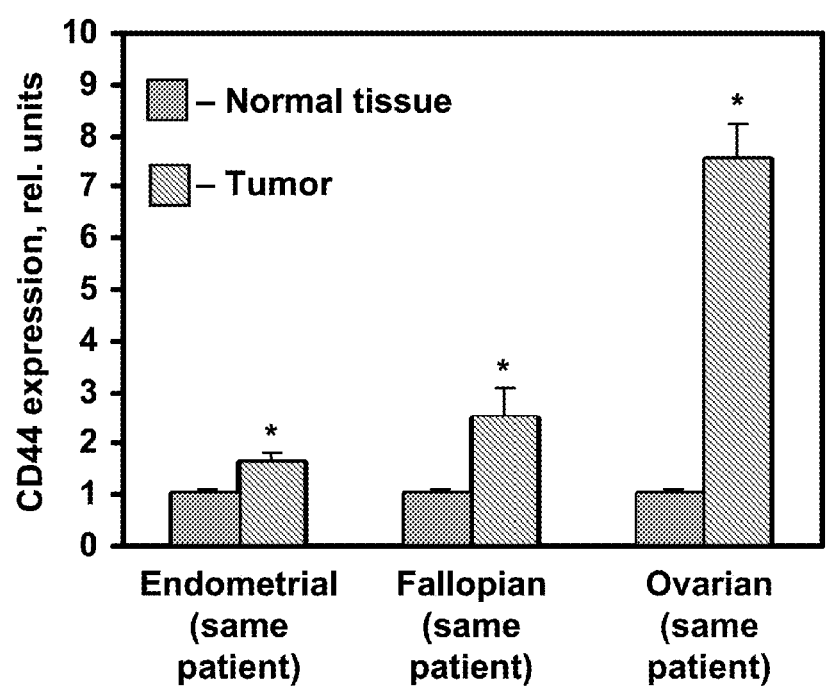

FIG. 20 shows the expression of CD44 mRNA (quantitative RT-PCR) in normal and tumor tissues isolated from patients with different gynecological cancers. Means±SD are shown. P<0.05 when compared with healthy tissues from the same patient.

Figure 21:
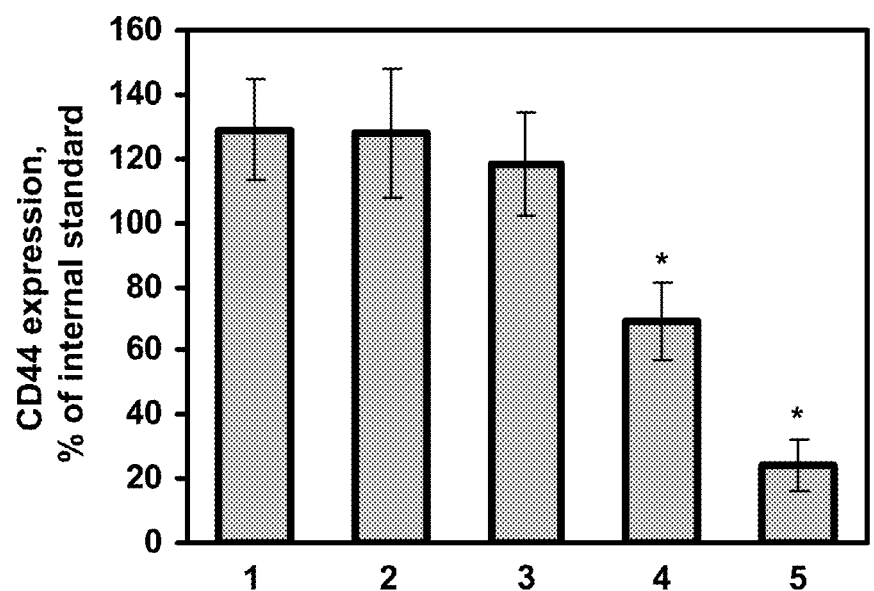

FIG. 21 shows suppression of CD44 mRNA (quantitative RT-PCR) in ascitic cells obtained from patients with metastatic ovarian cancer. Cells with incubated with the following substances: 1—Media (control); 2—Scrambled siRNA; 3—Naked CD44 siRNA; 4—CD44 siRNA delivered by non-targeted PPI dendrimer; 5—CD44 siRNA delivered by PPI dendrimer targeted to cancer cells by LHRH peptide. Means±SD are shown. P<0.05 when compared with control.

Figure 22:
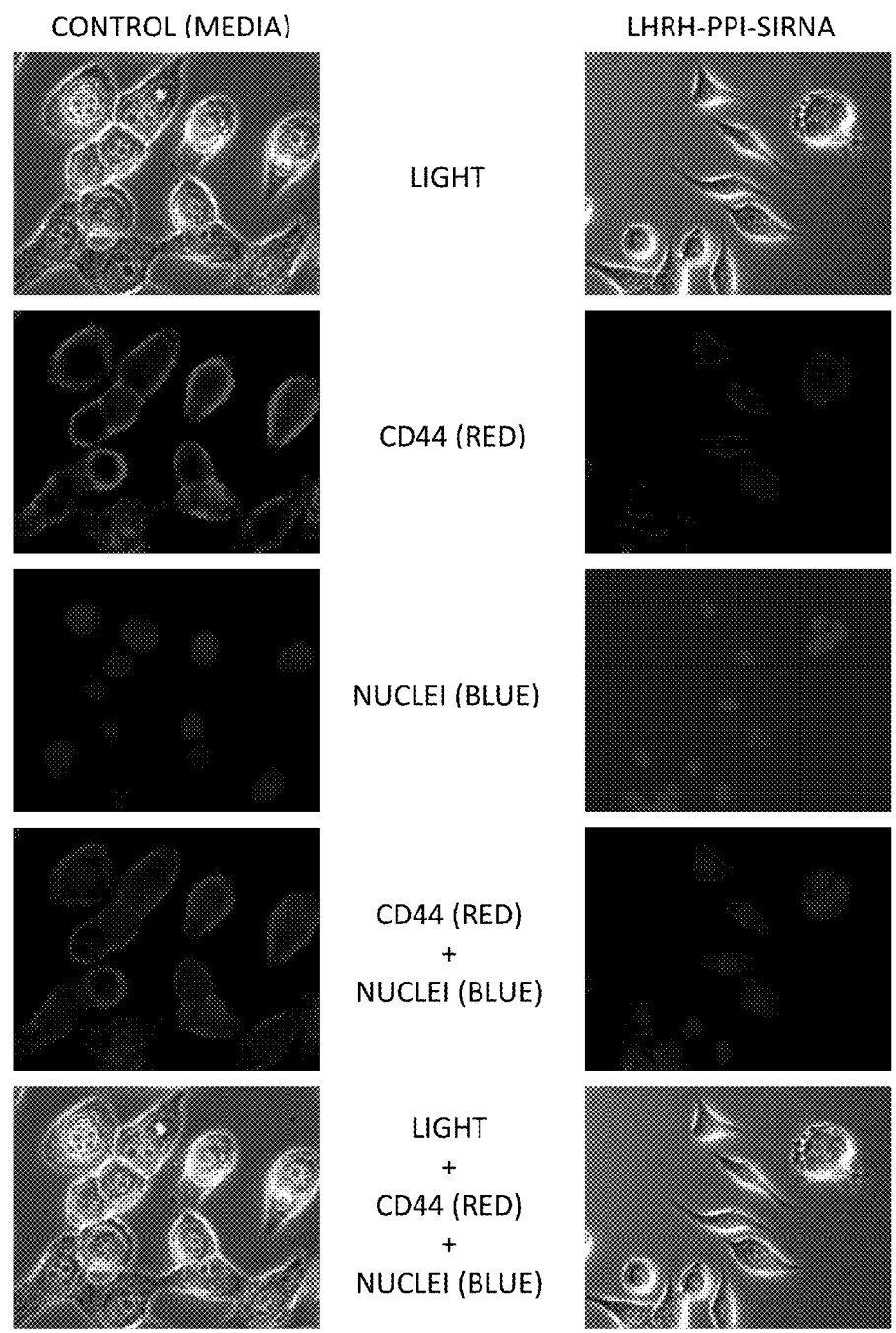

FIG. 22 shows the suppression of CD44 protein in ascitic cells obtained from patients with metastatic ovarian cancer. CD44 were suppressed by siRNA delivered with PPI dendrimer targeted to cancer cells by LHRH peptide. Representative light and fluorescence microscope images are shown.

Figure 23:
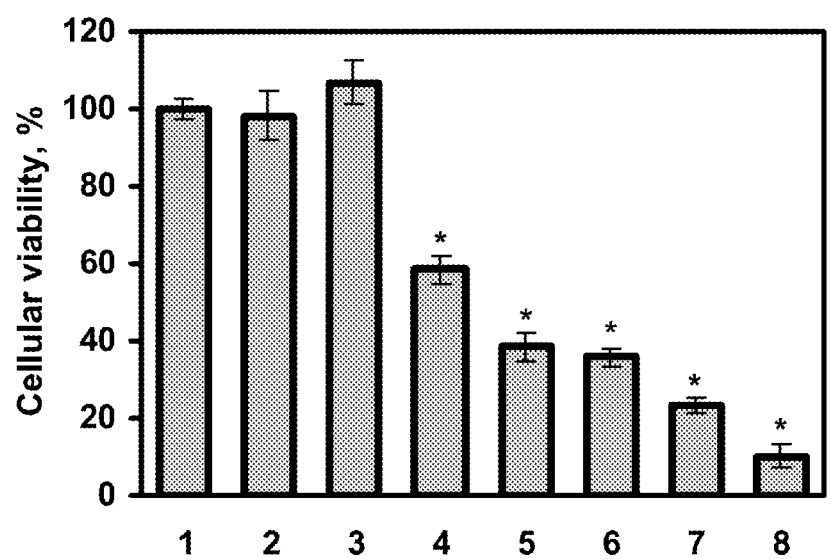

FIG. 23 shows the cytotoxicity of different formulations. Cells with incubated with the following substances: 1—Media (control); 2—Scrambled siRNA; 3—Naked CD44 siRNA; 4—Free paclitaxel; 5—CD44 siRNA delivered by non-targeted PPI dendrimer; 6—Paclitaxel delivered by non-targeted PPI dendrimer; 7—Paclitaxel and CD44 siRNA delivered by non-targeted PPI dendrimer; 8—Paclitaxel and CD44 siRNA delivered by PPI dendrimer targeted to cancer cells by LHRH peptide. Means±SD are shown. P<0.05 when compared with control.

FIG. 24 provides a schematic of the preparation of tumor-targeted, stable siRNA nanoparticles. (A) Cooperative condensation of siRNA with 5 nm SPIO nanoparticles and PPI G5 dendrimers. (B) PEGylation. (C) Conjugation of LHRH peptide to the distal end of the PEG layer.

Figure 25A:
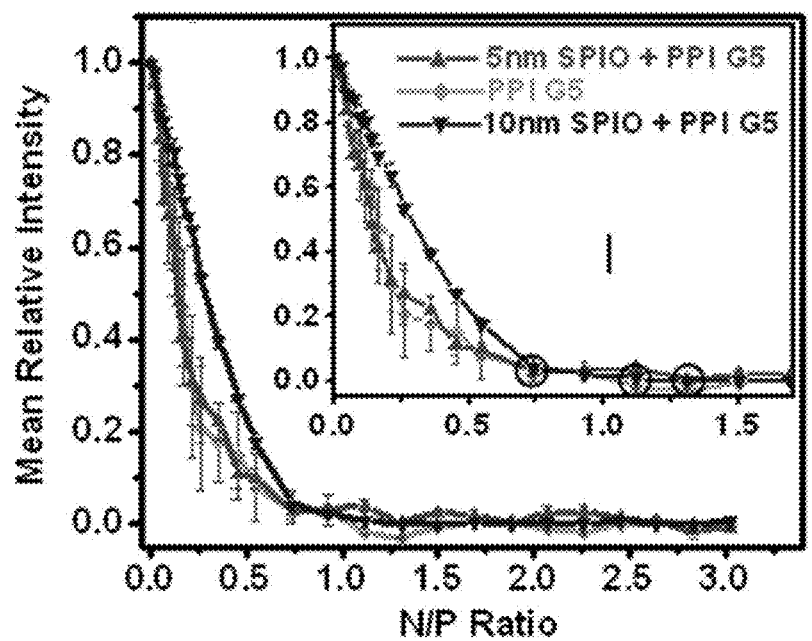
Figure 25B:
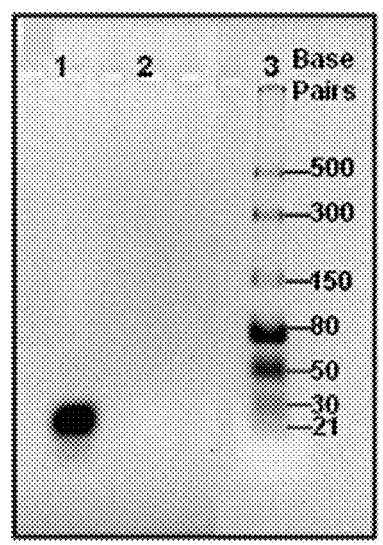

FIG. 25A shows siRNA complexation efficiency of SPIO nanoparticles and PPI G5 dendrimer evaluated by the ethidium bromide dye displacement assay. Figure inset shows enlarged portions of the curves in the vicinity of N/P ratios which represent the apparent ends of complexation. The circles in the enlarged curves highlight the N/P ratios corresponding to the apparent end of siRNA complexation by different complexation agents. Means±SD are shown. FIG. 25B provides a typical agarose gel electrophoresis image representing siRNA complexation efficiency by mixture of 5 nm SPIO nanoparticles and PPI G5. The gel was stained with ethidium bromide. (1) Free siRNA (control); (2) Mixture of 5 nm SPIO with PPI G5 and (3) Double stranded RNA ladder.

Figure 26A:
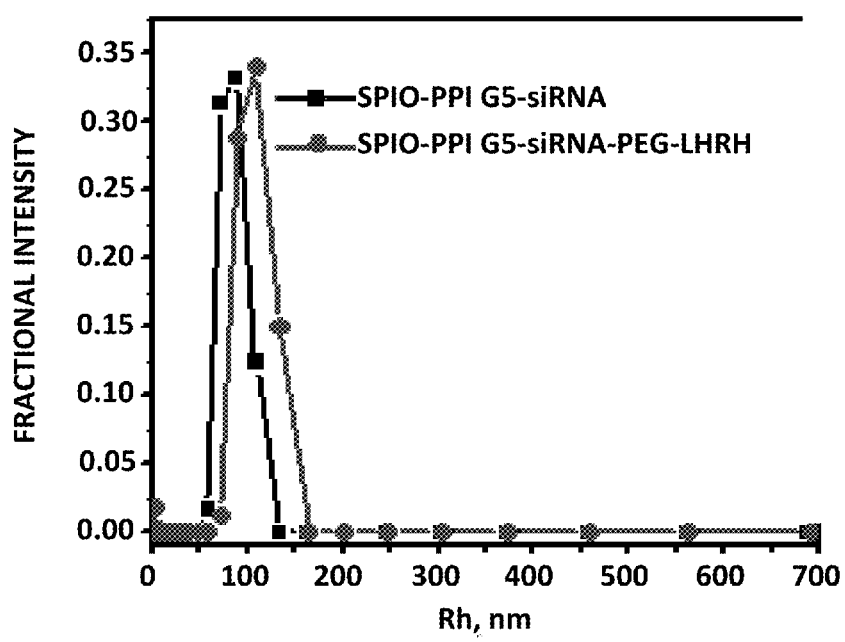
Figure 26B:
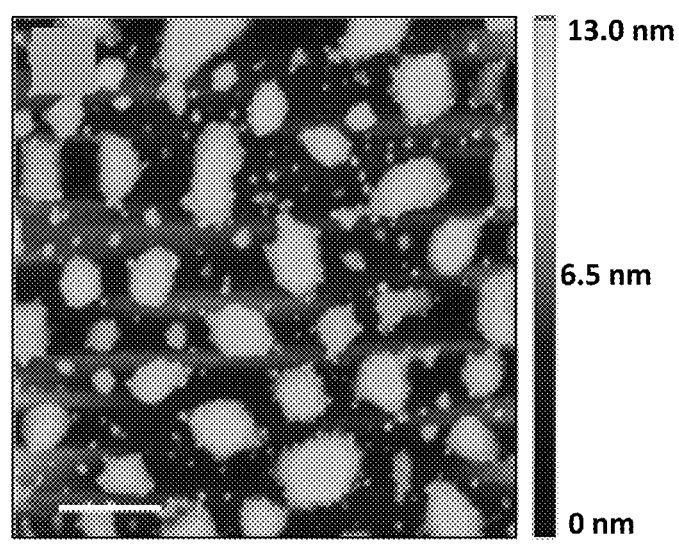

FIG. 26A provides representative curves of the size distribution of 5 nm SPIO-PPI G5-siRNA complexes prior and after modification with PEG and targeting LHRH peptide measured by DLS. Rh is hydrodynamic radius. FIG. 26B provides a representative atomic force microscope image of the nanoparticles formed as the result of siRNA complexation with mixture of SPIO and PPI G5. Scale bar is equal to 400 nm.

FIG. 27 provides representative fluorescence microscopic images of (FIG. 27A) SPIO-PPI G5-siRNA; (FIG. 27B) SPIO-PPI G5-siRNA-PEG and (FIGS. 27C, D) SPIO-PPI G5-siRNA-PEG-LHRH complexes after 24 hours of incubation with LHRH-positive A549 (FIGS. 27A-C) and LHRH-negative SKOV-3 (FIG. 27D) cancer cells. siRNA was labeled with 6-FAM.

Figure 28A:
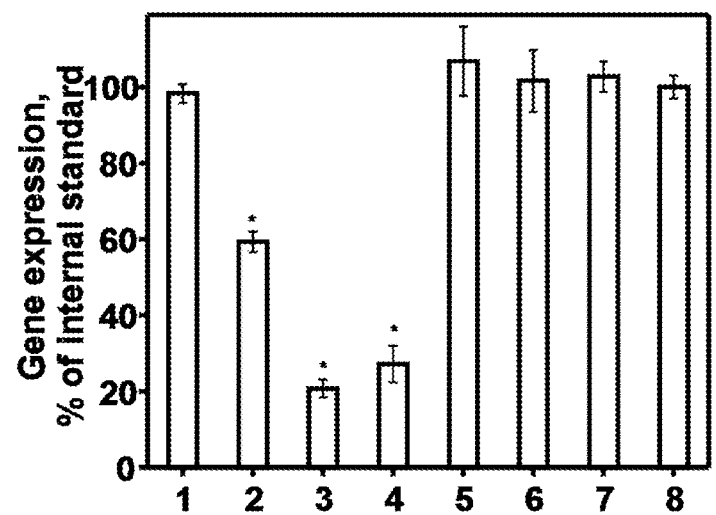
Figure 28B:
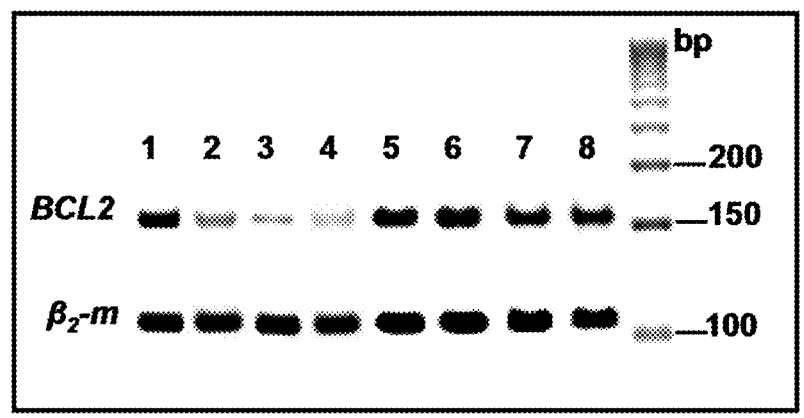

FIG. 28 provides a typical image of RT-PCR products and expression of the BCL2 gene in human A549 (1-6) and SKOV-3 (7, 8) cancer cells. A549 cells were treated with (1) medium (control); (2) SPIO-PPI G5-siRNA-PEG; (3) SPIO-PPI G5-siRNA; (4) SPIO-PPI G5-siRNA-PEG-LHRH; (5) SPIO-PPI G5; (6) SPIO-PPI G5-siRNA (scrambled). SKOV-3 cancer cells were treated with (7) SPIO-PPI G5-siRNA-PEG-LHRH and (8) medium (control). Gene expression was calculated as a ratio of band intensity of studied gene to that in internal standard (β2-m, β2-microglobulin). Means±SD are shown.

Figure 29A:
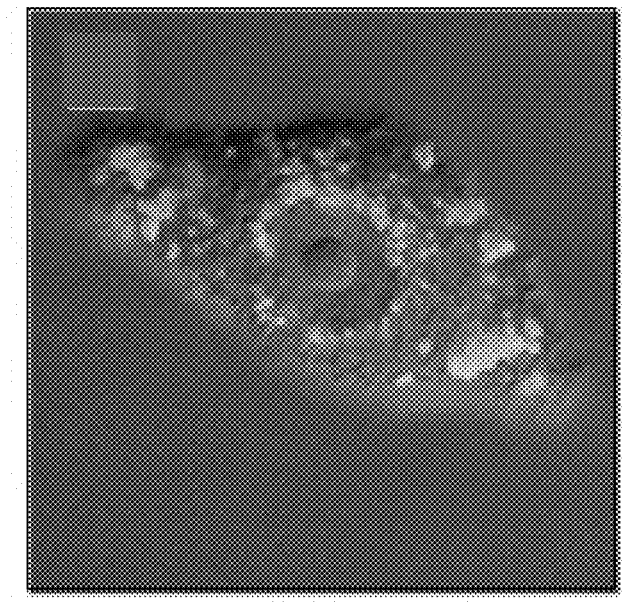
Figure 29B:
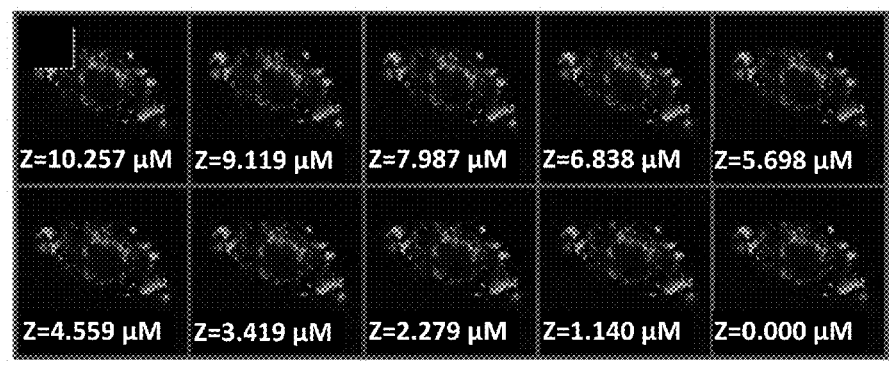

FIG. 29 provides representative confocal microscopy images (light+fluorescence) of A549 human cancer cells incubated for 24 hours with SPIO-PPI G5-siRNA-PEG-LHRH (FIG. 29A) and z-series from the top (z=10.257 μm) to the bottom (z=0 μm) of the single cell (FIG. 29B).

Figure 30A:
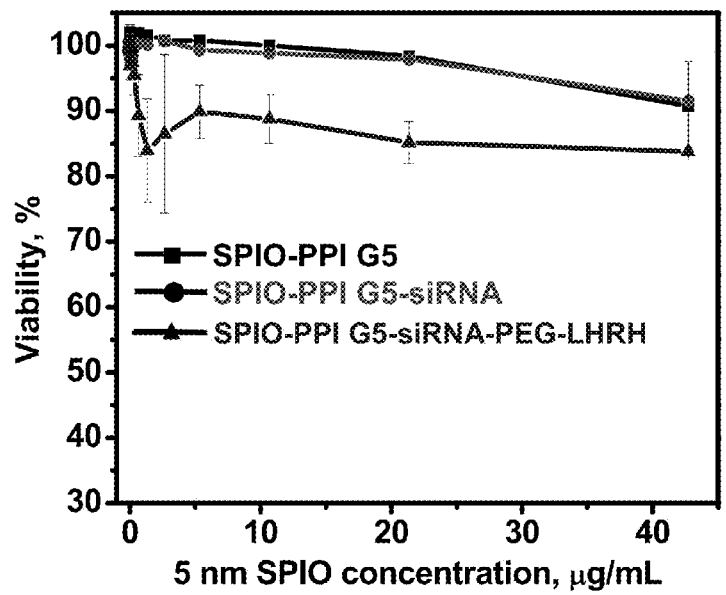
Figure 30B:
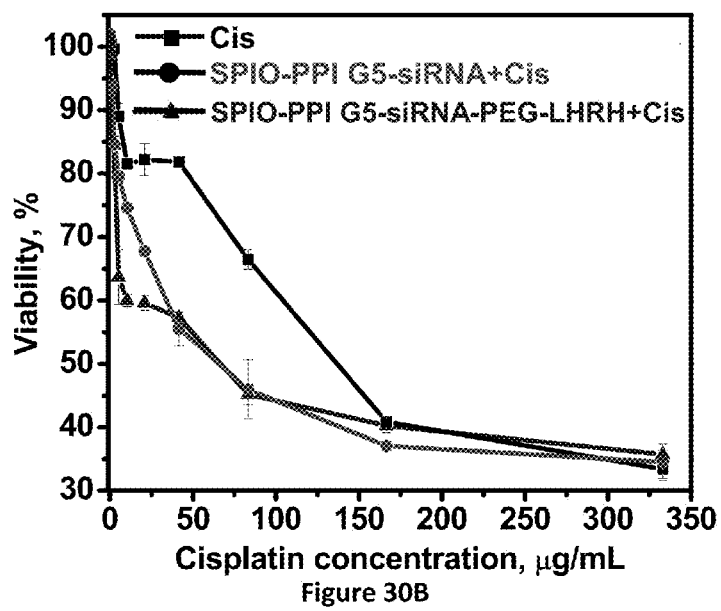

FIG. 30 shows the cytotoxicity of (FIG. 30A) SPIO-PPI G5; SPIO-PPI G5-siRNA; SPIO-PPI G5-siRNA-PEG-LHRH complexes and (FIG. 30B) Cisplatin; SPIO-PPI G5-siRNA+CIS; SPIO-PPI G5-siRNA-PEG-LHRH+CIS against A549 human cancer cells. Means±SD are shown.

Figure 31:
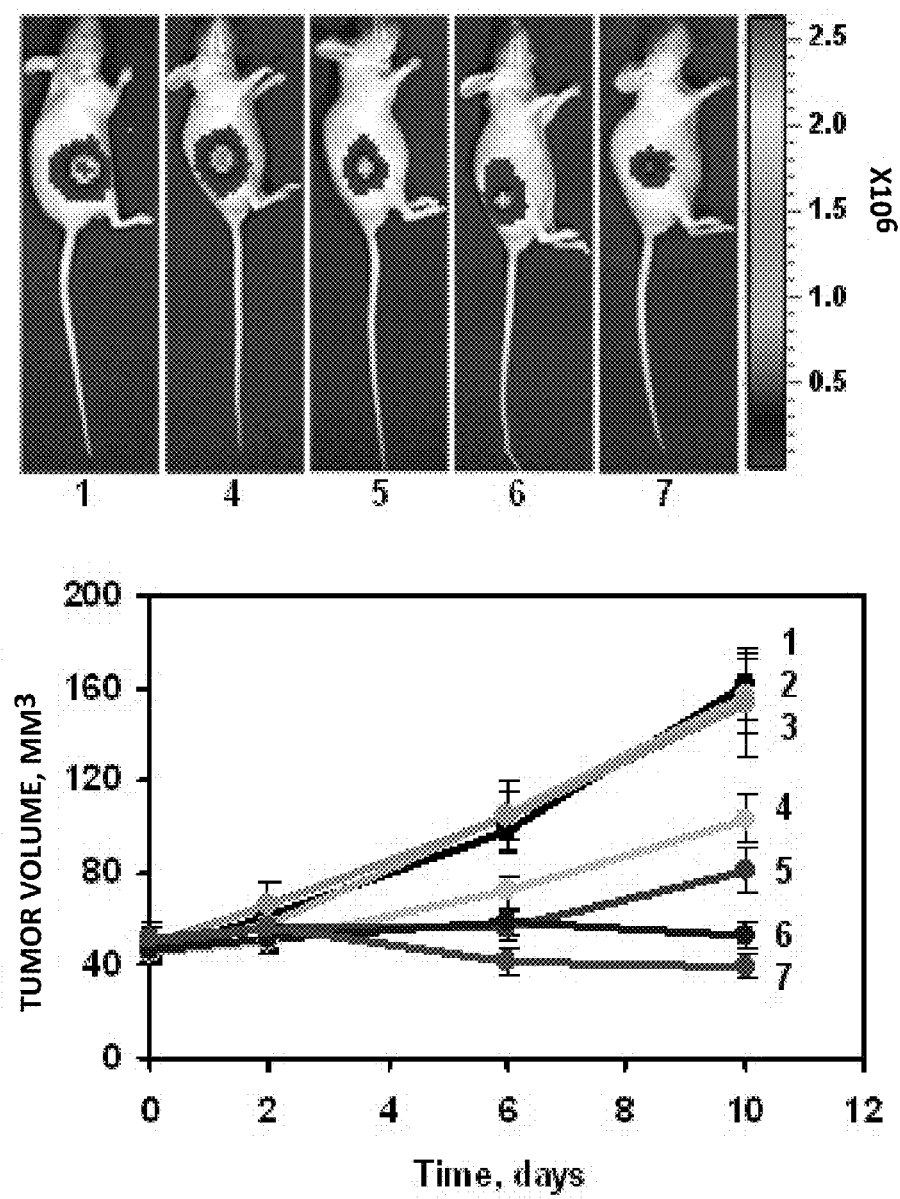

FIG. 31 shows the antitumor activity of different formulations. Upper panel: typical bioluminescent images of mice bearing subcutaneous tumor xenografts of human A549 cancer cells transfected with luciferase. Images were taken using the IVIS imaging system (Xenogen) in anesthetized animals at the end of the experiment. Bottom panel: Changes of tumor volume during the treatment. Mice were treated 3 times within 10 days with the following formulations: (1) Control (saline); (2) LHRH; (3) siRNA; (4) CIS; (5) SPIO-PPI-G5+CIS; (6) SPIO-PPI-G5-siRNA+CIS; (7) LHRH-PEG-SPIO-PPI-siRNA+CIS. Means±SD are shown.

DETAILED DESCRIPTION OF THE INVENTION

Drug resistance, metastases, and adverse side effects of chemotherapy are the major causes of treatment failure in ovarian cancer. To effectively circumvent multidrug resistance and prevent the development of metastases in ovarian cancer, a tumor-targeted complex delivery systems was constructed containing: (1) two anticancer drugs with different mechanisms of action (doxorubicin and cisplatin); (2) two antisense oligonucleotides (ASO)—suppressors of cellular drug resistance (one ASO targeting MDR1 and the other targeting BCL2 mRNA); and (3) a ligand specifically targeting LHRH receptors overexpressed in the plasma membrane of cancer cells. The tumor-targeted delivery system was tested in a mouse xenograft model of human ovarian cancer with intraperitoneal metastases and ascites, using tumors from patients with ovarian cancer. The proposed treatment not only led to the substantial regression of the growth of primary tumor, but also prevented the development of intraperitoneal metastases and limited adverse side effects of chemotherapy on healthy tissues.

The role of the poly(propyleneimine) (PPI) dendrimer structure on the siRNA nanoparticles formation, facilitation of cell internalization, and sequence specific knockdown of targeted genes was also evaluated herein. It was found that the higher generations of PPI dendrimers (G4 and G5) most effectively initiated the complexation of siRNA into discrete nanoparticles when compared with lower generations of dendrimers (G2 and G3) as determined by tapping mode atomic force microscopy and dynamic light scattering. The formulated siRNA-PPI dendrimer complexes provided for a dramatic enhancement in siRNA cellular internalization and the marked knockdown of targeted mRNA expression in A549 human lung cancer cells. While the size and positive charge density of G5 is much larger than G4 dendrimers, provoking higher toxicity, G4 dendrimer shows the maximum efficacy terms of siRNA nanoparticles formation, intracellular siRNA internalization, and sequence specific gene silencing.

In accordance with the instant invention, methods of treating, inhibiting, and/or preventing cancer (including, e.g., the inhibition or prevention of metastasis), particularly ovarian cancer, in a patient are provided. In a particular embodiment, the method comprises administering to the patient at least one chemotherapeutic agent, particularly at least two chemotherapeutic agents with different mechanisms of action, and at least one, particularly at least two inhibitors of cellular drug resistance. The agents may be administered within one or more liposomes and/or dendrimers. In a particular embodiment, siRNA molecules are delivered via dendrimers, particularly G4 or G5 PPI dendrimers. In yet another embodiment, the at least two chemotherapeutic agents are selected from the group consisting of doxorubicin, paclitaxel, and cisplatin, particularly doxorubicin and cisplatin. The inhibitors of cellular drug resistance may be pump resistance inhibitors (drug efflux pump inhibitors) and/or nonpump resistance inhibitors (see, e.g., Szakacs, et al. (1998) Pathol. Oncol. Res. 4:251-257; van Veen and Konings (1998) Biochem. Biophys. Acta 1365:31-36; Minko, et al. (2001) Dis. Manag. Clin. Outcomes 3:48-54; Hamaguchi, et al. (1993) Cancer Res. 53:5225-5232; Minko, et al. (1998) J. Controlled Rel. 54:223-233; Minko, et al. (1999) J. Controlled Rel. 59:133-148; Pakunlu, et al. (2003) Pharmaceut. Res. 20:351-359; Alahary, et al. (1998) JPET 286:419-428; Motomura, et al. (1998) Blood 91:3163-3171; Corrias and Tonini (1992) Anticancer Res. 12:1431-1438; Gross, et al. (1999) Genes Dev. 13:1899-1911; Reed (1999) J. Clin. Oncol. 17:2941-2953). In a particular embodiment, the inhibitor of pump resistance is an inhibitor of Multi-Drug Resistance 1 (MDR1) (e.g., siRNA or antisense) and the inhibitor of nonpump resistance is an inhibitor of BCL2 or CD44 (e.g., siRNA or antisense). The liposomes and/or dendrimers may further comprise at least one targeting ligand for a cancer marker (e.g., a cell surface marker expressed only on cancer cells or has increased expression on cancer cells compared to normal healthy cells). In another embodiment, the targeting ligand binds Luteinizing Hormone-Releasing Hormone (LHRH) receptor (e.g., an LHRH analog). Compositions comprising at least one of the above agents and at least one pharmaceutically acceptable carrier are also encompassed by the instant invention.

Methods of delivering a siRNA to a cell (in vitro or in vivo) are also provided herein. In a particular embodiment, the method comprises contacting cells with a complex comprising siRNA(s) and a nanocarrier, particularly a dendrimer. The nanocarrier may comprise further therapeutic agents, e.g., at least one chemotherapeutic agent. Compositions comprising the siRNA loaded nanocarrier (e.g., dendrimer (see, e.g., below)) and at least one pharmaceutically acceptable carrier are also encompassed by the instant invention. The dendrimers and compositions may be used to treat a disease or disorder (particularly cancer) by administering the dendrimer or composition to a patient in need thereof, wherein the siRNA is therapeutic for said disease or disorder.

In one embodiment, the siRNA delivery method comprises contacting cells with a complex comprising siRNA and a cationic dendrimer, particularly a poly(propyleneimine) (PPI) dendrimer (e.g., a G4 or G5 dendrimer). In a particular embodiment, the dendrimer is linked to a cancer targeting ligand (e.g., through a PEG linker).

In another embodiment, the siRNA delivery method comprises contacting cells with a complex comprising siRNA and a compound comprising a polyamidoamine (PAMAM) dendrimer, polyethylene glycol (PEG), and poly-L-lysine. In a particular embodiment, the PAMAM is linked to the PEG which is linked the poly-L-lysine. The PAMAM may be acetylated. In a particular embodiment, the PAMAM dendrimer is a G4 or G5 dendrimer. In a particular embodiment, the average molecular weight of the PEG is about 2000 to about 5000 Da, particularly about 3000 Da. In a particular embodiment, the average molecular weight of the poly-L-lysine is about 10,000 to about 20,000 Da, particularly about 12,000 Da. In a particular embodiment, the compound is linked to a cancer targeting ligand.

As stated hereinabove, the nanocarrier may comprise further therapeutic agents, e.g., at least one chemotherapeutic agent. For example, the nanocarriers may further comprise at least one of doxorubicin, cisplatin, paclitaxel, topotecan, and camptothecin.

The nanocarriers may also further comprise at least one imaging agent. The imaging agents may be compounds useful for optical imaging, magnetic resonance imaging (MRI), positron emission tomography (PET), computerized tomography (CT), gamma-scintigraphy imaging, and the like. Such agents are well-known to those of skill in the art. Imaging agents include, without limitation, radioisotope, isotopes, biotin and derivatives thereof, gold (e.g., nanoparticles), optical imaging agents (e.g., near IR dyes (e.g., IRDye 800CW) phorphyrins, anthraquinones, anthrapyrazoles, perylenequinones, xanthenes, cyanines, acridines, phenoxazines, phenothiazines and derivatives thereof), chromophore, fluorescent compounds (e.g., Alexa Fluor® 488, fluorescein, rhodamine, DiI, DiO, and derivatives thereif), MRI enhancing agents (for example, DOTA-Gd3+ (1,4,7,10-tetraazacyclododecane-1,4,7,10-tetra(acetic acid)), DTPA-Gd3+ (gadolinium complex with diethylenetriamine pentaacetic acid), etc.), paramagnetic or superparamagnetic ions (e.g., Gd(III), Eu(III), Dy(III), Pr(III), Pa(IV), Mn(II), Cr(III), Co(III), Fe(III), Cu(II), Ni(II), Ti(III), and V(IV)), PET compounds labeled or complexed with $^{11}$C, $^{13}$N, $^{15}$O, $^{18}$F, $^{64}$Cu, $^{68}$Ga, or $^{82}$Rb (e.g., $^{18}$F-FDG (fluorodeoxyglucose)), CT compounds (for example, iodine or barium containing compounds, e.g., 2,3,5-triiodobenzoic acid), and gamma or positron emitters (for example, $^{99m}$Tc, $^{111}$In, $^{113}$In, $^{153}$Sm, $^{123}$I, $^{131}$I $^{18}$F, $^{64}$Cu, $^{201}$Tl, etc.). In a particular embodiment, the imaging agent is an MRI contrast agent, particularly superparamagnetic iron oxide (SPIO).

A targeting ligand is a compound that will specifically bind to a specific type of tissue or cell type. The term "cancer marker" refers to biomolecules (e.g., proteins, carbohydrates, glycoproteins, and the like) that are exclusively or preferentially or differentially expressed on a cancer cell and thereby provide targets preferential or specific to the cancer. The preferential expression can be preferential expression as compared to any other cell in the organism or preferential expression within a particular area/organ/tissue of the organism. As used herein, the term "cancer targeting ligand" refers to a targeting ligand that specifically binds a cancer marker. A "cancer targeting ligand" may be an antibody immunologically specific for the cancer marker. For example, Her2 is a well known breast cancer marker. Trastuzumab is a monoclonal antibody which specifically binds the extracellular domain of HER2 and is a cancer targeting ligand. Epidermal growth factor receptor (EGFR) is also a well known cancer marker. In a particular embodiment of the instant invention, the cancer targeting ligand is specific for LHRH receptors (LHRHR). In a particular embodiment, the cancer targeting ligand is LHRH or an analog thereof (e.g., SEQ ID NO: 3). In a particular embodiment, the cancer targeting ligand is a CD44 antibody or fragment thereof.

Cancers that may be treated using the present invention (e.g., siRNA delivery vehicles) include, but are not limited to: cancers of the prostate, colorectum, pancreas, cervix, stomach, endometrium, brain, liver, bladder, ovary, testis, head, neck, skin (including melanoma and basal carcinoma), mesothelial lining, white blood cell (including lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, skin squamous cell carcinomas, and testicular seminoma. In a particular embodiment, the cancer is a gynecological cancer (e.g., cervical, ovarian, uterine, vaginal, and vulvar). In a particular embodiment, the cancer is ovarian cancer. In a particular embodiment, the compositions of the instant invention are co-administered with chemotherapy (e.g., radiation). The compositions of the instant invention may be administered before, after, and/or simultaneously with the other agents or therapy.

I. DEFINITIONS

The following definitions are provided to facilitate an understanding of the present invention:

The term "isolated" may refer to protein, nucleic acid, compound, or cell that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxilliary agent, filler, disintegrant, lubricating agent, binder, stabilizer, preservative or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "replicon" is any genetic element, for example, a plasmid, cosmid, bacmid, plastid, phage or virus, which is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

The terms "percent similarity", "percent identity" and "percent homology" when referring to a particular sequence are used as set forth in the University of Wisconsin GCG software program.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

Antisense molecules are oligonucleotides that hybridize under physiological conditions to a particular gene or to an mRNA transcript of such gene and, thereby, inhibit the transcription of such gene and/or the translation of such mRNA. The antisense molecules are designed so as to interfere with transcription or translation of a target gene upon hybridization with the target gene or its mRNA. Antisense molecules are typically between about 15 and about 30 nucleotides, but the exact length of the antisense oligonucleotide and its degree of complementarity with its target depend upon the specific target selected. An antisense oligonucleotide is preferably constructed to bind selectively with the target nucleic acid under physiological conditions. Antisense molecules may span the translational start site of mRNA molecules. Antisense constructs may also be generated which contain the entire gene sequence in reverse orientation. Antisense oligonucleotides targeted to any known nucleotide sequence can be prepared by oligonucleotide synthesis according to standard methods.

The term "siRNA" refers to small inhibitory RNA duplexes such as those that induce the RNA interference (RNAi) pathway. siRNA may vary in length, but are generally 12-30, more typically about 21 nucleotides in length (see Ausubel et al., eds., Current Protocols in Molecular Biology, John Wiley and Sons, Inc.). siRNA may have unpaired overhanging bases on the 5' or 3' end of the sense strand and/or the antisense strand. As used herein, the term "siRNA" includes duplexes of two separate strands and single strand molecules that can form hairpin structures comprising a duplex region (shRNA).

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning: A Laboratory Manual, Cold Spring Harbor Laboratory Press):

$$T_m = 81.5° C. + 16.6 \text{ Log } [Na+] + 0.41(\% G+C) - 0.63(\% \text{ formamide}) - 600/\#bp \text{ in duplex}$$

As an illustration of the above formula, using $[Na+] = [0.368]$ and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

Chemotherapeutic agents are compounds that exhibit anti-cancer activity and/or are detrimental to a cell (e.g., a toxin). Suitable chemotherapeutic agents include, but are not limited to (along with mechanism of action): toxins (e.g., saporin, ricin, abrin, ethidium bromide, diptheria toxin, Pseudomonas exotoxin); taxanes; alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators (e.g., mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-ANSA, doxorubicin, deoxyrubicin, etoposide, etopside phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); tubulin interactive agents (e.g., vincristine, vinblastine, and paclitaxel (Taxol)); hormonal agents (e.g., estrogens; conjugated estrogens; ethinyl estradiol; diethylstilbesterol; chlortrianisen; idenestrol; progestins such as hydroxyprogesterone caproate, medroxyprogesterone, and megestrol; and androgens such as testosterone, testosterone propionate, fluoxymesterone, and methyltestosterone); adrenal corticosteroids (e.g., prednisone, dexamethasone, methylprednisolone, and prednisolone); leutinizing hormone releasing agents or gonadotropin-releasing hormone antagonists (e.g., leuprolide acetate and goserelin acetate); and antihormonal antigens (e.g., tamoxifen, antiandrogen agents such as flutamide; and antiadrenal agents such as mitotane and aminoglutethimide).

II. ADMINISTRATION

The compositions described herein will generally be administered to a patient as a pharmaceutical preparation. The term "patient" as used herein refers to human or animal subjects. These compositions may be employed therapeutically, under the guidance of a physician.

The compositions of the instant invention may be conveniently formulated for administration with any pharmaceutically acceptable carrier(s). For example, the agents may be formulated with an acceptable medium such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

The dose and dosage regimen of compositions according to the invention that are suitable for administration to a particular patient may be determined by a physician considering the patient's age, sex, weight, general medical condition, and the specific condition for which the composition is being administered and the severity thereof. The physician may also take into account the route of administration, the pharmaceutical carrier, and the composition's biological activity.

Selection of a suitable pharmaceutical preparation will also depend upon the mode of administration chosen. For example, the compositions of the invention may be administered by direct injection to a desired site. In this instance, a pharmaceutical preparation comprises the agents dispersed in a medium that is compatible with the site of injection.

Compositions of the instant invention may be administered by any method. For example, the compositions of the instant invention can be administered, without limitation parenterally, subcutaneously, orally, topically, pulmonarily, rectally, vaginally, intravenously, intraperitoneally, intrathecally, intracerbrally, epidurally, intramuscularly, intradermally, or intracarotidly. In a particular embodiment, the compositions are administered intravenously or intraperitoneally. Pharmaceutical preparations for injection are known in the art. If injection is selected as a method for administering the composition, steps must be taken to ensure that sufficient amounts of the molecules reach their target cells to exert a biological effect.

Pharmaceutical compositions containing an agent of the present invention as the active ingredient in intimate admixture with a pharmaceutically acceptable carrier can be prepared according to conventional pharmaceutical compounding techniques. The carrier may take a wide variety of forms depending on the form of preparation desired for administration, e.g., intravenous, oral, direct injection, intracranial, and intravitreal.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

In accordance with the present invention, the appropriate dosage unit for the administration of compositions of the instant invention may be determined by evaluating the toxicity of the molecules or cells in animal models. Various concentrations of agents in pharmaceutical preparations may be administered to mice, and the minimal and maximal dosages may be determined based on the beneficial results and side effects observed as a result of the treatment. Appropriate dosage unit may also be determined by assessing the efficacy of the agent treatment in combination with other standard drugs. The dosage units of the compositions may be determined individually or in combination with each treatment according to the effect detected.

The pharmaceutical preparation comprising the agents of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

The instant invention encompasses methods of treating a disease/disorder comprising administering to a subject in need thereof a composition comprising an agent of the instant invention and, preferably, at least one pharmaceutically acceptable carrier. In a particular embodiment, the disease is cancer, particularly ovarian cancer. Other methods of treating the disease or disorder may be combined with the methods of the instant invention (e.g., other chemotherapeutic agents or therapy (e.g., radiation)) may be co-administered with the compositions of the instant invention.

The following examples provide illustrative methods of practicing the instant invention, and are not intended to limit the scope of the invention in any way.

Example 1

A tumor-targeted liposomal drug delivery system (DDS) was constructed containing doxorubicin (DOX) or cisplatin (CIS) as anticancer drugs, a synthetic analog of Luteinizing Hormone-Releasing Hormone (LHRH) as tumor targeting moiety, and Antisense Oligonucleotides (ASO) targeted to MDR1 and BCL2 mRNA as suppressors of pump and non-pump resistance, respectively. The DDS was tested in a mouse xenograft model of human metastatic ovarian cancer with intraperitoneal metastases. Primary tumors were developed by subcutaneous injection of cancer cells isolated from fresh malignant ascites of patients with advanced ovarian carcinoma.

Materials and Methods
Materials

Egg phosphatidylcholin (EPC), Cholesterol (Chol), and 1,2,-distearoyl-sn-glycero-3-phosphoethanolamine-N-aminopolyethelenglycol-Mw-2000 ammonium salt (DSPE-PEG) were purchased from Avanti Polar Lipids (Alabaster, Ala.); P-ethoxy modified antisense oligonucleotides targeted to MDR1 (5'-TTC AAG ATC CAT CCC GAC CTC GCG-3'; SEQ ID NO: 1) and BCL2 (5'-CAG CGT GCG CCA TCC TTC CC-3'; SEQ ID NO: 2) mRNA were synthesized as described (Pakunlu, et al. (2003) Pharm. Res., 20:351-359; Pakunlu et al. (2004) Cancer Res., 64:6214-6224; Pakunlu et al. (2006) J. Control. Rel., 114:153-162) by Oligos Etc. (Wilson, Oreg.); cisplatin and doxorubicin were purchased from Sigma (St. Louis, Mo.). A synthetic analog of LHRH, Lys6-des-Gly10-Pro9-ethylamide (Gln-His-Trp-Ser-Tyr-DLys-Leu-Arg-Pro-NH-Et; SEQ ID NO: 3) was synthesized as described (Chandna et al. (2007) Mol. Pharm., 4:668-678; Dharap et al. (2005) Proc. Natl. Acad. Sci., 102:12962-12967; Pakunlu et al. (2006) J. Control. Rel., 114:153-162; Dharap et al. (2003) J. Control. Rel., 91:61-73; Garbuzenko et al. (2009) Pharm. Res., 26:382-394; Khandare et al. (2006) J. Pharmacol. Exp. Ther., 317:929-937; Saad et al. (2008) J. Control. Rel., 130:107-114) by American Peptide (Sunnyvale, Calif.). For in vitro experiments, LHRH peptide was labeled by Rhodamine (Invitrogen Molecular Probs, Carlsbad, Calif.) as previously described (Khandare et al. (2006) J. Pharmacol. Exp. Ther., 317:929-937).

Drug Formulations

PEGylated "neutral" liposomes were prepared as previously described using lipids (EPC, Cholesterol, and DSPE-PEG in ratio 51:44:5, respectively) (Pakunlu et al. (2006) J. Control Release 114:153-162; Garbuzenko et al. (2009) Pharm. Res., 26:382-394). To prepare tumor-targeted liposomes, DSPE-PEG was conjugated with LHRH peptide as previously described (Saad et al. (2008) J. Control. Release 130:107-114) and added together with regular DSPE-PEG. To prepare CIS loaded liposomes, thin film layer was rehydrated in 0.9% NaCl containing 2 mg/ml of CIS. It is known that both siRNA and ASO can be effectively used for the suppression of targeted genes and proteins (Betigeri et al. (2006) Mol. Pharm. 3:424-430). "Neutral" liposomes cannot be used for the effective delivery of negatively charged siRNA. The delivery of siRNA requires cationic liposomes. However, cationic liposomes are not the best choice for the delivery of DOX. To use "neutral" liposomes as a delivery vehicle for drugs and nucleic acids, a modified "neutral" form of ASO was used. Unfortunately, it is not possible to neutralize the charge of siRNA without substantial decrease in their activity. ASO targeted to BCL2 and MDR1 mRNA were dissolved in 0.9% NaCl in concentrations at 0.25 mM of each ASO (Pakunlu et al. (2006) J. Control Release 114:153-162). To prepare DOX loaded liposomes, the thin film layer was rehydrated with 300 mM citrate buffer (pH=4) followed by overnight dialysis against 0.9% NaCl at 4° C., and incubated with DOX solution (5 mg/ml) at 37° C. for 40 minutes (Garbuzenko et al. (2009) Pharm. Res., 26:382-394). In most cases, DOX-loaded liposomes preparation is based on transmembrane ammonium ion gradient. The other way to create transmembrane gradient includes the use of two buffers with different pH for internal and external liposomal areas. Citric acid buffer, 300 mM with the pH and 0.9% (150 mM) NaCl with pH ~5.5, was used, respectively (Wasserman et al. (2007) Langmuir 23:1937-1947). The choice was based on the following consideration. Liposomes were passively loaded with ASO which should have been dissolved in the rehydration buffer and mixed with the lipids. The preliminary data showed that citric acid buffer with pH 4 was more effective and safe for loading of ASO when compared with $NH_4CL$ solution. Before loading, DOX was dissolved in double distilled water. Liposomes were separated from free drugs and ASO by overnight dialysis against 0.9% NaCl. The aliquots of liposomes were destroyed in isopropanol in a ratio of 10:90 (liposomes:isopropanol) and the concentration of trapped DOX was determined by high-performance liquid chromatography using a symmetry C18 column (150 mm×4.6 mm, Waters Corporation, Milford, Mass., USA) operated at room temperature. The mobile phase consisted of 0.1% trifluoroacetic acid in water/acetonitrile 25:75 v:v; the flow rate was set to 1.0 ml/min, wavelength 480 nm. The chromatographic instillation consisted of a Model 1525 pump (Waters Corporation, Milford, Mass., USA), a Model 717 Plus auto-injector (Waters Corporation) and a Model 2487 variable wavelength UV detector (Waters Corporation) connected to the Millennium software. Loading efficacy of DOX was about 90% from total amount. The size of liposomes was measured by dynamic light scattering using 90Plus Particle Size Analyzer (Brookhaven Instruments, New York, N.Y.). The average size of EPC/Cholesterol/DSPE-PEG liposomes loaded with drugs and ASO was 130±10 nm. Electrical charge of liposomes was measured using ZetaPALS Zeta Potential Analyzer (Brookhaven Instruments, New York, N.Y.). The average zeta potential of empty and loaded PEGylated liposomes was −10±2 mV.

Cancer Cells

Discarded de-identified pathological materials obtained from the Cancer Institute of New Jersey were used to isolate cancer cells from tissues obtained from patients with ovarian carcinoma. The ascites fluid with cancer cells was obtained from the peritoneal area of patients with ovarian cancer. The samples were centrifuged for 20 minutes at 2000 g; the supernatant was discarded and cell pellets were consequently resuspended. The resuspended cells were cultured in RPMI media (Sigma, St. Louis, Mo.) supplemented with fetal bovine serum (Fisher Chemicals, Fairlawn, N.J.), 2.5 µg/ml insulin and 1.2 ml/100 ml penicillin-streptomycin (Sigma, St. Louis, Mo.).

Generation of Ascites Cells Stably Expressing Luciferase

In order to visualize cells and document tumor growth, ascitic cells were transfected with luciferase or green fluorescent protein. Briefly, cells were transfected for 24 hours in a 6-well plate with 2.0 µg of pMetLuc-Control vector (Clontech, Mountain View, Calif.) containing the neomycin resistance gene using Lipofectamine™ 2000 (Invitrogen, Carlsbad, Calif.) for luciferase or pAcGFP1-C1 vector (Clontech, Mountain View, Calif.) for green fluorescent protein according to the manufacture's recommendations. Cells were maintained in media containing 500 µg/ml G418 (Gibco, Grand Island, N.Y.) for further study. Cells were grown at 37° C. in a humidified atmosphere of 5% $CO_2$ (v/v) in air. All experiments were performed on cells in the exponential growth phase.

Animal Model and In Vivo Antitumor Activity

An animal model of human ovarian carcinoma xenografts was created as previously described (Chandna et al. (2007) Mol. Pharm., 4:668-678; Dharap et al. (2005) Proc. Natl. Acad. Sci., 102:12962-12967; Chandna et al. (2010) Pharm. Res.; Pakunlu et al. (2006) J. Control. Rel., 114:153-162; Saad et al. (2008) J. Control. Rel., 130, 107-114; Dharap et al. (2006) J. Pharmacol. Exp. Ther., 316:992-998; Minko et al. (2000) Int. J. Cancer, 86:108-117; Minko et al. (2000) Pharm. Res., 17:505-514; Wang et al. (2008) Clin. Cancer Res., 14:3607-3616). Briefly, human ascitic cells ($2 \times 10^6$) were subcutaneously transplanted into the flanks of female athymic nu/nu mice (NCRNU-M, CrTac:NCr-Foxn1$^{nu}$, Taconic Farms, Inc, Cranbury, N.J.). All mice received cancer cells from the same patient. When the tumors reached a size of about 0.3 cm$^3$ (15-20 days after transplantation), mice were treated intraperitoneally with the following formulations: (1) Saline (untreated control); (2) Liposomes (Lip); (3) LHRH; (4) DOX; (5) Lip-DOX; (6) Lip-DOX-BCL2 ASO; (7) Lip-DOX-MDR1 ASO; (8) Lip-DOX-BCL2-MDR1 ASO; (9) LHRH-Lip-DOX-BCL2-MDR1 ASO; (10) CIS; (11) Lip-CIS; (12) Lip-CIS-BCL2 ASO; (13) Lip-CIS-MDR1 ASO; (14) Lip-CIS-BCL2-MDR1 ASO; (15) LHRH-Lip-CIS-BCL2-MDR1 ASO; (16) DOX+CIS; (17) Lip-DOX+Lip-CIS; (18) Lip-DOX-BCL2 ASO+Lip-CIS-BCL2 ASO; (19) Lip-DOX-MDR1 ASO+Lip-CIS-MDR1 ASO; (20) Lip-DOX-BCL2-MDR1 ASO+Lip-CIS-BCL2-MDR1 ASO; (21) LHRH-Lip-DOX-BCL2-MDR1 ASO+LHRH-Lip-CIS-BCL2-MDR1 ASO. The doses of DOX (2.5 mg/kg) and CIS (2.5 mg/kg) in formulations corresponded to the maximum tolerated dose of these drugs. The maximum tolerated doses were estimated in separate experiments based on the animal weight change after the injection of increasing doses of drugs as previously described (Chandna et al. (2007) Mol. Pharm., 4:668-678; Dharap et al. (2005) Proc. Natl. Acad. Sci., 102: 12962-12967; Khandare et al. (2006) J. Pharmacol. Exp. Ther., 317:929-937; Dharap et al. (2006) J. Pharmacol. Exp. Ther., 316:992-998). The animals were treated maximum 8 times over four weeks and the development of primary tumor and intraperitoneal metastases was monitored by fluorescent IVIS (Xenogen, Alameda, Calif.) and ultrasound Vevo 2100 (VisualSonics, Toronto, Canada) imaging systems. To initiate bioluminescence of cancer cells, 1× substrate/reaction buffer (Clontech, Mountain View, Calif.) was diluted 1:20 with DPBS and 100 µl of the solution was injected into each mouse. The bioluminescent images were taken 10 minutes after the injection of the substrate. The size of primary tumor was measured by a caliper. At the end of the experiments, tumors and ascites were excised and their mass was measured. Animal weight was evaluated every day during the treatment period. Changes in tumor size were used as an overall marker for antitumor activity. According to the protocol approved by the Rutgers University Animal Care and Facilities Committee, animals were euthanized when tumor volume reached approximately 2,000 mm$^3$ (about 10% of body weight) or when body weight significantly changed when compared with the control untreated group.

Expression of Targeted Genes and Proteins

The expression of MDR1 and BCL2 genes was measured using a quantitative RT-PCR as previously described (Pakunlu et al. (2006) J. Control. Rel., 114:153-162). Gene expression was calculated as a percent of internal standard ($\beta_2$-microglobulin). To identify the presence of BCL2, P-glycoprotein and Caspase 3 (CASP3) proteins, the immunohistochemical staining of paraffin-embedded tumor tissue slides was carried out. For BCL2 and CASP3, slides were deparaffinized in xylene for 5 min followed by progressive rehydration in 100%, 95%, 70% and 50% ethanol for 3 minutes during each step. Endogenous peroxidase activity was blocked by incubating slides in 3% $H_2O_2$ solution in methanol at room temperature for 10 minutes and washing in 300 ml PBS two times for 5 minutes. Slides then were stained with anti-mouse monoclonal antibodies for BCL2 conjugated with FITC (1:200 dilution; BioLegend, catalog number 633502, San Diego, Calif.) and for CASP3 conjugated with Alexa Flour 647 (1:200 dilution; BioLegend, catalog number 622702, San Diego, Calif.) by incubating for an hour, washed in 300 ml PBS two times for 5 minutes and analyzed by fluorescence microscopy. To identify the expression of P-glycoprotein, after deparaffinization and rehydration, the slides were stained using Vector® M.O.M. Immunodetection Kit (Vector Laboratories, Inc., Burlingame, Calif.). Mouse monoclonal antibody to P-glycoprotein (ab3366, 1:40 dilution) obtained from Abcam (Cambridge, Mass.) was used as primary antibody for the detection of P-glycoprotein. Biotinylated anti-mouse IgG Reagent (1:250 dilution, Vector Laboratories, Inc., Burlingame, Calif.) and HSP-Streptavidine Detection System (1:500 dilution, Vector Laboratories, Inc., Burlingame, Calif.) in combination with DAB substrate kit (Vector Laboratories, Inc., Burlingame, Calif.) for peroxidase were used for visualization. After staining, the slides were examined by light microscopy and photographed.

Histopathologic Analysis

After sacrificing an animal, the tumors and organs were extracted and immediately fixed in 10% phosphate-buffered formalin. Samples were subsequently dehydrated and embedded in Paraplast®. Five-micrometer sections were cut and stained with hematoxylin-eosin as previously described (Lu et al. (2006) Cancer Res., 66:11494-11501) and analyzed.

Apoptosis

Induction of apoptosis was analyzed by the measurement of the enrichment of histone-associated DNA fragments (mono- and oligo-nucleosomes) in homogenates of the tumor, malignant ascites and other organs (liver, kidney, lung, heart and brain) using anti-histone and anti-DNA antibodies by a cell death detection ELISA Plus kit (Roche, Nutley, N.J.) as previously described (Pakunlu et al. (2004) Cancer Res., 64:6214-6224; Dharap et al. (2005) Proc. Natl. Acad. Sci., 102:12962-12967; Dharap et al. (2003) Pharm. Res., 20:889-896).

Statistical Analysis

Data obtained were analyzed using descriptive statistics, single factor analysis of variance (ANOVA) and presented as a mean value±standard deviation (SD) from ten independent measurements. Data sets were analyzed for significance with Student's t test and considered P value of less than 0.05 as statistical significant.

Results

Development of Primary Solid Tumors and Intraperitoneal Metastases

To create a mouse model of human ovarian carcinoma, cells isolated from human malignant ascites obtained from patients with advanced ovarian cancer were transfected with luciferase or green fluorescent protein (FIG. 1A) and subcutaneously injected in the flank of nude mice (FIG. 1B). Transfection of cancer cells with luciferase allowed for their visualization in live anesthetized animals using a bioluminescence IVIS imaging system. In untreated animals, the growth of primary solid subcutaneous tumors in 80% of animals was accompanied by the development of malignant intraperitoneal ascites and carcinomatosis (FIG. 1C). In addition to bioluminescence visualization, the existence of intraperitoneal metastases and malignant ascites was also confirmed in live animals using ultrasound Vevo imaging system (FIGS. 1D and 1F).

To deliver anticancer drugs specifically to tumor cells, the LHRH peptide was used as a targeting moiety. LHRH receptors (LHRHR) are overexpressed in many types of cancer cells and are not expressed in a detectable level in visceral organs (FIG. 1H). Although the expression of these receptors was found in tissues of healthy non-tumorous reproductive organs, the expression of LHRHR in tumor cells was significantly higher when compared with corresponding healthy tissue taken from the same organ of the same patient (FIG. 1I). To determine whether LHRHR are overexpressed in cells isolated from human malignant ascites, ascitic cells were incubated with LHRH peptide labeled with Rhodamine and registered its fluorescence by fluorescence microscopy. The fluorescence of labeled LHRH peptide was observed predominantly in the plasma membrane of cancer cells (FIG. 1E) where LHRH receptors are localized. In addition, the expression of mRNA encoded LHRHR was measured in cells isolated from human malignant ascites and found that these receptors were overexpressed in malignant ascites (FIG. 1G). Consequently, LHRH peptide can be used for targeting cancer cells in both primary tumors and intraperitoneal metastases. A complex tumor-targeted proapoptotic drug delivery system was constructed that contained PEGylated liposomes as carriers, LHRH peptides conjugated to distal ends of PEG polymers as targeting moieties, CIS or DOX as anticancer drugs-cell death inducers, and MDR1 and BCL2 antisense oligonucleotides (ASO) as suppressors of pump and nonpump cellular resistance, respectively (FIG. 1J). CIS, as a substance with low aqueous solubility, was located in the phospholipid bilayer of the liposomal membrane, while water-soluble DOX and P-ethoxy-modified electrically neutral ASO were located in the inner aqueous space of neutral liposomes. This complex delivery system with appropriate controls was used in the following experiments to treat tumor in an experimental animal model of ovarian carcinoma.

Histology of Tumor and Malignant Ascites

Solid primary tumors developed from cells obtained from patients with malignant ascites demonstrated at least three distinct histological types (FIG. 2, left panel). The predominant type consisted of solid sheets and nests of markedly pleomorphic, undifferentiated tumor cells with large, irregular nuclei and 1-2 prominent basophilic nucleoli. The cytoplasm was lightly eosinophilic and cell margins were not identifiable. The tumor cells displayed numerous mitotic figures, many of which were atypical. Multinucleated tumor giant cells were common. The margins of the tumor nests were surrounded by fine fibrovascular connective tissue. The second distinct histological type, occupying approximately 30% of the tumor, consisted of ribbons and nests of well-differentiated tumor cells forming identifiable glands. The epithelium of the glands was columnar, usually with a single row of circular to elongated nuclei. The nuclei were moderately pleomorphic and clear, with one or more nucleoli. The glandular element showed a high level of mitotic activity. The third tumor type consisted of aggregates of extremely large, pleomorphic cells with multiple large basophilic nuclei. Many of these cells contain abundant, brightly eosinophilic cytoplasm. The cytoplasm ranged in consistency from dense to vacuolated. This phase of the tumor is primarily localized to the margins of the tumor mass, adjacent to the skeletal muscle and may represent a degenerative stage of the cancer. There were suggestions of squamous differentiation, including cytokeratin and keratin pearls. Infrequent psammoma bodies were identified diffusely within the tumor mass. Psammoma bodies are predominately seen in ovarian serous adenocarcinomas (Pantanowitz et al. (2009) Acta Cytol., 53:263-267; Hiromura et al. (2007) J. Comput. Assist. Tomogr., 31:490-492; Okada et al. (2005) J. Nippon Med. Sch., 72:29-33).

Histologically untreated intraperitoneal metastases consisted of numerous spherical tumor nodules adherent to white adipose tissue (FIG. 2, middle panel). The nodules were comprised primarily of poorly differentiated cancer cells, some displaying several squamous characteristics. These cells were eosinophilic, round to polygonal in shape, and demonstrated considerable nuclear pleomorphism and a high mitotic rate. Many of the mitotic figures were atypical, with tripolar or tetrapolar divisions easily identified. In discrete regions, the cell membrane showed distinct "prickle" attachments characteristic of squamous differentiation. The tumor cell nuclei were large and showed variable amounts of heterochromatin and 1-3 basophilic nucleoli. At the center of some tumor nodules were cystic spaces containing a fibrovascular core. The tumor nodules were enclosed by a layer of flattened to cuboidal epithelial cells. The flattened cells showed clear squamous differentiation, while the cuboidal cells were without discernable lineage differentiation. The fat to which the nodules were attached was focally infiltrated with polymorphonuclear neutrophilic leukocytes and lymphocytes.

Histological analysis showed that mice with subcutaneous tumors treated with combination of two DDS (LHRH-Lip-DOX-BCL2-MDR1 ASO and LHRH-Lip-CIS-BCL2-MDR1 ASO) underwent both apoptosis and necrosis (FIG. 2, right panel). Many of the tumor nests displayed central necrosis and glassy-eosinophilic cytoplasmic swelling. Clusters of brightly eosinophilic tumor cells were noted; these contained ample, swollen and degenerating cytoplasm with well-developed zones of tumor necrosis. Treated tumor nodules consisted of necrotic tumor tissues and showed a fibroblastic reparative response. The majority of the nodules contained 'ghosts' of dead tumor cells, hyalinized connective tissue, and a mild mixed inflammatory response. Only rare viable malignant cells were identified within the nodules, and these were represented by single or small clusters of cells, some of which are undergoing degeneration. The degree of tumor killing was >99% of the cells. Macrophages containing a granular, light gold material were present within the dead tumor mass and abundantly within the lymph node. No ascites development was registered in mice with primary tumor treated with the aforementioned combination of DDS.

Expression of Targeted Genes and Proteins

Analysis of in vivo expression of targeted genes responsible for cellular drug resistance showed that empty liposomes and LHRH peptide alone (controls) did not change significantly the expression of both MDR1 and BCL2 genes (FIGS. 3A and 3B, bars 1-3). Treatment of mice bearing xenografts of human malignant ascites with free DOX, CIS and their combination led to statistically significant overexpression of both genes (FIGS. 3A and 3B, bars 4, 10, 16). Liposomal formulations of DOX and CIS induced overexpression of BCL2 mRNA (FIG. 3B, bars 5, 11, 17). However, the delivery of drugs as liposomal formulations led to the decrease in the expression of the MDR1 mRNA when compared with free drugs (FIG. 3A, compare bars 4 and 5, 10 and 11, 16 and 17). Simultaneous delivery of anticancer drugs with ASO targeted to MDR1 mRNA decreased the expression of the MDR1 gene (FIG. 3A, bars 7-9, 13-15, 19-21). Similarly, simultaneous delivery of anticancer drugs with ASO targeted to BCL2 mRNA decreased the expression of the BCL2 gene (FIG. 3B, bars 6, 8, 9, 12, 14, 15, 18, 20, 21). Direct measurement of the expression of corresponding proteins (FIG. 4) supports the results of gene expression analysis. In fact, the expression of P-glycoprotein (encoded by the MDR1 gene) and BCL2 protein in xenografts of human ovarian cancers was increased after the treatment of mice with free and liposomal forms of the drugs (FIG. 4, panels a-b, #2-5), while incorporation of ASO into the liposomal delivery system suppressed these proteins (FIG. 4, panels a-b, #6-10). It should be stressed that targeting of liposomal DDS to tumor cells by LHRH peptide led to a more complete suppression of the expression of both P-glycoprotein and BCL2 (FIG. 4, compare #8-10 with #6-7 on panels a-b).

Apoptosis Induction

Apoptosis induction was studied in tumor, malignant ascites, and healthy organs (liver, kidney, spleen, heart, lung and brain) after the treatment of mice with different drug formulations by measuring the expression of apoptosis executor—caspase 3 (FIG. 4, panel c) and by immunochemical determination of histone-complexed DNA fragments (mono- and oligonucleosomes) (FIG. 5). Empty liposomes and LHRH did not induce detectable levels of apoptosis either in tumor, ascites, or healthy organs (FIG. 5, bars 1, 2, 3). Free DOX, CIS and their combination activated caspase 3 and induced apoptosis in tumor and malignant ascites (FIG. 4, panel c, #2; FIG. 5, bars 1, 4, 10, 16). However, in addition to inducing apoptosis in tumor and malignant ascites, treatment of mice with free drugs led to the substantial apoptosis induction in the liver, kidney, spleen, heart and lung. Incorporation of drugs into the liposomes substantially enhanced their ability to induce apoptosis in solid tumors and accompanying intraperitoneal metastases and limited apoptosis induction in kidney, spleen, heart and lung (FIG. 5, bars 5, 11, 17). However, apoptosis in the liver remained augmented after the treatment of mice with all non-targeted liposomal DDS (FIG. 5, bars 5-8, 11-14, 17-20). Suppression of both types of cellular resistance by ASO targeted to MDR1 and BCL2 mRNA substantially increased the expression of caspase 3 (FIG. 4, panel c, #6) and apoptosis induction (FIG. 5, bars 6-8, 12-14, 18-20). Targeting of DDS containing anticancer drugs and suppressors of pump and nonpump resistance specific to cancer cells by LHRH peptide led to several positive consequences. First, it increased the level of suppression of targeted proteins and therefore augmented the activation of caspase 3 and apoptosis itself in cancer cells (FIG. 4, panel c, #8-10; FIG. 5, bars 9, 15, 21). Second, the delivery of drugs and other active components specifically to cancer cells prevented the induction of apoptosis in the liver as well as all other studied healthy organs (FIG. 5, bars 9, 15, 21). Third, incorporation of a targeting moiety in DDS led to the prevention of the development of intraperitoneal metastases and malignant ascites (FIG. 5, bars 9, 15, 21 and FIG. 6, bars 9, 15, 21).

Antitumor Effect

The antitumor effect of all studied formulations was estimated by the measurement of the volume of the primary tumor and total mass of the intraperitoneal metastases. Treatment of mice with saline, empty liposomes, and LHRH peptide (controls) did not influence the growth of primary tumor or the development of intraperitoneal metastases (FIG. 6, lines and bars 1-3). Free and liposomal DOX slowed down the growth of the primary subcutaneous tumor but was not effective in preventing the formation of malignant ascites or intraperitoneal metastases and did not statistically significantly decrease their mass (FIG. 6, lines and bars 4, 5). Free and liposomal CIS was more effective in limiting the growth of both primary tumor and malignant ascites when compared to corresponding DOX formulations (compare lines and bars 10, 11 with 4, 5 in FIG. 6). The combination of two drugs (free and liposomal forms) was more effective when compared with formulations containing only one drug (compare lines and bars 16, 17 with 4, 5 and 10, 11 in FIG. 6). Inclusion of ASO targeted to MDR1 and/or BCL2 mRNA into the liposomal drug formulations led to the more significant suppression of the growth of the primary tumor, carcinomatosis and ascites (FIG. 6, lines and bars 6-8, 12-14, 18-20). Targeting of DDS specifically to cancer cells by LHRH peptide further increased antitumor activity of liposomal DDS and prevented the development of intraperitoneal metastases and ascites (FIG. 6, lines and bars 9, 15, 21).

Herein, the antitumor effect of a liposomal tumor-targeted proapoptotic anticancer drug delivery system on the primary tumor and intraperitoneal metastases was examined in a mouse model developed after subcutaneous inoculation of cancer cells isolated from malignant ascites of patients with ovarian carcinoma. Inoculation of these cancer cells provoked, in untreated mice, the development of two models of cancer. The first one represented a subcutaneous model of aggressive primary tumor. The second model of intraperitoneal metastases with ascites developed in approximately 80% of untreated mice. This mouse model of human intraperitoneal carcinomatosis with ascites is different from traditionally used orthotopic models when established cancer cells, primary tumor isolates, or cells from human malignant ascites are intraperitoneally injected into nude mice (De Cesare et al. (2010) J. Immunother., 33:8-15; Hsieh et al. (2009) Cancer Sci., 100:537-545; Pasquet et al. (2010) Int. J. Cancer 126: 2090-2101; Pourgholami et al. (2006) Clin. Cancer Res., 12:1928-1935; Song et al. (2008) Cancer Biol. Ther., 7:76-80). This model more adequately showed the natural progression of ovarian cancer with the development of carcinomatosis and ascites. It is interesting that this model can be effectively employed only when the cells that are used for the initiation of primary subcutaneous tumor are very invasive and multidrug resistant. It was found that intraperitoneal metastases never developed when drug sensitive ovarian cancer cells were injected subcutaneously. When established human multidrug resistant ovarian cancer cell lines or primary tumor isolates were used, malignant ascites accompanied only approximately 10% of primary tumors. Consequently, one can conclude that cancer cells isolated from human ovarian malignant ascites are substantially more invasive when compared with established multidrug resistant cancer cell lines. Such an assumption is also supported by the data of Veatch et al. (Int. J. Cancer. (1994) 58:393-399) who found that " . . . ascites cells were 4-fold more invasive than solid tumor cells." In addition, the development of multidrug resistance accompanied by overexpression of the MDR1 gene was observed in tumors of patients treated with DOX (Abolhoda et al. (1999) Clin. Cancer Res., 5:3352-3356). Taking into account that cells from ovarian malignant ascites belong to a multidrug resistant phenotype, effective therapy of intraperitoneal metastases and ascites requires drugs with different mechanisms of action and the simultaneous suppression of both cellular pump and nonpump resistance. Ideally, any cytotoxic treatment should preferentially target cancer cells sparing healthy tissues. This was successfully accomplished by targeting the LHRH receptor (Chandna et al. (2007) Mol. Pharm., 4:668-678; Dharap et al. (2005) Proc. Natl. Acad. Sci., 102:12962-12967; Chandna et al. (2010) Pharm. Res.). The experimental verification of this hypothesis showed several advantages of the instant approach.

The first advantage is the simultaneous suppression of both major types of cellular resistance. It was found that antisense oligonucleotides targeted to MDR1 and BCL2 mRNA and delivered by PEGylated liposomes effectively suppressed both the major drug efflux pump (P-glycoprotein) and the antiapoptotic cellular defense (BCL2 protein) leading to the inhibition of cellular pump and nonpump resistance, respectively. Second, such suppression led to the substantial enhancement of cell death and increased efficiency of standard cytotoxic drugs to levels that could not be achieved using conventional therapy by free or liposomal forms of the drugs. Third, effective cell death induction in primary tumor and intraperitoneal metastases led to the substantial regression of tumor growth and decrease in total mass of intraperitoneal metastases. Fourth, targeting of DDS specifically to ovarian cancer cells significantly reduced the adverse side effects of the treatment on healthy organs. This effect is explained by the specific body distribution of the tumor targeted delivery system, where the major part of intravenously injected tumor-targeted DDS is accumulated in tumor cells, while only trace amounts of DDS can be found in healthy organs (Chandna et al. (2007) Mol. Pharm., 4:668-678; Dharap et al. (2005) Proc. Natl. Acad. Sci., 102:12962-12967). The fifth advantage of the instant approach includes the prevention of the development of detectable intraperitoneal metastases and ascites after the treatment of an aggressive primary ovarian tumor with the targeted DDS. Moreover, it was found that each targeted DDS containing either one drug alone or a drug combination prevented the formation of carcinomatosis and ascites. In contrast, similar non-targeted systems containing the same components (drug, ASO targeted to MDR1 and ASO targeted to BCL2 mRNA) did not produce such an effect. These results reinforce the importance of targeting anticancer therapy specifically to cancer cells (by a ligand to extracellular receptors overexpressed in cancer cells) for the prevention of the development of intraperitoneal metastases and ascites. The aforementioned advantages of the proposed targeted combinatorial treatment of primary aggressive ovarian tumor and prevention of the development of intraperitoneal metastases make the instant approach of utilizing tumor-targeted delivery systems ideal for clinical applications.

Example 2

Novel therapeutic approaches based on RNA interference (RNAi), a post-transcriptional gene silencing mechanism, mediated by small duplex RNA, attract substantial attention (Gary et al. (2007) J. Control Rel., 121:64-73; Patil et al. (2008) Bioconjug. Chem., 19:1396-1403; Patil et al. (2009) Biomacromol., 10:258-266; Saad et al. (2008) Nanomed., 3:761-776; Taratula et al. (2009) J. Control Rel., 140:284-293; Zhou et al. (2006) Chem. Commun. (Carob) 22:2362-2364). However, similar to other gene therapy strategies, low stability in the bloodstream and poor cell penetration ability of naked small interfering RNA (siRNA) represent main obstacles for the practical use of these methodologies (Gary et al. (2007) J. Control Rel., 121:64-73; Kang et al. (2005) Pharm. Res., 22:2099-2106; Patil et al. (2008) Bioconjug. Chem., 19:1396-1403; Patil et al. (2009) Biomacromol., 10:258-266; Taratula et al. (2009) J. Control Rel., 140:284-293; Zhou et al. (2006) Chem. Commun. (Carob) 22:2362-2364). Viruses developed the ability to deliver double and single stranded DNA and RNA across the cell membrane; however, the immune response elicited by viral proteins limited their use as delivery agents (Bessis et al. (2004) Gene Ther., 11:S10-17). Therefore, the development of non-viral systems, which are able to protect siRNA during its journey in the circulation to the site of action and effectively deliver it across the cell membrane to the cytoplasm to guide the sequence-specific mRNA degradation, is very important in order to exploit their therapeutics potential.

Studies of non-viral gene therapy based on plasmid DNA (pDNA) have being carried out for years to improve systemic delivery and transfection efficiencies of pDNA to the levels required for in vivo clinical trials. It has been recognized that a prerequisite for the facile transport of pDNA through the cell membrane is the condensation (packaging) of the nucleic acids into nanoparticles, which can protect pDNA by sterically blocking its degradation by nucleolytic enzymes (Vijayanathan et al. (2002) Biochem., 41:14085-14094). pDNA and siRNA are both double-stranded nucleic acids, they have anionic phosphodiester backbones with the same negative charge to nucleotide ratio, and can interact electrostatically with cationic agents (Gary et al. (2007) J. Control Rel., 121:64-73). Therefore, one can use the knowledge gained from the longer-studied pDNA to develop systems for an effective delivery of siRNA. However, despite the similarities, pDNA and siRNA are very different from each other in molecular weight and molecular topography with potentially important consequences. The pDNA used in gene therapy is often several kilo base pairs long and possesses a molecular topography, which allows the condensation into small, nanometer size particles when complexed with a cationic agent (Gary et al. (2007) J. Control Rel., 121:64-73; Spagnou et al. (2004) Biochem., 43:13348-13356). Unlike pDNA, the persistence length (the length scale over which the chains behave as rigid rods) of double-stranded RNA is ~70 nm (Kebbekus et al. (1995) Biochem., 34:4354-4357) which is about 260 base pairs (bp) based on the value of 2.7 Å/bp (Shah et al. (1999) J. Mol. Biol., 285:1577-1588). Therefore, siRNA with 21 bp essentially should behave as a rigid rod and is difficult to bend. Consequently, the different interactions with cationic agents may result in undesirably large complexes or incomplete encapsulation of siRNA molecules, which thereby may expose siRNA to potential enzymatic or physical degradation in the bloodstream prior to the delivery to the targeted cells (Spagnou et al. (2004) Biochem., 43:13348-13356).

Over the years, cationic liposomes and polycations have been explored as nonviral vectors for the delivery of siRNA (Garbuzenko et al. (2009) Pharm. Res., 26:382-394; Saad et al. (2008) Nanomed, 3:761-776). An advantage of using polycationic polymers, such as Poly(Ethyleneimine) (PEI), is that they allow for an efficient gene transfer without the need for agents facilitating endosomal escape of the payload. However, such polymers have a wide range of molecular weight distribution and their transfection efficiency and cytotoxicity are dependent on the molecular weight and polydispersity (Gary et al. (2007) J. Control Rel., 121:64-73; Pack et al. (2005) Nat. Rev. Drug Discov., 4:581-593; Spagnou et al. (2004) Biochem., 43:13348-13356; Vijayanathan et al. (2002) Biochem., 41:14085-14094). In contrast, the novel highly branched three-dimensional molecules, called dendrimers, have defined molecular weight and a large number of controllable surface charges and surface functionalities (Dufes et al. (2005) Adv. Drug Deliv. Rev., 57:2177-2202). These properties of dendrimers provide a platform for an effective siRNA intracellular delivery, with potentially less complications from heterogeneity and variable chemistry, commonly seen in other nonviral vectors, such as cationic lipids and PEI (Chen et al. (2006) Nanotechnol., 17:5449-5460; Santhakumaran et al. (2004) Nucl. Acids Res., 32:2102-2112; Vijayanathan et al. (2002) Biochem., 41:14085-14094). Poly(propyleneimine) (PPI) dendrimers are members of a class of amine-terminated polymers that have been used as efficient gene delivery vectors with low cytotoxicity in a wide range of mammalian cell lines (Chen et al. (2006) Nanotechnol., 17:5449-5460; Santhakumaran et al. (2004) Nucl. Acids Res., 32:2102-2112; Taratula et al. (2009) J. Control Rel., 140:284-293). The multiple functional groups on the surface of these dendrimers also allow the design of multifunctional delivery systems containing other active components (e.g. targeting moieties, etc.) in addition to siRNA (Patil et al. (2008) Bioconjug. Chem., 19:1396-1403; Taratula et al. (2009) J. Control Rel., 140:284-293). However, most of the synthetic vectors, including dendrimers, usually possess lower efficiency in intracellular nucleic acid delivery (Pack et al. (2005) Nat. Rev. Drug Discov., 4:581-593). Therefore, fundamental understanding of the molecular structure of nonviral vectors and their structure-function relationship is essential for rational design of nonviral delivery vehicles with the therapeutic effectiveness that can match or be better than the viral counterpart. Consequently, by linking the chemical structures of cationic vehicles to the morphology and physicochemistry of the respective nucleic acid complexes and their biological properties on cellular and systemic levels is essential for the development of nonviral delivery vehicles with efficiency that can match or be better than their viral counterpart. The present work is aimed at studying the properties of nanoparticles formed by the complexation of model siRNA with PPI dendrimers of different generations, the morphology and cellular toxicity of such complexes and their efficiency to deliver the payload into the cytoplasm and silence the targeted gene.

Material and Methods

Materials

Dendrimers, poly(propyleneimine) octaamine (DAB Am-8, generation-2, PPI G2), poly(propyleneimine) hexadecaamine (DAB Am-16, generation-3, PPI G3), poly(propyleneimine) dotriacontaamine (DAB Am-32, generation-4, PPI G4), and poly(propyleneimine) tetrahexacontaamine, DAB-Am-64, generation-5, PPI G5) were purchased from Aldrich (Milwaukee, Wis.), and used without further purification. Ethidium Bromide (EtBr) solution was purchased from Promega (Madison, Wis.). The sequence of siRNA targeted to BCL2 mRNA (custom synthesized by Ambion, Austin, Tex.), was 5'-GUGAAGUCAACAUGCCUGC-dTdT-3' (sense strand; SEQ ID NO: 4) and 5'-GCAGGCAUGUUGACU-UCAC-dTdT-3' (antisense strand; SEQ ID NO: 5). 6-FAM siRNA (SiGLO® Green) was obtained from Applied Biosystems (Ambion, Inc., Foster City, Calif.). All other chemicals were purchased from Fisher Scientific (Fairlawn, N.J.).

Cell Line

Human A549 lung carcinoma cells were obtained from the ATTC (Manassas, Va., USA). Cells were cultured in RPMI 1640 medium (Sigma, St. Louis, Mo.) supplemented with 10% fetal bovine serum (Fisher Scientific, Fairlawn, N.J.). Cells were grown at 37° C. in a humidified atmosphere of 5% $CO_2$ (v/v) in air. All experiments were performed on cells in the exponential growth phase.

Ethidium Bromide (EtBr) Dye Displacement Assay

Fluorescence titration of siRNA-ethidium bromide complexes with different generations of PPI dendrimers were performed as follows. The complexes prepared from siRNA with EtBr intercalated at 4:1 ratio in water and 1 μL aliquots of the dendrimer solutions were sequentially added to 2 μM solution of siRNA in 180 μL of water containing EtBr. After each addition, the mixture was stirred and the fluorescence of the solution was measured (490 nm excitation; 590 nm emission). The total dendrimer amount added to the siRNA solution exceed 5% of the total volume of the mixture, hence sample dilution factors on the measured fluorescence emission intensity was corrected. All fluorescence measurements were performed using a Cary-Eclipse fluorescence spectrophotometer (Varian, Inc, Palo Alto, Calif.). The relative fluorescence was based on three independent experiments and calculated using the following equation: % Relative Fl=[(Fl (obs)−Fl(EtBr))/(Fl(siRNA+EtBr)−Fl(EtBr))]×100, where Fl (obs)−fluorescence of siRNA+ethidium bromide+complexation agent; Fl (EtBr)−fluorescence of ethidium bromide alone; Fl(siRNA+EtBr)−fluorescence of siRNA+ethidium bromide.

Formulation of siRNA-Dendrimer Complexes

The complexes of siRNA with each generation of PPI dendrimers (G2, G3, G4, and G5) were designed at constant amine/phosphate ratios (N/P ratio) such as 2.4. Briefly, 100 μM siRNA solutions were mixed with deionized water and an appropriate amount of the dendrimers was added. The final concentration of siRNA in the solution was 4.0 μM, while the concentrations of PPI G2, G3, G4, and G5 dendrimers were 50.4 μM, 25.2 μM, 12.6 μM, and 6.3 μM, respectively. The complexes were stirred and equilibrated for 30 minutes prior to analysis.

Atomic Force Microscopy (AFM)

In order to obtain AFM images of formulated complexes, 5 μL aliquots of siRNA-dendrimer solutions were deposited on a freshly cleaved mica surface. After 5 minutes of incubation, the surface was rinsed with several drops of nanopure water (distilled water filtered through an ion filter with organic compounds also has been removed using a carbon filter resulting in analytical grade water), and dried under a flow of dry nitrogen. AFM images were obtained using Nanoscope IIIA AFM (Digital Instruments, Santa Barbara, Calif.) in tapping mode, operating in an ambient atmosphere.

Agarose Gel Retardation Assay

The complexes of siRNA with different generations of PPI dendrimers were prepared in water as already described. Free siRNA was used as the control. Double-stranded RNA ladder (New England Biolabs) with the smallest base pairs at 21 was used as a size reference. The samples were further diluted with water and electrophoresed in 4% agarose gel at 100 mV for 60 minutes in TBE buffer and stained with EtBr. The gels were digitally photographed, and scanned using Gel Documentation System 920 (NucleoTech, San Mateo, Calif.).

Dynamic Light Scattering (DLS)

The DLS studies were performed using the Dawn EOS multi-angle light scattering spectrometer modified with a QELS attachment (Wyatt Technology Corp., Santa Barbara, Calif.). Data were collected at an angle of 108° using an avalanche photodiode and an optical fiber and processed with the Wyatt QELS software (regularization analysis). Each light scattering experiment consisted of 5 or more 60 second independent readings.

In Vitro Cytotoxicity

A modified MTT (3-(4,5-dimethylthiazol-2-yl)-2,5-diphenyltetrazolium bromide) assay was used to assess the cytotoxicity of different generations of PPI dendrimer as previously described (Jayant et al. (2007) Pharm. Res., 24:2120-2130). To measure cytotoxicity, human A549 lung carcinoma cells were separately incubated in a microtiter plate with different concentrations of each PPI G2, G3, G4, and G5 dendrimers. Control cells received an equivalent volume of fresh medium. The duration of incubation was 24 hours. On the basis of these measurements, cellular viability was calculated for each dendrimer concentration. A decrease in the cellular viability indicated an increase in dendrimer toxicity.

Cellular Internalization

To analyze cellular internalization and intracellular localization of the condensed complexes, 6-FAM labelled siRNA was used as previously described (Saad et al. (2008) J. Control Rel., 130:107-114; Taratula et al. (2009) J. Control Rel., 140:284-293). Prior to the visualization, A549 cells were plated (20,000 cells per well) in a 6-well tissue culture plate. The cells were treated within 24 hours with the siRNA complex prepared with different generations of PPI dendrimer. The treatment of the A549 cells was performed in such a manner that the final concentration of siRNA was 0.25 µM and the concentrations of PPI G2, G3, G4, and G5 dendrimers were 3.15 µM, 1.58 µM, 0.79 µM, and 0.39 µM, respectively. After 24 hours of treatment, the cells were washed three times with Phosphate Buffered Saline (PBS) and 1 mL of media was added to each well. Cellular internalization of siRNA-dendrimer complexes were analyzed by fluorescent (Olympus America Inc., Melville, N.Y.) and confocal (Leica Microsystems Inc., Bannockburn, Ill.) microscopes. To obtain intracellular distribution of siRNA, ten optical sections, known as a z-series, were photographed sequentially, by confocal microscope, along the vertical (z) axis from the top to the bottom of the cell. The obtained fluorescent images were digitally scanned and fluorescence inside cells (reflecting intracellular accumulation of labelled siRNA) was expressed in arbitrary units.

Gene Expression

Quantitative reverse transcription-polymerase chain reaction (RT-PCR) was used for the analysis of expression of genes encoding BCL2 protein and $\beta_2$-microglobulin (internal standard) as previously described (Pakunlu et al. (2003) Pharm. Res., 20:351-359). RNA was isolated after 24 hours incubation of cancer cells with siRNA-dendrimer complexes, using an RNeasy kit (Qiagen, Valencia, Calif.). First strand complementary DNA (cDNA) was synthesized by Ready-To-Go You-Prime First-Strand Beads (Amersham Biosciences, Piscataway, N.J.) with 4 mg of total cellular RNA and 100 ng of random hexadeoxynucleotide primer (Amersham Bioscience, Piscataway, N.J.). After synthesis, the reaction mixture was immediately subjected to PCR, which was carried out using GenAmp® PCR System 2400 (Perkin-Elmer, Shelton, Conn.). The following pairs of primers were used: BCL2-GGA TTG TGG CCT TCT TTG AG (sense; SEQ ID NO: 6), CCA AAC TGA GCA GAG TCT TC (antisense; SEQ ID NO: 7); $\beta_2$-microglobulin ($\beta_2$-m)-ACC CCC ACT GAA AAA GAT GA (sense; SEQ ID NO: 8), ATC TTC AAA CCT CCA TGA TG (antisense; SEQ ID NO: 9). PCR products were separated in 4% NuSieve® 3:1 Reliant agarose gels in 1*TBE buffer (0.089 M Tris/Borate, 0.002 M EDTA, pH 8.3; Research Organic Inc., Cleveland Ohio) by submarine gel electrophoresis. The gels were stained with ethidium bromide, digitally photographed and scanned using Gel Documentation System 920 (NucleoTech, San Mateo, Calif.). Gene expression was calculated as the ratio of mean band intensity of analyzed RT-PCR product (BCL2) to that of the internal standard ($\beta_2$-m). The value of BCL2 gene expression for the cells incubated with fresh medium (control) was set as 100%.

Statistical Analysis

Data were analyzed as described hereinabove in Example I for four to eight independent measurements.

Results

Evaluation of Interaction Between siRNA and PPI Dendrimers of Different Generation by EtBr Displacement Assay Similarly to pDNA, the complex formation between negatively charged siRNAs and positively charged polycations is primarily driven due to electrostatic interaction. The amount of polycations needed for the complex formation could be estimated by N/P (nitrogen/phosphate) ratios, which refer to the ratio of the positively charged primary amine groups of polycations to negatively charged phosphate groups of siRNA (Gary et al. (2007) J. Control Rel., 121:64-73). EtBr intercalates between the base pairs of the DNA double helix, yielding a highly fluorescent DNA-EtBr complex (Izumrudov et al. (1999) Biopolymers, 52:94-108). Upon polycations binding, the DNA double helix structure is distorted and EtBr is expelled from the DNA-EtBr complex, resulting in a decrease of fluorescence (Izumrudov et al. (1999) Biopolymers, 52:94-108). The degree of EtBr displacement thus provides for a measure of the binding affinity, indicating the relative strength of the interaction between DNA and polycations. A similar process was found for siRNA in the present study, as shown in FIG. 7A. Although the exact mechanism of EtBr release from siRNA requires an additional detailed study, the differences in the ability of dendrimers to displace EtBr from siRNA provide a comparison of the binding affinities between siRNA and the PPI dendrimers of different generations (Thomas et al. (2005) Proc. Natl. Acad. Sci., 102: 5679-5684). FIG. 7B shows that fluorescence intensities decreased progressively with increasing N/P ratios up to 0.36, 0.55, 0.74, and 0.92 for PPI G4, G5, G3 and G2, respectively. These ratios, which represent the apparent end point of complexation for each PPI dendrimer generation, respectively, indicated that the interaction strength between PPI dendrimers and siRNA decreases as follows: G4>G5>G3>G2.

Size and Morphology of Formulated siRNA-Dendrimer Complexes

Figure 9A:
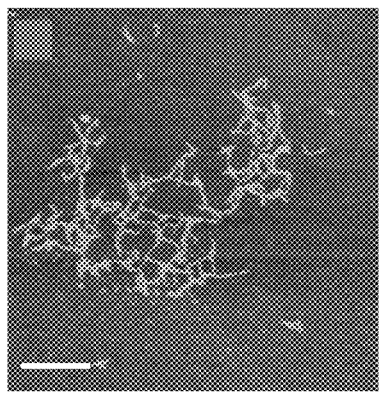
Figure 9B:
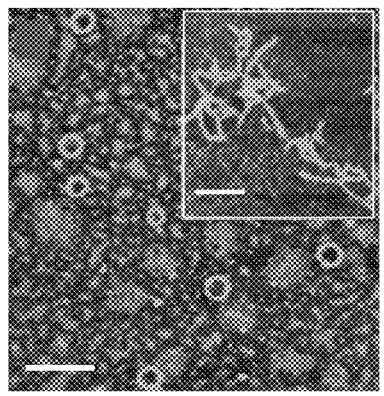
Figure 9C:
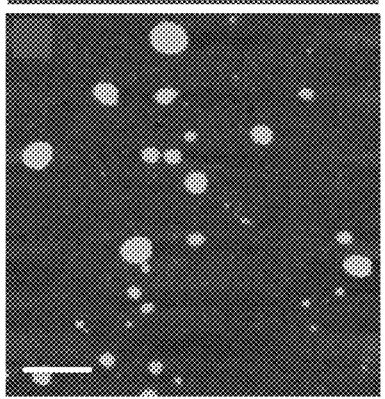
Figure 9D:
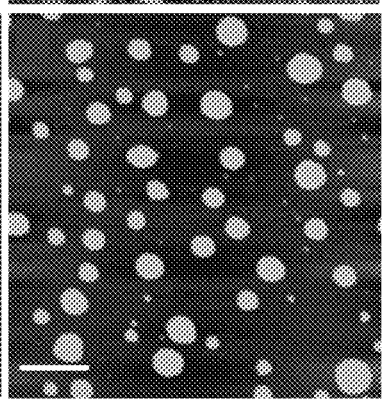

Tapping mode AFM was used to study the size and morphology of siRNA complexes prepared in the presence of different generations of PPI dendrimers. To ensure a complete siRNA complexation, all the siRNA complexes with different generation dendrimers were formulated at a ratio of 2.4, which is several times higher than the apparent end points of condensation observed by EtBr dye displacement assay. Agarose gel retardation assay was applied to further ensure that this N/P ratio was sufficient for siRNA complex formation (FIG. 8A). As shown in FIG. 9, fiber- and sphere-shaped nanostructures were formed in the presence of PPI G2 to G5 dendrimers after 30 minutes of condensation. The lower generations of dendrimers are capable to complex siRNA resulting in the formation of randomly aggregated nanofibers (G2) (FIG. 9A), or a mixture of nanofibers and toroids (doughnut-shaped objects) (G3), respectively (FIG. 9B). The height of the fiber-like structures was around 1.7 nm with the length varied from 100 nm to several µm, whereas the average height and diameter of toroids were 2.9±0.2 nm and 176.6±12.3 nm, respectively. The relatively weak electrostatic cooperative interaction between siRNA and PPI G2 or PPI G3 may be the reason to form this fiber shaped structures. On the other hand, the products of siRNA condensation with higher generations of PPI dendrimers appear to be relatively uniform nanoparticles with average diameters 150.3±24.7 nm and 150.1±22.2 nm for PPI G4 and PPI G5, respectively (FIG. 9C-D). Whereas the average heights of the siRNA complexes formed in the presence of PPI G4 and PPI G5 were 6.2±0.9 nm and 5.4±0.9 nm, respectively. It is worthy to mention that the height values of spherical gene delivery complexes measured by AFM are almost always lower than their diameters. The major factors contributing to the lower height values are elastic deformation induced by AFM tip-sample interaction and the compression caused by the attractive forces between complexes and the substrate (Oh et al. (2006) J. Am. Chem. Soc., 128:5578-5584). DLS technique was also used to determine the hydrodynamic size of the siRNA complexes without perturbation by the surface immobilization process and the AFM tip. Similar trend was found with increasing generations of the PPI dendrimer, even though the absolute size of the complexes measured by DLS was relatively small. The hydrodynamic diameter for siRNA complexes formed in the presence of higher generations PPI dendrimers were 96.8±11.3 nm and 101.2±23.8 nm for PPI G4 and PPI G5, respectively. Additionally, the solutions of siRNA-PPI G2 and siRNA-PPI G3 had hydrodynamic diameters of 224.0±58.5 nm and 129.8±26.4 nm, which was attributed to the fiber and torus-like constructions (FIG. 10A).

Cellular Internalization and Intracellular Localization of siRNA-Dendrimer Complexes To achieve an enhanced gene silencing therapeutic effect, sequence-specific siRNA molecules have to be delivered efficiently into the cytoplasm of cells, where the RNAi machinery is located. To determine whether the studied PPI dendrimers were able to efficiently deliver siRNA into cancer cells, the cellular internalization of the FAM-labelled siRNA (free or complexed) was investigated by fluorescence microscopy after their incubation with A549 human lung cancer cells. The quantitative evaluation of siRNA internalization efficiency based on the emission intensity showed that the intracellular uptake of the complexed and free siRNA was dramatically different and strongly dependent on dendrimer generation (FIG. 10B). Whereas free siRNA as well as siRNA-PPI G2 complexes were not internalized by the cells, siRNA complexes formulated in the presence of G3, G4 and G5 dendrimers were capable of facilitating siRNA internalization into the cytoplasm. Overall, the efficiency of the studied complexation agents to provoke siRNA intracellular uptake declines in the following order: PPI G4>PPI G5>PPI G3>PPI G2 (FIG. 10B). The result is consistent with the ability of the dendrimers in provoking siRNA condensation into discrete nanoparticles. In the present study, the intracellular distribution of the siRNA-PPI complexes in A549 human lung cancer cells was investigated by confocal microscopy (FIG. 11). Analysis of the obtained images demonstrated the fluorescence from 6-FAM labelled siRNA delivered by PPI G3, G4 and G5 dendrimers was localized primarily in the cytoplasm of the cells and was not registered in the nuclei. The siRNA complexes formed with PPI G3-G5 dendrimers were uniformly distributed in the cytoplasm from the top to the bottom of the cells (FIG. 11C-E).

Gene Silencing Efficiency of siRNA-Dendrimer Complexes In Vitro

In order to achieve therapeutic effects by the internalized siRNA, the complex which protects siRNA in an extracellular environment has to be able to escape from the endosome and release siRNA into the cytoplasm. To evaluate the silencing efficacy of the siRNA delivered by PPI dendrimers, the siRNA complexes formulated in the presence of four different generations of PPI dendrimers were incubated with A549 lung cancer cells and the expression of targeted BCL2 mRNA was measured by RT-PCR. FIG. 12 shows that siRNA delivered by PPI G5 and G4 dendrimers sufficiently induced degradation of the targeted BCL2 mRNA. siRNA-PPI G5 complexes resulted in 75% gene knockdown, while siRNA-PPI G4 exhibited almost complete suppression of the targeted BCL2 mRNA in A549 lung cancer cells. On the other hand, siRNA complexed with PPI G3 dendrimer resulted in only a 40% decrease in gene knockdown and the condensed siRNA with PPI G2 dendrimer showed no statistically significant silencing effect. Gene silencing was not observed with naked siRNA and all generations of PPI dendrimer without siRNA.

In Vitro Cytotoxicity of PPI Dendrimers

Cytotoxicities of gene transfection vectors including viral vectors, inorganic nanoparticles, cationic liposomes and polymers are considered as a substantial concern for their clinical applications. In order to examine whether different generations of PPI dendrimers influenced cell viability of A549 human lung cancer cells, the MTT assay was employed. FIG. 8B shows the average data obtained in three independent experiments with increasing concentration of PPI dendrimers of different generations. The cytotoxicity of the dendrimers increased with the generation, following the order of the least to most cytotoxic: G2<G3<G4<G5. The data are correlated with membrane damage effects, implying that the increase in positive charge causes more efficient binding to the negatively charged cell membrane and destabilizing them (Kunath et al. (2003) J. Control Rel., 88:159-172). In the in vitro experiments described here, the concentrations of PPI G2, G3, G4 and G5 dendrimers was 3.15 µM, 1.58 µM, 0.79 µM and 0.39 µM, respectively, which are substantially lower than the threshold of cellular toxicity of the carriers.

Antitumor Activity of PPI Dendrimer

The silencing of BCL2 and antitumor activity of LHRH-Targeted and Non-Targeted PPI Dendrimer formulations containing cisplatin and siRNA were determined. Briefly, mice (see mouse xenograft model above) were treated three timed within 14 days with the following formulations: (1) Control (saline); (2) PPI dendrimer; (3) LHRH; (4) Naked siRNA targeted to BCL2 mRNA; (5) BCL2 siRNA-PPI-DTBP-PEG; (6) LHRH-BCL2 siRNA-PPI-DTBP-PEG; (7) Free CIS; (8) BCL2 siRNA-PPI-DTBP-PEG+CIS; (9) LHRH-BCL2 siRNA-PPI-DTBP-PEG+CIS. The results are presented in FIG. 13. Notably, the administration of LHRH targeted dendrimers with BCL2 siRNA and cisplatin lead to the greatest reduction of tumor volume.

Here, PPI dendrimers of different generations (G2 to G5) were evaluated in terms of their ability for siRNA condensation ability and intracellular delivery of siRNA. It was found that the structure of dendrimers substantially influences their abilities to form stable complexes with siRNA and to deliver the payload to the cytoplasm. By evaluating the results from all experiments, PPI G4 dendrimer is the most suitable for this purpose.

In general, the binding affinity of polycations to nucleic acids is determined by the number of charges and their density per molecule available for the interaction. With each increasing generation of the PPI dendrimer, the number of surface amine groups, which are most likely to bind siRNA, doubles. Therefore, it can be assumed that the strength of the bond increases with dendrimer generations, which is largely due to the increase in the number of primary amino groups in higher generation dendrimers. Additionally, it was reported that DNA binding affinity with dendrimers was largely affected by the size of dendrimers, which increases with each generation (Dufes et al. (2005) Adv. Drug Deliv. Rev., 57:2177-2202). Molecular modelling studies of PPI dendrimers of all 5 generations (Zinselmeyer et al. (2002) Pharm. Res., 19:960-967) showed that the PPI G1 appears to bind across the major groove of DNA, PPI G3 is sufficiently large to bind across an entire helical turn, spanning major as well as minor grooves. For generation 4 and 5, a significant proportion of the PPI dendrimer molecules were able to interact directly with multiple DNA strands.

Here, it was found that PPI G4 was more efficient in terms of complex formation with siRNA, despite the PPI G5 dendrimer containing more primary amino groups (64 vs. 32) and have a larger size (the hydrodynamic diameters of G4 and G5 dendrimers in water solutions are about 3.12 and 3.96 nm, respectively (Rietveld et al. (1999) Macromolecules, 32:4608-4614)). These results are in a good agreement with other studies (Santhakumaran et al. (2004) Nucleic Acids Res., 32:2102-2112), which demonstrated that PPI G4 dendrimer was the most efficient triplex-forming oligodeoxynucleotide delivery agent for five cancer cell lines. It is also consistent with the previous study on the compaction and delivery of antisense oligonucleotides into breast cancer cells (Chen et al. (2006) Nanotechnol., 17:5449-5460).

The better efficiency of PPI G4 dendrimer compared to PPI G5 dendrimer in provoking siRNA complexation could be explained by the difference in the flexibility of the dendrimers, which decreases with an increase in the number of dendrimer generation (Guillot-Nieckowski, et al. (2007) New J. Chem., 31:1111-1127). It was reported that partially degraded PAMAM dendrimers were more efficient than the intact dendrimers in condensation of DNA and antisense oligonucleotides, because they are more easily collapsed after the neutralization of the charge with nucleic acid due to the enhanced flexible structures (Dennig et al. (2002) J. Biotechnol., 90:339-347.).

It was found that G4 dendrimer has the highest cooperative electrostatic interaction with the siRNA despite G5 dendrimer has the highest charge density, possibly due to the decreased flexibility or steric hindrances of G5 that are resulted in a relatively lower cooperative interaction with the siRNA. Since the flexibility of a transfection vector as well as the size and the amount of protonated primary amines on the outer surface drives its ability to compact nucleic acids tightly, the optimal combination in PPI G4 structures makes it the most efficient complexation agent among all other generations.

The size and morphology of siRNA complexes are the important factors in siRNA internalization and can dramatically influence their transfection efficiency (Chen et al. (2006) Nanotechnol., 17:5449-5460; Patil et al. (2008) Bioconjug. Chem., 19:1396-1403; Patil et al. (2009) Biomacromolecules, 10:258-266.; Taratula et al. (2009) J. Control Release, 140:284-293). It was found that lower generations of dendrimers (G2 and G3) formed with siRNA randomly aggregated nanofibers (G2) or a mixture of nanofibers and toroids (G3). In contrast, higher generations of PPI dendrimers formed well-condensed relatively uniform spherical nanoparticles. At the same time, it was revealed that complexes of G2 and G3 dendrimers with siRNA were unable to penetrate cellular cytoplasm in vitro. Relatively low cellular internalization of siRNA delivered by PPI G2 and PPI G3 dendrimers may be at least partially related to the presence of large aggregated structures (fibers and thin toroids) in the complexes. Furthermore, it was reported that electrostatic interactions between the negatively charged cell membranes and positively charged particles can enhance their cellular uptake (Chen et al. (2006) Nanotechnol., 17:5449-5460). It was reported that complexation of DNA with PPI dendrimers G1 and G2 led to the formation of electroneutral complexes even at dendrimer:DNA charge ratios >1 (Kabanov et-al. (2000) Macromolecules, 33:9587-9593). The higher generations of dendrimers were able to produce charged soluble complexes because of the ability to form overstoichiometric complexes with a net positive charge. Recently, it was also found that all five generations of PPI dendrimers could provoke nanoparticles formation with Antisense Oligonucleotides (ASO) targeted to the c-myc oncogene (Chen et al. (2006) Nanotechnol., 17:5449-5460). However, only generation 4 and 5 dendrimers could deliver ASO to cell nuclei as determined from a confocal microscopic study. Zeta potential measurement of the ASO-PPI complexes formed with dendrimers of different generations shows that the complexes formed from higher generation PPI dendrimers had much higher positive zeta potentials than the lower generation dendrimers. Even though agarose gel retardation assay demonstrated that the siRNA-PPI dendrimer complexes formed from all five generations were retarded, the complexes with lower generation dendrimers may also have lower positive charges, similar to the situation with ASO-dendrimer complexes. Additionally, it was found (Liu et al. (2001) J. Biol. Chem., 276:34379-34387) that large DNA aggregates formed under non-cooperative conditions could not be internalized into cells, and only the fully compacted DNA nanoparticles formed from cooperative binding were able to penetrate through the cellular plasma membrane. Since the PPI G5 dendrimer has less cooperative electrostatic interaction with siRNA when compared with G4, it was hypothesized that the siRNA nanoparticles formed from these two generations may have different physical chemical properties, which may influence the cell uptake. It is also possible that the amount of siRNA nanoparticles formed with PPI G5 dendrimers via cooperative electrostatic binding was less than that in G4 dendrimers. In addition, it has recently been demonstrated (Taratula et al. (2009) J. Control Release, 140:284-293) that certain siRNA-PPI G5 nanoparticles showed aggregation in cell medium, which could prevent some portion of siRNA from the cellular internalization. Although further, more detailed studies are required for the investigation of detailed mechanisms of the phenomenon, one can conclude that generation 4 and 5 dendrimers, particularly G4, provide the most efficient intracellular delivery of complexated siRNA.

Herein, it was found that siRNA delivered by dendrimers located mainly in the cellular cytoplasm but not in nuclei. Since siRNA functions by binding to RNA-induced silencing complex in the cytoplasm, the delivery of siRNA by PPI dendrimers to the cytoplasm but not to nucleus may have the advantage of increasing siRNA gene silencing activity and avoiding toxicity to the nucleus. It has been previously reported that efficiency of RNAi activity was dependent on the siRNA localization in different intracellular compartments (Chiu et al. (2004) Chem. Biol., 11:1165-1175). Most of the reports show that siRNA delivered by both liposome and cationic polymers is localized in cytoplasm and not in the nucleus even after extended periods of time (Garbuzenko et al. (2009) Pharm. Res., 26:382-394.; Keller, M. (2005) J. Control Release, 103:537-540; Saad et al. (2008) Nanomed., 3:761-776; Spagnou et al. (2004) Biochem., 43:13348-13356). However, it was reported that PAMAM dendrimers have a tendency to alter siRNA subcellular localization pattern, which is concentration dependent (Chiu et al. (2004) Chem. Biol., 11:1165-1175). Using higher concentration of PAMAM, they observed that the internalized siRNA was localized in both nucleus and cytoplasm. The authors believe that such distribution correlates with the observed lower RNAi activity (Chiu et al. (2004) Chem. Biol., 11:1165-1175). Overall, the present study showed that the targeted gene silencing ability of the siRNA-dendrimer complex depends on the dendrimer generation, following the same trend as the ability of PPI dendrimer in provoking siRNA complexation and facilitating cellular internalization.

It was shown that PPI dendrimers can be used for the delivery of a plasmid DNA (Zinselmeyer et al. (2002) Pharm. Res., 19:960-967). The greater conformational mobility of the long DNA molecules may facilitate its interaction with the extended structure of lower generation dendrimers more efficiently than the interaction of these dendrimers with the 21 bp siRNA in this study. They also found that the number of binding sites between DNA and the dendrimer increased with molecular weight. It is possible that for a long DNA molecule, sufficient binding sites may be achieved with lower generation dendrimers compared with small siRNA. This is consistent with the reports showing that short DNA molecules were more difficult to condense into well-defined nanoparticles (Bloomfield, 1996; Zinselmeyer, et al., 2002). Due to physicochemical and structural differences, conditions for transfection of plasmid DNA could be different from conditions for transfection of siRNA. The conditions may be more comparable to the short antisense and triplexing forming oligonucleotides (Chen et al. (2006) Nanotechnol., 17:5449-5460; Santhakumaran et al. (2004) Nucleic Acids Res., 32:2102-2112).

Among all dendritic vectors, PAMAM are the most extensively used carriers for plasmid DNA and antisense oligonucleotides (Kang et al. (2005) Pharm. Res., 22:2099-2106; Patil et al. (2008) Bioconjug. Chem., 19:1396-1403; Patil et al. (2009) Biomacromolecules, 10:258-266). It was also demonstrated that nondegradable PAMAM dendrimers are efficient for siRNA delivery and induce potent endogenous gene silencing, which was dependent on the dendrimer generation (Zhou et al. (2006) Chem. Commun. (Camb), 22:2362-2364). On the contrary, it was reported that PAMAM dendrimers have moderate efficiency for the delivery of oligonucleotides and are relatively less effective for delivery of siRNA especially in multidrug resistant cancer cells which overexpress P-glycoprotein (Kang et al. (2005) Pharm. Res., 22:2099-2106). Similarly to the PAMAM dendrimers, the gene silencing ability of the siRNA-PPI dendrimer complex was also depended on the dendrimer generations and in general siRNA delivered by the dendrimers with higher generation demonstrated more efficient gene silencing (Zhou et al. (2006) Chem. Commun. (Camb), 22:2362-2364). However, it was found that the optimal generation of PPI dendrimer is G4, which is much lower when compared with PAMAM dendrimers. It was reported that the best gene silencing results were obtained with G7 dendrimers at a N/P ratio of 10-20 (Zhou et al. (2006) Chem. Commun. (Camb), 22:2362-2364), while only weak gene silencing was observed when PAMAM G5 was used (Kang et al. (2005) Pharm. Res., 22:2099-2106). PAMAM dendrimers have relatively larger size compared to PPI dendrimers, which should be more efficient in complexation of siRNA to form compacted structures. However, on the other hand, PPI dendrimers contain 100% protonable nitrogen (van Duijvenbode et al. (1998) Polymer, 39:2657-2664). The existence of multiple amide nitrogen in the inner structure of the PAMAM, which are nonbasic due to the delocalization of their lone electron pairs with the carbonyl group, siRNA binding and proton-sponge capacity of the PAMAM might be compromised compared to PPI dendrimers.

It was demonstrated that the molecular structure of a nanocarrier, including its charge, size, and flexibility coherently determines siRNA condensation efficiency and the physicochemical properties of the formed siRNA complexes, which in turn controls cellular uptake of the siRNA and the silencing efficiency of the internalized siRNA. PPI dendrimers can be effectively used for packaging and delivering of siRNA into cancer cells. Quantitative evaluation of the efficiency of PPI dendrimer to provoke 21-bp siRNA condensation revealed that all four generations of PPI dendrimers are capable of siRNA packaging. However, PPI G4 was the most efficient in siRNA complexation compared to other studied generations, including PPI G5 dendrimers. Atomic force microscope studies demonstrated that the lower generations of dendrimers were capable to partially condensate siRNA to randomly aggregated nanofibers (G2), or a mixture of nanofibers and thin toroids (G3). In contrast, the products of siRNA condensation with higher generations of PPI dendrimers (G4 and G5) appear to be uniform discrete nanoparticles with average size of 150 nm. Furthermore, siRNA-PPI G2 complexes did not provide for an efficient internalization of siRNA by cancer cells. In contrast PPI G3, G4 and G5 dendrimers were capable to facilitate siRNA internalization into cytoplasm and silence the targeted mRNA. The silencing efficacy also highly depended on the generations of the PPI dendrimers, with the following trend: PPI G4>G5>G3>G2.

Example 3

Design and creation of novel nanometer-size carriers for the safe delivery of small interfering RNA (siRNA) towards their potential applications in cancer therapy is one of the challenging and rapidly growing areas of research. RNA interference (RNAi) is a conservative biological response to siRNA that regulates the expression of protein coding genes (Caplen et al. (2003) Ann. N.Y. Acad. Sci., 1002:56-62; Dave et al. (2003) Rev. Med. Virol., 13:373-385; Dorsett et al. (2004) Nat. Rev. Drug Discov., 3:318-329; Mello et al. (2004) Nature 431:338-342; Sontheimer, E. J. (2005) Nat. Rev. Mol. Cell. Biol., 6:127-138). However, the broad therapeutic applications of siRNA are limited by major delivery problems (Paroo et al. (2004) Trends Biotechnol., 22:390-394). The efficient in vivo gene knock down requires a delivery system that would overcome the following limitations: (1) low cellular uptake, (2) poor endosomal escape, (3) substantial liver and renal clearance, (4) facile enzymatic degradation in the blood and extracellular environment and (5) inefficient gene silencing.

Recent investigations in the area of nanomaterials for RNA delivery provided solutions to some of the major siRNA delivery problems (Chen et al. (2009) Small 5:2673-2677; Christie et al. (2010) Endocrinology 151:466-473; Guo et al. (2010) Adv. Drug Deliv. Rev., 62:650-666; Ladewig et al. (2010) Biomaterials 31:1821-1829; Minko et al. (2010) Methods Mol. Biol., 624:281-294; Ozpolat et al. (2010) J. Intern Med., 267:44-53; Patil et al. (2008) Bioconjug. Chem., 19:1396-1403; Patil et al. (2009) Biomacromolecules 10:258-266; Schroeder et al. (2010) J. Intern. Med., 267:9-21; Taratula et al. (2009) J. Control Release 140:284-293; Martin et al. (2007) AAPS J., 9:E18-29). However, the developed delivery approaches address only selected siRNA delivery problems lacking optimal balanced delivery system that includes a solution for all the major aforementioned challenges. For example, a biodegradable polymer poly-L-lysine (PLL) is being used for gene delivery and its polyplexes are taken up into cells efficiently. However, transfection efficiencies of PLL-siRNA complexes remain several orders of magnitude lower when compared with other transfection agents. One potential reason for inefficient transfection has been identified as the lack of amino groups with a pKa ~5-7 for so called "proton sponge effect" that offers endosomolysis and subsequent release of siRNA. The desired transfection effect was achieved by structural modification of PLL using a targeting ligand or endosomolytic agents like chloroquine or fusogenic peptides (Martin et al. (2007) AAPS J., 9:E18-29; Read et al. (2005) Nucleic Acids Res., 33:e86). A significant improvement in transfection efficiency was observed when histidine or imidazole moieties were attached to the PLL (Benns et al. (2000) Bioconjug. Chem., 11:637-645; Midoux et al. (1999) Bioconjug. Chem., 10:406-411).

Another major challenge in the safe delivery of siRNA is its facile enzymatic degradation in cytoplasm due to the presence of nucleases that dramatically reduce siRNA half-life. It has been reported that internally quaternized and cancer-targeted polyamidoamine (PAMAM) dendrimers provide for the efficient cellular uptake and excellent gene silencing. It was shown that surface modification and internal quaternization of dendrimers reduced their cytotoxicity and substantially improved the cellular uptake while targeting of the dendrimers to cancer cells initiated receptor mediated endocytosis and led to the efficient gene knock down. The importance of free tertiary amine groups in dendrimers for endosomal escape has also been determined. Here, the design, synthesis, and evaluation of a triblock delivery system that provides solutions for major problems in siRNA delivery, i.e. poor cellular uptake, low endosomal escape, and facile enzymatic degradation, is provided. A novel triblock nanocarrier PAMAM-PEG-PLL has been designed to combine individual features of PAMAM dendrimer, polyethylene glycol (PEG) and poly-L-lysine. PAMAM dendrimer provides tertiary amines for endosomal escape; PEG covers up siRNA protecting it from enzymatic degradation; and PLL offers cationic amine groups for electrostatic interaction with negatively charged siRNA.

Methods

Materials

Generation four PAMAM-NH$_2$ dendrimers (Mw ~14,214 Da, 64 amine end groups), PLL.HBr (Mw ~12,000, degree of polymerization equal to 57), 4-(methylamino)pyridine and methyl iodide were purchased from Sigma-Aldrich Co. (St. Louis, Mo.). α,ω-Bis(2-carboxyethyl)polyethylene glycol (Mw ~3,000 Da) and N-(3-dimethylaminopropyl)-N-ethyl-carbodimide hydrochloride were obtained from Fluka (Allentown, Pa.). Spectra/Pore dialysis membranes were obtained from Spectrum Laboratories, Inc. (Rancho Dominguez, Calif.). Ethidium Bromide (EtBr) solution was purchased from Promega (Madison, Wis.). The sequence of siRNA targeted to BCL2 mRNA custom synthesized by Ambion (Austin, Tex.), was: 5'-GUG AAG UCA ACA UGC CUG C-dTdT-3' (sense strand; SEQ ID NO: 4) and 5'-GCA GGC AUG UUG ACU UCA C-dTdT-3' (antisense strand; SEQ ID NO: 5). Non-specific siRNA used as a negative control (sense strand, 5'-CCU CGG GCU GUG CUC UUU U-dTdT-3', SEQ ID NO: 10; antisense strand, 5'-AAA AGA GCA CAG CCC GAG G-dTdT-3', SEQ ID NO: 11) was received from Dharmacon Inc. (Lafayette, Colo.). Fluorescent RNA duplex—siRNA labeled with Pierce NuLight™ DY-547 fluorophores (siGLO Red Transfection Indicator, red fluorescence) was obtained from Applied Biosystems (Ambion, Inc., Foster City, Calif.). All other chemicals were purchased from Fisher Scientific (Fairlawn, N.J.).

Cell Line

The human ovarian carcinoma A2780 cell line was obtained from Dr. T. C. Hamilton (Fox Chase Cancer Center). Cells were cultured in RPMI 1640 medium (Sigma, St. Louis, Mo.) supplemented with 10% fetal bovine serum (Fisher Scientific, Fairlawn, N.J.). Cells were grown at 37° C. in a humidified atmosphere of 5% $CO_2$ (v/v) in air. All experiments were performed on cells in the exponential growth phase.

Synthesis of Surface Modified PAMAM Dendrimer (PAMAM-NHAc)

The surface modified and partially acetylated PAMAM-NHAc dendrimer was prepared as seen in FIG. 14 (Patil et al. (2008) Bioconjug. Chem., 19:1396-1403). Briefly, triethylamine (0.11 mL, 0.82 mmol) was added to a stirred solution of PAMAM-NH$_2$ generation four dendrimer (172 mg, 0.012 mmol) dissolved in anhydrous methanol (10 mL) followed by the addition of excess acetic anhydride (0.08 mL, 0.72 mmol). The resulting mixture was stirred at room temperature for 24 hours. Methanol was evaporated under reduced pressure and the resulting residue was dissolved in water (2 mL). Further purification by extensive dialysis against deionizer water using dialysis membrane (molecular mass cut off 2,000 Da) and freeze-drying afforded acetylated PAMAM dendrimer. The degree of acetylation was confirmed by proton nuclear magnetic resonance ($^1$H NMR).

Synthesis of PAMAM-PEG-COOH Conjugate

α,ω-Bis(2-carboxyethyl)polyethylene glycol (15 mg, 5 μmol, Mw ~3000 Da) and PAMAM-[(NHAc)$_{58}$(NH$_2$)$_6$] dendrimer (83 mg, 5 μmol) were dissolved in the mixture of anhydrous solvents methylene chloride (5 mL) and dimethyl sulfoxide (5 mL) (FIG. 14). After stirring for 10 minutes at room temperature, N-(3-dimethylaminopropyl)-N-ethylcarbodimide hydrochloride (EDC.HCl) (1 mg, 5.3 μmol) and 4-(methylamino)pyridine (DMAP) (0.5 mg) were added to the reaction mixture. The resulting mixture was stirred for an additional 36 hours at room temperature and solvents were removed under reduced pressure. The residue was dissolved in water and purified by extensive dialysis using Spectra/Por dialysis membrane (molecular weight cutoff, MWC=6,000 Da) against deionized water. The conjugate was further purified by passing through a sephadex G10 column using water as eluent and lyophilized to obtain PAMAM-PEG-COOH as a white solid.

Synthesis of PAMAM-PEG-PLL Conjugate

Triethylamine (0.2 mL) was added to a stirred solution of poly-L-lysine hydrobromide (22 mg, 1.83 μmole, Mw=~12,000, degree of polymerization equal to 57) in anhydrous dimethyl sulfoxide (3 mL) (FIG. 14). The reaction mixture was further diluted with anhydrous methylene chloride (5 mL) followed by the addition of PAMAM-PEG-COOH conjugate (22 mg, 1.14 μmol) and stirred at room temperature for 15 min. EDC.HCl (1.5 mg, 7.8 μmol) and DMAP (0.5 mg) were added to the reaction mixture. The resulting solution was stirred for an additional 36 hours at room temperature. The side product carbodimide urea was filtered off and solvents were removed under reduced pressure. The residue was dissolved in water and purified by extensive dialysis using Spectra/Por dialysis membrane (MWC=25,000 Da) against deionized water. The conjugate was further purified by passing through a Sephadex® G10 column using water as eluent and lyophilized to obtain PAMAM-PEG-PLL as a hygroscopic white solid.

Synthesis of PEG-PLL Conjugate

NHS-PEG-OMe (15.6 mg, 3.1 μmole, Mw=~5000) in phosphate buffer (pH 8.4) was added to a stirred solution of poly-L-lysine hydrobromide (22 mg, 1.83 μmole, Mw=~12000, degree of polymerization equal to 57) in phosphate buffer (pH 8.4). The resulting solution was stirred for 6 hours at room temperature. The resulting reaction mixture was then dialyzed against 1N HCl for 12 hours and subsequently extensively dialyzed against deionized water using dialysis membrane Spectra/Por (MWC=8,000 Da). Further purification by passing through sephadex G10 column using water as eluent and freeze drying afforded PEG-PLL conjugate.

Synthesis of PAMAM-PEG-PLL-Cy5.5

Cy 5.5 mono NHS ester (1.5 mg, 1.32 µmol) dissolved in anhydrous dimethyl sulfoxide (1 mL) was added to a stirred solution of PAMAM-PEG-PLL (9 mg, 0.32 µmol, Mw ~28,000) in 0.1 mM NaHCO$_3$ (1 mL). The resulting mixture was stirred in the dark at room temperature for 6 hours. Extensive dialysis using Spectra/Por dialysis membrane (MWC=25,000) against deionized water was carried out to remove unreacted Cy 5.5. Additionally, the conjugate was purified by passing through sephadex column. The concentration of Cy 5.5 dye attached to the PAMAM-PEG-PLL nanocarrier was estimated by measuring its fluorescence (Excitation 675 nm, emission 694 nm) using Cy 5.5 NHS ester as standard.

Proton Nuclear Magnetic Resonance Spectroscopy ($^1$H NMR)

$^1$H NMR was performed on a Varian VNMRS 400 MHz NMR spectrometer (Varian, Inc., Palo Alto, Calif.). The chemical shift was expressed as parts per million (ppm) and a solvent peak was used for reference (D$_2$O, 4.8 ppm). The following abbreviations are used in the results section to identify multiplicities of spectra peaks: s, singlet; m, multiplet; br, broad.

In Vitro Cytotoxicity

A modified MTT (3-(4,5-dimethylthiazol-2-yl)-2,5-diphenyltetrazolium bromide) assay was used to assess the cyctotoxicity of the following nanocarriers PEG, PLL, PEG-PLL, PAMAM-NH$_2$, PAMAM-OH, PAMAM-NHAc, and PAMAM-PEG-PLL as previously described (Jayant et al. (2007) Pharm. Res., 24:2120-2130; Pakunlu et al. (2004) Cancer Res., 64:6214-6224). To measure cytotoxicity, cells were separately incubated in a microtiter plate with different concentrations of PLL, PEG-PLL and PAMAM-PEG-PLL. Control cells received an equivalent volume of fresh medium. The duration of incubation was 24 hours. On the basis of these measurements, cellular viability was calculated for each nanocarrier concentration. A decrease in the cellular viability indicated an increase in the toxicity.

Characterization of siRNA Complexation with Nanocarriers

The complexes of cationic nanocarriers (PLL, PEG-PLL and PAMAM-PEG-PLL) and siRNA were prepared in water at N/P (amine/phosphate) charge ratios ranging from 0 to 1.5 and incubated at room temperature for 30 minutes. The charge ratio was calculated by relating the number of cationic primary amine groups on nanocarrier with the number of negatively charged phosphate groups of siRNA. Dendrimer-free siRNA was used as the control. Double-stranded RNA ladder (New England Biolabs, Ipswich, Mass.) with the smallest base pairs at 21 was used as a size reference. The samples were further diluted with DPBS buffer and electrophoresed in 4% agarose gel at 100 V for 50 min in Tris-Borate-EDTA buffer containing ethidium bromide. siRNA bands on the gel were visualized under ultraviolet light and photographed. Complex formation was also quantified by measuring fluorescence of ethidium bromide in the sample at 530 nm excitation and 590 nm emission wavelengths (Bolcato-Bellemin et al. (2007) Proc. Natl. Acad. Sci., 104:16050-5). The fluorescence intensity at N/P charge ratio equal to 0 was set to 100%.

Dynamic Light Scattering (DLS) Analysis and Zeta Potential

PAMAM-PEG-PLL-siRNA complex was prepared by mixing PAMAM-PEG-PLL and siRNA in water at N/P ratio equal to 3. The resulting complex was incubated for 30 minutes and the size was determined using the DynaPro-MS800 dynamic light scattering/molecular sizing instrument with argon laser wavelength λ=830 nm, a detector angle 90°, and typical sample volume of 20 µL. Each light scattering experiment consisted of 20 or more independent readings, 10 seconds in duration each. Data analysis was conducted using DynaPro Instrument Control Software for molecular Research DYNAMICS (version 5.26.60). The obtained DLS data represents the average of three runs. Zeta potential was measured on PALS Zeta Potential Analyzer (Brookhaven Instruments Corp, New York, N.Y.). Samples were taken as is and their volume was 1.5 mL. All measurements were carried out at room temperature. Each parameter was measured 5 times, and average values were calculated.

Cellular Internalization

Cellular uptake and intracellular localization of siRNA was investigated using a confocal microscopy. In this experiment, living cancer cells were incubated with fluorophore labeled naked siRNA (siGLO® Red, red fluorescence) and siRNA complexed with cationic nanocarrier PAMAM-PEG-PLL (N/P=3). Cellular uptake studied substances was monitored in living cells placed in a chamber at 37° C. within 1 hour. Cellular localization of siRNA was examined on fixed and washed cells after the incubation for 24 hours with the substances. Fluorescence and its distribution within the cell were examined using a confocal microscope.

Gene Expression

Reverse transcription-polymerase chain reaction (RT-PCR) was used for the analysis of gene expression (Pakunlu et al. (2004) Cancer Res., 64:6214-6224). The cationic nanonarriers (PLL, PLL-PEG-OMe and PAMAM-PEG-PLL)-siRNA (for BCL2 gene) complexes were added to the cells with the final concentration of siRNA equal to 1 µM. After 24 hours, total cellular RNA was isolated using an RNeasy kit (Qiagen, Valencia, Calif.). First-strand cDNA was synthesized by Ready-To-Go™ You-Prime First-Strand Beads (GE Healthcare, Piscataway, N.J.) with 2 µg of total cellular RNA and 100 ng of random hexadeoxynucleotide primer (Amersham Biosciences, Piscataway, N.J.). After synthesis, the reaction mixture was immediately subjected to polymerase chain reaction (PCR), which was carried out using GenAmp PCR System 2400 (Perkin-Elmer, Shelton, Conn.). β2-microglobulin (β2-m) was used as an internal standard. The following pairs of primers were used: BCL2: 5'-GGA TTG TGG CCT TCT TTG AG-3' (sense; SEQ ID NO: 6), 5'-CCA AAC TGA GCA GAG TCT TC-3' (antisense; SEQ ID NO: 7); β2-m (internal standard)-ACC CCC ACT GAA AAA GAT GA (sense; SEQ ID NO: 8), ATC TTC AAA CCT CCA TGA TG (antisense; SEQ ID NO: 9). PCR regimen was as follows: 94° C. for 5 minutes; 94° C. for 1 minute, 55° C. for 1 minute, and 72° C. for 1 minute for 41 cycles; and 60° C. for 10 minutes. PCR products were separated in 4% NuSieve 3:1 Reliant-agarose gels (Lonza, Basel, Switzerland) in 1× Tris-borate EDTA buffer [0.089 mol/L Tris-borate, 0.002 mol/L EDTA (pH 8.3); Research Organics Inc., Cleveland, Ohio] by submarine electrophoresis. The gels were stained with EtBr and digitally photographed.

Serum Stability of siRNA and PAMAM-PEG-PLL-siRNA Complex

Serum stabilities of naked siRNA and siRNA complexed with PAMAM-PEG-PLL nanocarrier were investigated by incubating siRNA or PAMAM-PEG-PLL-siRNA complex in 50% human serum at 37° C. Ten samples were prepared by mixing siRNA (30 nmol) in water with PAMAM-PEG-PLL (74.8 nmol, N/P=3) solution in water and separately incubated for 30 minutes at room temperature. In the case of naked siRNA, equal volume of RNAase free water was used instead of nanocarrier. To each of these samples 50% human plasma was added (final siRNA concentration was 1.43 nM) and incubated at 37° C. Samples were removed at an indicated time intervals (0, 0.25, 0.5, 0.75, 1, 3, 6, 12, 24 and 50 hours) and analyzed using a gel electrophoresis (4% agarose gel at 100V for 50 minutes) in Tris-Borate-EDTA buffer containing EtBr. siRNA bands on the gel were visualized under ultraviolet light. PAMAM-PEG-PLL-siRNA samples were pretreated with polymethacrylic acid to release free siRNA from cationic nanocarriers. 100 μL of polymethacrylic acid solution (4 μM) was added to the complexes (triblock nanocarrier/siRNA=3) and incubated at 37° C. with 50% human plasma. The released siRNA was then analyzed by a gel electrophoresis.

Statistical Analysis

Data obtained were analyzed using descriptive statistics, single factor analysis of variance (ANOVA) and presented as a mean value±standard deviation (SD) from five independent measurements. Data sets were analyzed for significance with Student's t test and considered P values of less than 0.05 as statistically significant.

Results

Delivery of siRNA into the cytoplasm of cancerous cells where it triggers sequence specific mRNA degradation has recently emerged as a powerful tool in the gene therapy. The major obstacles in safe transportation of siRNA have been extensively investigated and condensation to nanoparticles has now been recognized as the most efficient method for facile transport of siRNA. Therefore, designing a nanocarrier that enables effective and safe transfer of siRNA into mammalian cells is a task of great interest. In general, combining multiple functions in a single delivery system is a difficult task and requires laborious synthetic efforts. Herein, the design, synthesis, and evaluation of a synthetically simple yet novel triblock multifunctional nanocarrier PAMAM-PEG-PLL that effectively combines three functionalities which are otherwise ineffective when tested individually is described. The triblock nanonarrier PAMAM-PEG-PLL serves three distinct functions: (1) PLL provides cationic primary amine groups for electrostatic interaction with negatively charged siRNA (2) PAMAM dendrimer offers necessary tertiary amine groups for proton sponge effect, while (3) PEG confers nuclease stability in blood serum.

A three step synthetic route was used for the preparation of PAMAM-PEG-PLL nanocarrier (FIG. 14). In the first step, PAMAM dendrimer was partially acetylated to afford PAMAM-[(NHAc)$_{58}$(NH$_2$)$_6$] dendrimer. The second step involved synthesis of PAMAM-PEG-COOH by reacting one of the acid group of α,ω-bis(2-carboxyethyl)polyethylene glycol (Mw=~3000) with one of the primary amine of PAMAM-[(NHAc)$_{58}$(NH2)$_6$] dendrimer. One could expect that the length of the PEG block would have great influence on the final triblock-siRNA complex as a shorter length might not be enough to protect siRNA from the enzymatic degradation. Instead of using a single long PEG chain length a medium size chain (MW 3000) was used, while the ratio of triblock nanocarrier/siRNA was taken as 3 (N/P=3). Thus, a single siRNA is surrounded by 3 PEG blocks and expected to give effective protection. Previously, the cellular penetration of PEG with different molecular weight (up to MW 20000 Da) was tested and it was found that PEG with MW around 3000 Da penetrate cells faster when compared with higher MW polymers (Chandna et al. (2007) Mol. Pharm., 4:668-78). Based on these considerations, PEG with MW 3000 Da was selected. During the third step, terminal free acid group of PAMAM-PEG-COOH was reacted with PLL using EDC as a coupling reagent.

One can assume that the synthetic procedure used could not be selective and the design led to some cross-linking reactions. However, the instant synthetic scheme can be selective because it is a sequential procedure and the following reasons contribute to the selective formation of PAMAM-PEG and not a PAMAM-PEG-PAMAM cross-linking polymer: (1) PAMAM-NHAc has only 5-6 free amines to react with the PEG-dicarboxylic acid; (2) the free amine groups on dendrimer are crowded with NHAc substituent and not easily available for cross-linking; (3) dilution of reaction also plays an important role in reducing the cross-linking reaction; (4) this reaction greatly differs from the usual small molecules where selectivity would be an issue; (5) in the present studies, more harsh conditions, prolonged reaction time, and more equivalents of coupling reagents would be required to force the cross-linking PAMAM-PEG-PAMAM reaction; (6) the technique of filtering the reaction mixture after coupling reaction was followed to remove any insoluble material, however, in this reaction, negligible amount of insoluble material was formed; (7) even if the cross-linking product is formed, it was in trace amount and removed completely during filtration. The coupling reaction of PAMAM-PEG with PLL can be selective to form the desired PAMAM-PEG-PLL as PLL has several amine groups available to react in comparison with 5-6 amine groups of PAMAM dendrimer. The $^1$H-NMR was very useful and informative in determining the content of nanocarrier. The area under peak would greatly vary (almost double or half) if the number of units (PAMAM, PEG and PLL) changes in the final nanocarrier. Each block has a large number of protons and cannot be ignored.

Theoretically, there might be a possibility that some molecules of siRNA could form complexes directly with the PAMAM dendrimer, not with positively charged PLL. The PAMAM dendrimer used in present study was surface modified and lacks free primary amine groups required to form complex with siRNA. As $^1$H-NMR studies show, very few (~5-6) free amines are available on the PAMAM dendrimer. Such an amount is not enough to form complexes with siRNA that possess about 42 negatively charged phosphate groups. It has been suggested that tertiary amines in PAMAM dendrimer do not participate in direct complexation with siRNA and stable complex is formed only after quaternizing the internal tertiary amine groups (Patil et al. (2009) Biomacromolecules 10:258-266). This supports the fact that PAMAM dendrimer would not form complex with siRNA.

Figure 15C:
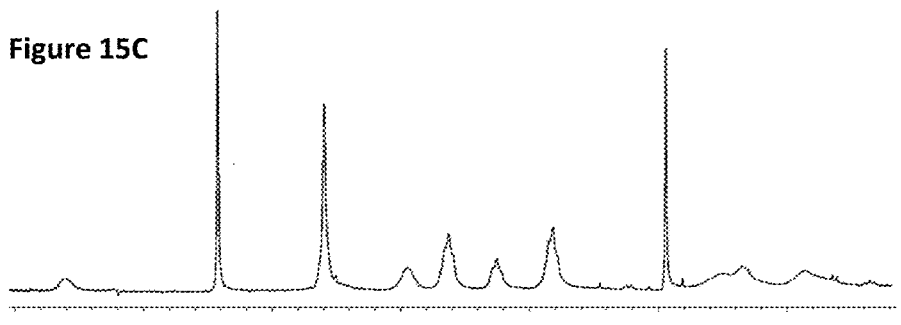
Figure 15D:
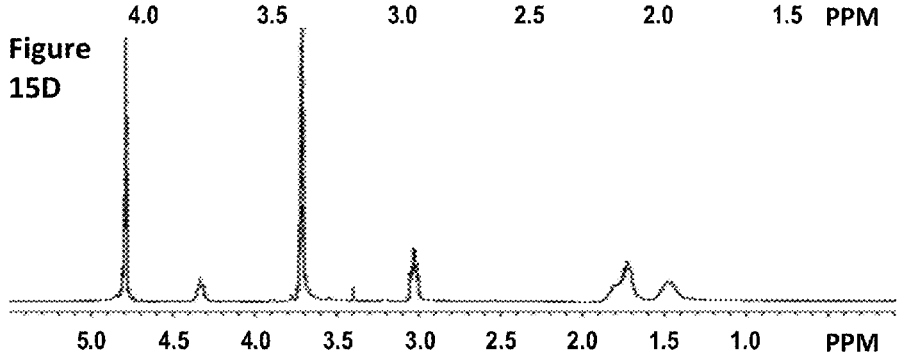

The following three matrix compounds were used to record MALDI-TOF: sinapinic acid, α-cyano-4-hydroxycinnamic acid, and 2,5-dihydroxybenzoic acid. More than likely, the triblock nanocarrier did not ionize under the attempted conditions. All proton NMR spectra were recorded in solution of studied compounds in D$_2$O using a 400 MHz NMR spectrometer. The chemical shift (δ) was expressed as parts per million (ppm). The data obtained confirmed the structures of synthesized substances. PAMAM-NHAc $^1$H NMR spectral data are shown in FIG. 15A. The following peaks were identified: δ 1.98 (s, COCH$_3$), 2.40-2.50 (br m, CH$_2$CONH), 2.62-2.73 (br m, CONHCH$_2$CH$_2$N), 2.82-2.92 (br m, NCH$_2$CH$_2$CONH), 3.26-3.37 (m, CONHCH$_2$ and CH$_2$NHCOCH$_3$). The degree of acetylation (~90%) was confirmed from the proton NMR spectra (FIG. 15A) by calculation the ration between the integrated peak area of signal appeared at δ 1.98 ppm (—NH-COCH$_3$) to that of methylene protons of PAMAM dendrimer (δ 2.40-3.37). PAMAM-PEG-COOH $^1$H NMR spectrum (FIG. 15B) showed the following peaks: δ 2.00 (s, COCH$_3$), 2.40-2.50 (br m, CH$_2$CONH), 2.64-2.75 (br m, CONHCH$_2$CH$_2$N), 2.82-2.92 (br m, NCH$_2$CH$_2$CONH), 3.30-3.38 (m, CONHCH$_2$ and CH$_2$NHCOCH$_3$), 3.74 (s, —CH$_2$CH$_2$O). The spectra showed mono acylation of dendrimer with α,ω-bis(2-carboxyethyl)polyethylene glycol leaving another —COOH group free for conjugation with poly-L-lysine (PLL). The $^1$H-NMR spectra for this compound confirmed the presence of both polyethylene glycol and dendrimer protons. Further mono functionalization was determined by calculating the area under proton peaks arising from polyethylene glycol (Mw=~3000, —CH$_2$CH$_2$O—, ~270H) and dendrimer (—COCH$_3$, 174H) appeared at δ 3.74 and δ 2.00, respectively. PAMAM-PEG-PLL $^1$H-NMR spectral data are shown in FIG. 15C. The following peaks were identified: δ 1.30-1.50 (br m, PLL), 1.60-1.90 (br m, PLL), 1.98 (s, PAMAM), 2.40-2.50 (br m, PAMAM), 2.60-2.70 (br m, PAMAM), 2.78-2.88 (br m, PAMAM), 2.90-3.05 (br m, PLL), 3.26-3.37 (m, PAMAM), 3.70 (s, PEG), 4.25-4.35 (br m, PLL). The spectra confirmed the formation of PAMAM-PEG-PLL nanocarrier showing the presence of proton peaks arising from dendrimer (PAMAM), polyethylene glycol (PEG) and poly-L-lysine (PLL). PEG-PLL $^1$H-NMR spectrum (FIG. 15D) showed the following peaks: δ 1.38-1.60 (br m, —CH$_2$—CH$_2$—CH$_2$—), 1.68-1.90 (br m, —CH$_2$—CH$_2$—CH(CO)NH— & —CH$_2$—CH$_2$—CH$_2$NH$_2$—), 2.90-3.10 (br m, —CH$_2$—CH$_2$NH$_2$—), 3.70 (s, —CH$_2$CH$_2$O PEG), 4.30-4.40 (br m, —CH$_2$—CH$_2$—CH(CO)NH—). $^1$H-NMR technique has been widely used and documented as one of the best method for calculating the functional group content of dendrimers. The number of amine groups left free after acetylation reaction can be calculated using the $^1$H-NMR technique (Majoros et al. (2003) Macromolecules 36:5526-5529). Since the triblock nanocarrier is a combination of linear as well as spherical polymer, it will not follow the behavior of the conventional polymer molecules and therefore, the conventional molecular weight determination method based on calibration cannot be used in such cases. More studies and special set-ups are required to use the Gel Permeation Chromatography (GPC) method to determine the molecular weight. It was found that $^1$H-NMR spectroscopy was highly useful and provided the desired information by comparing the area under peak. The number of free amines in the PAMAM-PEG-PLL nanocarrier was calculated based on the degree of polymerization in the poly-L-lysine polymer. There could be a very small variation in the calculated and actual content of functional group in the nanocarrier however it would not greatly affect its function. Gel-electrophoresis studies also provided indirect evidence on accuracy of calculated content of functional group in triblock nanocarriers. The band for siRNA was completely disappeared when the ratio of N/P was 1, i.e., the number of cationic amines/phosphate of siRNA is 1/1. If the calculated amount of cationic amines is not correct the nanocarrier/siRNA complex formation can be expected at different N/P ratio (—NH$_2$ of nanocarrier/phosphate of siRNA).

The measurement of viability of cells incubated with different concentrations of PEG, PLL, PEG-PLL, PAMAM-NHAc-PEG and PAMAM-NHAc-PEG-PLL compounds showed their relatively low cytotoxicity (FIG. 16A). No substantial differences were found between different nanocarriers under the concentrations of the compounds lower than 4 μM. However, the concentrations exceed 4 μM, PEG-PLL demonstrated higher cytotoxicity when compared with PLL alone and PAMAM-NHAc-PEG-PLL. Therefore, the toxicity of PEG-PLL was reduced when PEG-PLL was conjugated to PAMAM-NHAc dendrimer. Cytotoxicity data for the triblock PAMAM-NHAc-PEG-PLL nanocarrier were compared with cytotoxicity of its previously synthesized predecessors (PAMAM-NH$_2$, PAMAM-OH, and PAMAM-NHAc dendrimers) (Patil et al. (2008) Bioconjug. Chem., 19:1396-1403). The results of such comparison showed a comparably low cytotoxicity for triblock PAMAM-NHAc-PEG-PLL and acetylated PAMAM-NHAc dendrimers. The cytotoxicity under the high concentrations of both dendrimers was lower when compared with quaternized non-acetylated PAMAM-OH dendrimer. In contrast, non-modified PAMAM-NH$_2$ dendrimer demonstrated a significant cellular toxicity under the concentrations higher than 5 μM. It should be stressed that a maximum decrease in viability of cells incubated with PEG, PLL, PEG-PLL, PAMAM-NHAc-PEG-PLL, PAMAM-OH, and PAMAM-NHAc compounds was substantially higher than 50% under all studied concentrations. Such low toxicity does not allow calculating the IC$_{50}$ dose for these substances (half maximal inhibitory concentration, the dose that kills about 50% of cells). In contrast, the IC50 dose of non-modified PAMAM-NH$_2$ dendrimer was estimated to be around 6 μM (FIG. 16A).

The nanocarrier-siRNA complex formation and optimal N/P ratio was determined by agarose gel electrophoresis. The PLL, PEG-PLL and PAMAM-PEG-PLL nanocarriers were mixed with siRNA in water at various N/P charge ratios and were subjected to electrophoresis in agarose gel (FIG. 16B). The numbers of cationic primary amine groups in PLL, PEG-PLL and PAMAM-PEG-PLL were calculated based on PLL Mw (~8,000) and degree of polymerization (57). All three nanocarriers showed the complex formation at N/P ratio 1 and above as evidenced by oligonucleotide bands disappearance from agarose gels. The quantitative analysis showed that fluorescence of PLL-siRNA, PEG-PLL-siRNA and PAMAM-PEG-PLL-siRNA progressively decreased with the increase in N/P ratio. For PLL-siRNA, the complexation decreased fluorescence to 19%, 8% and 0% with N/P ratio equal to 0.5, 1.0, 1.5 relative units, respectively; for PEG-PLL-siRNA, fluorescence decreased to 19%, 8%, 0% with N/P ratio equal to 0.5, 1.0, 1.5 relative units, respectively; for PAMAM-PEG-PLL-siRNA, fluorescence decreased to 45%, 0% with N/P ratio equal to 0.5, 1.0, respectively.

The hydrodynamic diameter of PAMAM-PEG-PLL-siRNA complex was determined by dynamic light scattering at charge ratio ranging from 1 to 3 rel. units. The PAMAM-PEG-PLL/siRNA particle size slightly decreased with increasing the charge ratio to 3 relative units (FIG. 16C). The measurements of zeta potential of dendrimer-siRNA complexes showed that the complexes were neutral. The size of PAMAM-PEG-PLL-siRNA complexes used in this paper varied from 120 to 180 nm depending on N/P ratio. This relatively large size is attributed to cross-linking of nanocarrier and siRNA. It has been shown that an internally charged dendrimer gives small, compact, and spherical nano-particles with siRNA. However, commercial PAMAM-NH$_2$ showed nano-fibers due to cross-linking (Chandna et al. (2007) Mol. Pharm., 4:668-78). In the present experiments, a similar trend is expected because PLL possess primary amine groups.

The cellular uptake of naked and complexated fluorophore labeled siRNA (siGLO® Red, red fluorescence) was studied in living (not washed and fixed) cells using confocal microscopy. A2780 human ovarian cancer cells were incubated with free siRNA and PAMAM-PEG-PLL-siRNA complex, and were subjected to confocal microscopy. Naked siRNA did not penetrate the cancer cells (FIG. 17A). It has been reported that PAMAM-NH$_2$ and PAMAM-OH dendrimers failed to deliver siRNA into cells, while the acetylation of PAMAM dendrimer surface substantially improved internalization of PAMAM-siRNA complexes (Patil et al. (2008) Bioconjug.

Chem., 19:1396-1403). Based on this finding, a PAMAM dendrimer with the acetylated surface further modified with PEG and PLL was used. It was found that siRNA complexated with a PAMAM-PEG-PLL cationic nanocarrier provided excellent cellular uptake (FIG. 17B). Moreover, optical sections z-series of a single living cell showed the homogenous and uniform distribution of siRNA-dendrimer complex in different cellular layers from the top of cell to the bottom (FIG. 17C). All experiments were performed on living cells without staining, fixation, and washing out the media with fluorescently labeled siRNA-dendrimer complexes. Because of this one can see red fluorescence both inside the cells and media. In contrast naked siRNA could be seen just in the media but not in the cell (FIG. 17A). The stability of siRNA in the blood serum was determined by incubating siRNA either naked or complexed with PAMAM-PEG-PLL nanocarrier in the human blood serum (FIG. 18). As expected, naked siRNA started to degrade after 1 hour of incubation and completely degraded within 12 hours. In contrast, complexation of siRNA to PAMAM-PEG-PLL nanocarrier protected siRNA from the nuclease degradation; even 48 hours after the incubation of complexated siRNA with human blood serum, siRNA remained nondegraded. Therefore the proposed complexation of siRNA with PAMAM-PEG-PLL prevents the degradation of siRNA in the plasma.

The gene knockdown efficiency of siRNA delivered by Poly-L-Lysine (PLL), PEG-PLL, PAMAM, PAMAM-PEG and PAMAM-PEG-PLL nanocarriers with appropriate controls (fresh media, naked specific siRNA, naked non-specific siRNA with scrambled sequence and non-specific siRNA delivered by PAMAM-PEG-PLL nanocarrier) was investigated using quantitative RT-PCR. BCL2 protein responsible for cellular antiapoptotic defense was selected as a target for siRNA. The results of these experiments are shown in FIG. 19. It was found that siRNA delivered by PAMAM, PAMAM-PEG, PLL, and PEG-PLL nanocarriers lowered the expression of the targeted gene approximately up to 70-50% from its control value (FIG. 19, bars 2, 3, $P<0.05$). In contrast, delivery of siRNA by a PAMAM-PEG-PLL triblock nanocarrier led to a significant suppression of the expression of the targeted BCL2 gene down to 20% from the control value ($P<0.05$). The decrease in gene expression after incubation with PAMAM-PEG-PLL-siRNA was statistically significant ($P<0.05$) when compared with either PLL-siRNA or PEG-PLL-siRNA complexes. It should be stressed that naked BCL2-specific siRNA, naked non-specific siRNA and non-specific BCL2 siRNA conjugated with PAMAM-PEG-PLL did not influenced on the expression of BCL2 mRNA.

Studies on PLL as a cationic nanocarrier for gene transfection efficiency revealed that PLL alone provides relatively low gene knockdown, which is attributed to the lack of tertiary amine groups for the so called proton sponge effect. It is believed that this effect plays a substantial role in endosomal escape of siRNA inside cells after endocytosis (Inoue et al. (2008) J. Control Release 126:59-66; Kano et al. (2011) J. Control Release 149:2-7; Nel et al. (2009) Nat. Mater., 8:543-557). Nevertheless, PLL in combination with proton sponge ligands such as imidazole or histidine effectively reduced the gene expression. However, the toxicity of PLL dramatically decreased when imidazole or histidines were attached to PLL (Benns et al. (2000) Bioconjug. Chem., 11:637-645; Midoux et al. (1999) Bioconjug. Chem., 10:406-411). In the present investigation, a combination of PLL with a nontoxic PAMAM-NHAc dendrimer that possess several internal tertiary amine groups is provided. These groups will induce osmotic swelling of the endosome due to endosomal buffering and lead to the rupture of endocytotic vesicles and subsequent release of their payload. Furthermore, polyethylene glycol (PEG) was included in the nanocarrier to enhance siRNA stability against nuclease enzymes during the voyage in the human blood stream. A decrease in cytotoxicity of PLL by attaching a nontoxic PAMAM-NHAc dendrimer and polyethylene glycol was achieved.

The ability of PLL, PEG-PLL and PAMAM-PEG-PLL to form complex with siRNA was compared using agarose gel electrophoresis method. All three nanocarriers formed a stable complex at N/P ratio 1 and above. The numbers of cationic primary amine groups were calculated based on PLL molecular weight and degree of polymerization (~8000 Da and 57, respectively). Each PAMAM-PEG-PLL carrier (calculated Mw 27650 Da) contained approximately 56 primary amine groups. Similarly, cationic groups for PEG-PLL (calculated Mw 11,000 Da, DP 57) and PLL (Mw 8000 Da, DP 57) were calculated as 56 and 57 respectively. As expected, the agarose gel electrophoresis data showed that PAMAM-PEG-PLL showed similar to PEG-PLL and PLL ability to form complexes with siRNA. Dynamic light scattering data revealed an average size around 150 nm of the resulting complexes of the proposed nanocarriers with siRNA. This size of the resulting nanoparticles and possible impact of PLL as penetration enhancer resulted in the efficient cellular uptake of triblock nanocarrier PAMAM-PEG-PLL-siRNA complexes by human cancer cells.

However, effective uptake of siRNA by cells does not automatically ensure effective silencing of its targeted mRNA. For instance, previously, it has been shown that an effective intracellular delivery of siRNA by dendrimers does not guarantee its high gene silencing activity (Patil et al. (2008) Bioconjug. Chem., 19:1396-1403; Patil et al. (2009) Biomacromolecules 10:258-266). Down regulation of specific gene by siRNA can be controlled by two possible contributing factors (1) effective cellular internalization of siRNA and (2) endosomal escape of the payload to perform the task. Some cationic polymers used for siRNA delivery including PLL polymer show an excellent penetration into the cells, while demonstrating a relatively weak gene knockdown due to poor endosomal release of the siRNA payload (Hwang et al. (2001) Curr. Opin. Mol. Ther., 3:183-191). The PAMAM dendrimer unit in the triblock of the proposed nanocarrier PAMAM-PEG-PLL provides the required tertiary amines for proton sponge effect and subsequent endosomal release of the siRNA. The proton sponge effect is only one possible mechanism of the release of siRNA from the complex. The following mechanisms can potentially be involved in the intracellular release of siRNA. First, siRNA-carrier complex enters the cells by endocytosis in membrane limited endosomes that eventually fuse with lysosomes. This leads to the sharp decrease in pH disrupting electrostatic interactions between the nucleic acid and carrier and ultimately leading to the siRNA release. Secondly, lysosomal enzymes and the acidic environment can either degrade or swell polymers stimulating the release siRNA from the nanoparticle (Gary et al. (2007) J. Control Release 121:64-73). Thirdly, polymers can themselves possess some membrane disruptive properties. They can swell and burst the endosome through protonation of excess amine groups (Putnam et al. (2001) Proc. Natl. Acad. Sci., 98:1200-5).

Thus, PAMAM-PEG-PLL nanocarrier fulfills both the requirements of an effective delivery system of improved penetration and delivery of siRNA to the cytoplasm to achieve desired gene knockdown. The role of the PAMAM dendrimer was confirmed by comparing the gene silencing efficiency of BCL2 gene of siRNA complexed with triblock PAMAM-PEG-PLL, PLL and PEG-PLL nanocarriers. Indeed the triblock nanocarrier PAMAM-PEG-PLL-siRNA showed maximum suppression of the expression of targeted BCL2 gene while PLL alone or in combination with poly(enthylene glycol) (PLL-PEG) led to a substantially lower decrease in the expression of this gene.

After confirming the role of PLL and PAMAM in the triblock nanocarrier PAMAM-PEG-PLL, the role of PEG to protect the siRNA during the voyage in the human blood stream was examined. Nuclease enzyme degradation of siRNA in the blood serum is one of the major obstacles for the in vivo therapeutic applications of the siRNA. PEGylation of siRNA or nanocarriers greatly improved the stability of the siRNA in the human blood serum (Kim et al. (2006) J. Control Release 116:123-129; Merkel et al. (2009) J. Control Release 138:148-159; Sato et al. (2007) J. Control Release 122:209-216; Schiffelers et al. (2004) Nucleic Acids Res., 32:e149; Taratula et al. (2009) J. Control Release 140:284-93). Though the exact mechanisms of such stabilization are not clear, one can assume that siRNA is shielded by a linear polymer polyethylene glycol and thus minimizes its exposure to the nuclease enzymes. This assumption is based on the following considerations. Although, PEG is a middle block of the nanocarrier, it is also a hydrophilic segment and therefore one can expect a micelle like geometry of the complex. The triblock nanocarrier on complexation with siRNA may form micelle wherein the hydrophilic region (PEG) encapsulates PLL/siRNA complex. As expected, siRNA complexed with the proposed triblock nanocarrier PAMAM-PEG-PLL showed excellent siRNA stability in human blood serum. In fact, complexated siRNA was stable in the human serum more than 48 hours, while naked siRNA degraded in less than 6 hours.

A triblock nanocarrier was designed, synthesized, and evaluated for the efficient delivery of siRNA. The multifunctional triblock nanocarrier is synthetically simple to prepare and provide a solution to several obstacles involved in therapeutic applications of siRNA.

Example 4

CD44 (Cluster of Differentiation 44) is a type I transmembrane protein and a member of the cartilage link protein family. It is involved in cell-cell and cell-matrix interactions and signal transduction. CD44 is one of the major determinants of multidrug resistance and metastases in many types of cancers. CD44 binds to hyaluronic acid found in all types of extracellular matrices and is a major constituent of the peritoneum, a common site for ovarian cancer metastases. It has been found that this protein is overexpressed in several types of gynecological cancers, especially in tumor tissues of patients with ovarian carcinoma (FIG. 20). Moreover its expression in tumor tissue statistically significantly exceeds the expression in normal tissue of the same organ and from the same patient. Consequently, CD44 protein may be suppressed in cancer cells in order to enhance the efficacy of chemotherapy of primary cancer and prevent the development of metastases.

Naked siRNA targeted to CD44 and scrambled siRNA were not efficient in such suppression (FIG. 21). However, anti-CD44 siRNA delivered with a special carrier—PPI dendrimer led to the suppression the expression of CD44 protein in cancer cells isolated from ascetic fluid taken from patients with metastatic ovarian cancer. Targeting of PPI dendrimer to cancer cells by LHRH peptide substantially enhanced the suppression of this protein by the delivered siRNA. The gene expression data obtained using quantitative reverse transcription PCR (FIG. 21) were confirmed by registration of protein expression using fluorescence microscopy (FIG. 22). In the later experiments, CD44 proteins were labeled with anti-CD44 antibody (red fluorescence) while cellular nuclei were labeled by nuclear stain (blue fluorescence). In non treated cancer cells, CD44 proteins are overexpressed predominately in the plasma membrane. Treatment of cancer cells with LHRH peptide-targeted PPI dendrimer containing anti-CD44 siRNA substantially decreased the expression of CD44 in the plasma membrane of cancer cells. Measurement of cytotoxicity of paclitaxel (FIG. 23) showed that the delivery of this drug by PPI dendrimer and simultaneous suppression of CD44 protein substantially enhanced cytotoxicity of the drug.

Example 5

The ability of short interfering RNA (siRNA) to silence specific genes inspired the use of siRNA as a therapeutic agent for a wide spectrum of disorders including cancer, infectious diseases, and metabolic disturbances (Devi, G. R. (2006) Cancer Gene Therapy 13:819-829; Garbuzenko et al. (2009) Pharmaceutical Res., 26:382-394; Chang et al. (2006) Gene Therapy 13:871-872; Rozema et al. (2007) Proc. Natl. Acad. Sci., 104:12982-12987; Betigeri et al. (2006) Mol. Pharm., 3:424-430). The main advantages of RNA interference compared to other therapeutic approaches include exceptional specificity of siRNA, high potency of gene silencing, and the ability to target virtually any expressed gene (Dykxhoorn et al. (2005) Ann. Rev. Med., 56:401-423; Uprichard, S. L. (2005) FEBS Lett., 579:5996-6007). However, the low penetration ability of naked siRNA into the cellular cytoplasm to induce sequence-specific mRNA degradation represents a primary obstacle limiting the success of siRNA therapy (Uprichard, S. L. (2005) FEBS Lett., 579: 5996-6007; Gary et al. (2007) J. Controlled Release 121:64-73; Ikeda et al. (2006) Pharm. Res., 23:1631-1640; Akhtar et al. (2007) J. Clin. Invest., 117:3623-3632; Crombez et al. (2007) Biochem. Soc. Trans., 35:44-46). Despite extensive research, an efficient, nontoxic gene delivery approach has not yet been developed. It is recognized that the delivery of the nucleic acid by nanocarriers facilitates the cellular uptake of DNA/siRNA and increases their gene silencing ability (Medarova et al. (2007) Nat. Med., 13:372-377; Patil et al. (2008) Bioconjugate Chem., 19:1396-1403; Saad et al. (2008) Nanomed., 3:761-776). Viruses have been studied as gene delivery vectors; however, the immune response elicited by viral capsid proteins represents a major challenge limiting the wide use of this approach (Bessis et al. (2004) Gene Ther., 11:S10-S17). Consequently, considerable interest to the development of nonviral gene delivery vehicles has been generated. In order to provide effective gene silencing, two controversial requirements for such delivery systems should be satisfied: (1) stability of siRNA carrier complex during its journey in the systemic circulation toward the targeted cells and the protection of the payload against the aggressive biological environment and (2) intracellular availability of the nucleic acids in order to permit desired therapeutic effects within the cells (Gary et al. (2007) J. Controlled Release 121:64-73; Ogris et al. (1999) Gene Ther., 6:595-605; Oupicky et al. (2001) Gene Ther., 8:713-724; Taratula et al. (2009) J. Controlled Release 140:284-293).

In order to optimize the delivery of siRNA and enhance the efficiency of the treatment, it is highly desirable to employ clinically relevant imaging approaches for in-situ monitoring of the disease progression and therapeutic responses (Medarova et al. (2007) Nat. Med., 13:372-377). Magnetic Resonance Imaging (MRI) is a powerful tool for non-invasive in vivo monitoring due to its high resolution and lack of ionizing radiation (Wang et al. (2008) CA Cancer J. Clin., 58:97-110; Atri, M. (2006) J. Clin. Oncol., 24:3299-3308). Superparamagnetic Iron Oxide (SPIO) nanoparticles have been widely investigated as MRI contrast agents to enhance images of biological molecules (Thorek et al. (2006) Ann. Biomed. Engin., 34:23-38; Lee et al. (2009) Angew. Chemie-Intl. Ed., 48:4174-4179). Moreover, several approaches have been reported for both siRNA and DNA delivery based on SPIO nanoparticles to timely monitor the delivery process and also to evaluate the therapeutic effects (Medarova et al. (2007) Nat. Med., 13:372-377; Boyer et al. (2010) J. Mater. Chem., 20:255-265; Pan et al. (2007) Cancer Res., 67:8156-8163). However, these methods have various shortcomings and do not allow a balanced optimization of siRNA compaction, endosomal escape, and dissociation from the nanoparticles. For example, covalently linked siRNA molecules to the SPIO surface and demonstrated the feasibility of using SPIO nanoparticles as MRI enhancers for in vivo tracking of tumor uptake and silencing effects of the siRNA (Medarova et al. (2007) Nat. Med., 13:372-377). However, siRNA molecules in this study are tethered to the nanoparticles through chemical bonds between the siRNA and SPIO nanoparticles. Consequently, it is highly possible that such chemical conjugations might potentially compromise the silencing effects of siRNA. Moreover, a chemical conjugation might also limit the siRNA loading capacity of the SPIO nanoparticles. In addition, cellular uptake of existing SPIO-siRNA complexes is not limited only to the targeted cells. Consequently, such non-targeted complexes can be internalized by virtually any cells in the body. This nonspecific delivery of siRNA can result in serious adverse side effects on healthy tissues and limit clinical applications of this approach (Ikeda et al. (2006) Pharm. Res., 23:1631-1640; Oliveira et al. (2006) J. Biomed. Biotech., 2006:63675; Kim et al. (2007) Biotech. Prog., 23:232-237). In particular, delivery of anticancer drugs, genes, and imaging agents specifically to primary tumor and distant metastases requires the use of a ligand specific to receptors that are overexpressed in cancer cells (Ikeda et al. (2006) Pharm. Res., 23:1631-1640; Oliveira et al. (2006) J. Biomed. Biotech., 2006:63675; Kim et al. (2007) Biotech. Prog., 23:232-237; Taratula et al. (2009) J. Controlled Release 140:284-293; Kularatne et al. (2010) Methods Mol Biol., 624:249-265). Previously, it has been shown that many cancer cells overexpress receptors to Luteinizing Hormone-Releasing Hormone (LHRH) (Dharap et al. (2003) Pharm. Res., 20:889-896; Dharap et al. (2003) J. Controlled Release 91:61-73). A combination of anticancer drugs and LHRH peptide in one delivery system enhanced the efficacy of chemotherapy and decreased the adverse side effects of treatment to healthy organs (Chandna et al. (2007) Mol. Pharm., 4:668-678; Dharap et al. (2005) Proc. Natl. Acad. Sci., 102:12962-12967; Saad et al. (2008) J. Control Release 130:107-114).

Herein, the development and characterization of a complex tumor-targeted Drug Delivery System (DDS) for the simultaneous delivery of siRNA and MRI contrast agents (SPIO) specifically to cancer cells is provided. The ability of small (~5 nm) SPIO nanoparticles was used to cooperatively form complexes of siRNA with Polypropyleneimine Generation 5 (PPI G5) dendrimers, which are highly branched three-dimensional polymers with defined molecular weight and a large number of peripheral functional groups (Taratula et al. (2009) J. Controlled Release 140:284-293). To integrate tumor-specific targeting moiety and increase steric stability, the formulated siRNA nanoparticles were modified with heterobifunctional Poly(ethylene glycol) (PEG). The distal end of PEG was coupled with a synthetic analog of LHRH decapeptide as a targeting agent.

Methods
Materials

Polypropylenimine Tetrahexacontaamine Dendrimer Generation 5 (PPI G5), 2,4,6-Trinitrobenzenesulphonic Acid (TNBSA), oleic acid, 1-octadecene, Poly (Maleic Anhydride-alt-1-Octadecene) (PMAO, MW=30,000-50,000 Da), Poly (Diallyldimethylammonium chloride) (PDDA, MW 120,000 Da), microsized iron (III) oxide, Sodium Dodecyl Sulfate (SDS), and (4-(2-Hydroxyethyl)-1-piperazineethanesulfonic acid) (HEPES) were obtained from Sigma-Aldrich and used without further purification. Ethidium Bromide (EtBr) solution and α-Maleimide-ω-N-hydroxysuccinimide ester Poly (ethylene glycol) (MAL-PEG-NHS) were purchased from Promega (Madison, Wis.) and NOF Corporation (White Plains, N.Y.), respectively. The sequence of antisense of siRNA targeted to BCL2 mRNA (obtained from Ambion, Austin, Tex.), was 5'-GUGAAGUCAACAUGCCUGC-dTdT-3' (sense strand; SEQ ID NO: 4) and 5'-GCAGGCAU-GUUGACUUCAC-dTdT-3' (antisense strand; SEQ ID NO: 5). The non-targeted mock siRNA (negative control) (5'-CCUCGGGCUGUGCUCUUUU-dTdT-3' sense strand, SEQ ID NO: 10) and 5'-AAAAGAGCACAGCCCGAGG-dTdT-3' antisense strand, SEQ ID NO: 11), 5 carboxy-fluorescein (FAM) labeled siRNA were obtained from Applied Biosystems (Ambion, Inc., Foster City, Calif.). A synthetic analog of LHRH, Lys6-des-Gly10-Pro9-ethylamide (Gln-His-Trp-Ser-Tyr-DLys(DCys)-Leu-Arg-Pro-NH-Et' SEQ ID NO: 3) peptide was synthesized by Amersham Peptide Co. (Sunnyvale, Calif.) (Dharap et al. (2003) J. Controlled Release 91:61-73; Chandna et al. (2007) Mol. Pharm., 4:668-678; Dharap et al. (2005) Proc. Natl. Acad. Sci., 102:12962-12967; Saad et al. (2008) J. Control Release 130:107-114). All other chemicals were purchased from Fisher Scientific (Fairlawn, N.J.). Cisplatin (CIS) was purchased from Sigma (St. Louis, Mo.).

Superparamagnetic Iron Oxide (SPIO) Nanoparticles Preparation

Iron oxide nanocrystals of 5 nm in diameter were synthesized in organic solvents at high temperature. Typically, microsized iron oxide was mixed with oleic acid, 1-octadecene, and then heated to 320° C. for a certain time to produce monodisperse (5-10% size distribution) iron oxide nanocrystals. The size of nanoparticles was controlled by reaction time, temperature, and the iron oxide and oleic acid concentrations. After the reaction was completed, the mixture was cooled and the iron oxide nanocrystals were precipitated out of 1-octadecene by chloroform/acetone, and then re-dispersed in chloroform. These nanocrystals were highly crystalline and uniform but were not soluble in water due to the hydrophobic oleic acid capping layer. For solubilization of iron oxide nanoparticles in water, a modified method based on forming micelles through amphiphilic polymers (PMAO) for transferring iron oxide nanocrystals from organic solvents into water was used (Yu et al. (2006) Nanotech., 17:4483-4487; Yang et al. (2009) Clin. Cancer Res., 15:4722-4732). The excess of PMAO amphiphilic polymers was removed through ultracentrifugation (600,000 g for 45 minutes). 5 mg of the PMAO modified iron oxide nanoparticles was added to 20 mL of 10 mg/mL PDDA aqueous solution in 20 mM Tris buffer. The PDDA was allowed to absorb for 20 min under stirring. The formed nanoparticles were purified by the method described above and used for further studies.

Ethidium Bromide Dye Displacement Assay

Fluorescence titration of siRNA/EtBr with the complexation agents were performed as described above for Example 2. Binding of the complexation agents such as the mixtures of SPIO nanoparticles with PPI G5 dendrimer caused a displacement of bound EtBr, resulting in a decrease in the fluorescence emission intensity.

Preparation of SPIO-PPI G5-siRNA Complexes

Prior to the cooperative complexations of siRNA with SPIO nanoparticles and PPI G5, the stock solutions of the mixtures were prepared by adding PPI G5 dendrimer to SPIO nanoparticle solutions with the ratio of primary to the quaternary amines equal 5:1. The complexes of siRNA with mixture of SPIO and PPI G5 dendrimer were prepared at amine/phosphate ratio (N/P ratio) equal to 0.73. Briefly, siRNA solution was mixed with HEPES buffer (5 mM, pH 7.2) and an appropriate amount of the complexation agents was added. For in vitro studies, the final concentration of siRNA in the solution was 4.0 µM. For in vitro and in vivo studies the final concentrations of siRNA in the solutions were 60 µM and 30 µM, respectively. The samples were vortexed briefly, and the solutions were then incubated at room temperature for 30 minutes to ensure complex formation.

Modification of SPIO-PPI G5-siRNA Complexes with PEG and LHRH

In order to modify the SPIO-PPI G5-siRNA complexes, NHS-PEG-MAL was reacted with primary amines on the surfaces of the particles in 5 mM HEPES buffer (pH 7.2). The ratio of primary amines to PEG was 10:1. The reaction was carried out for 1 hour at room temperature. PEGylated SPIO-PPI G5-siRNA complexes were then mixed with LHRH peptide dissolved in a HEPES buffer and incubated overnight at 4° C. The ration of PEG-MAL:LHRH in the reaction mixture was 1:2. The resulting product was dialyzed against deionized water using a Spectra/Pore dialysis membrane with the molecular weight cutoff of 10,000 Da obtained from Spectrum Laboratories, Inc. (Rancho Dominguez, Calif.).

Degree of PEGylation

The percentage of amino groups available for PEGylation as well as the decrease in their concentration after the reaction was determined by modified TNBSA assay (Taratula et al. (2009) J. Controlled Release 140:284-293). Briefly, 180 µL solution of either non-modified or PEGylated SPIO-PPI G5-siRNA complexes was mixed with 4 µL of TNBSA solution (0.03M in water). Absorbance at 420 nm was measured after 30 minutes incubation at room temperature. All absorption measurements were performed using a Cary-500 fluorescence spectrophotometer (Varian, Inc, Palo Alto, Calif.). The final concentration of primary amines was calculated using standard curves. Standard curves were prepared by plotting the average blank corrected absorption at 420 nm reading for each standard vs. its concentration in µM.

Agarose Gel Retardation Assay

The agarose gel retardation assays were performed as described above for Example 2. Complexation of siRNA prevented staining of siRNA by EtBr and led to the disappearance of the siRNA band. Therefore, the fluorescent intensity of the 21 base pair band on the gel disappeared when siRNA was complexed with SPIO nanoparticles and dendrimers.

Evaluation of LHRH Peptide Reaction with SPIO-PPI G5-siRNA Complexes

Determination of the presence of LHRH peptide on the surface of SPIO-PPI G5-siRNA complexes was performed using Bicinchoninic Acid (BCA) protein assay (Pierce, Rockford, Ill.). The BCA method employs the reduction of $Cu^{+2}$ to $Cu^{+1}$ by protein in an alkaline medium. The combination of Bicinchoninic acid and $Cu^{+1}$ creates a purple-colored product that absorbs at 562 nm. The amount of product formed is dependent upon the amount of protein in the sample. The spectra of the product corresponding to free LHRH and SPIO-PPI G5-siRNA-PEG-LHRH complexes have well defined absorbance maximum around 560 nm corresponding to the absorbance of the BCA/copper complex. These complexes are formed as a result of the reaction of BCA reagent with the cuprous cation produced from the reduction of $Cu^{+2}$ to $Cu_{+1}$ by the LHRH peptide (Taratula et al. (2009) J. Controlled Release 140:284-293; Patil et al. (2009) Biomacromolecules 10:258-266). The absorbance maximum was absent in the assay spectra of the non-targeted complexes that are not modified with LHRH. Briefly, 20 µL of the test solution was mixed with 200 µL of working reagent and left to react for 30 minutes at 37° C. The solution then was incubated at room temperature for 10 minutes and the absorbance was measured at 562 nm.

Dynamic Light Scattering

Dynamic Light Scattering (DLS) studies were performed as described above in Example 2.

Atomic Force Microscopy

In order to obtain Atomic Force Microscope (AFM) images of formulated complexes, 5 µl aliquots of SPIO-PPI G5-siRNA solutions were deposited on a freshly cleaved mica surface. After 5 minutes of incubation, the surface was rinsed with several drops of nanopure water (Barnstead), and dried under a flow of dry nitrogen. AFM images were obtained using Nanoscope IIIA AFM (Digital Instruments, Santa Barbara, Calif.) in a tapping mode, operating in ambient air. A 125 µm long rectangular silicon cantilever/tip assembly was used with a spring constant of 40 Nm-1, resonance frequency of 315-352 kHz, and tip radius of 5-10 nm. The applied frequency was set on the lower side of the resonance frequency. The image was generated by a change in amplitude of the free oscillation of the cantilever as it interacted with the sample. The height differences on the surface are indicated by the color code, lighter regions indicating an increase in the height of the complexes. The height and outer diameter of formulated complexes were measured using the Nanoscope software.

Cell Lines

Two cancer cell lines with a different level of expression of LHRH receptors were used. Human LHRH positive A549 lung carcinoma cells and SKOV-3 LHRH negative ovarian cancer cells were obtained from the ATTC (Manassas, Va., USA). In addition, A549 human lung adenocarcinoma epithelial cell line transfected with luciferase was purchased from Xenogen Bioscience, (Cranbury, N.J.). Cells were cultured in RPMI 1640 medium (Sigma Chemical Co., Louis, Mo.) supplemented with 10% fetal bovine serum (Fisher Chemicals, Fairlawn, N.J.). Cells were grown at 37° C. in a humidified atmosphere of 5% $CO_2$ (v/v) in air. All of the experiments were performed on the cells in exponential growth phase.

Cellular Internalization of siRNA

Cellular internalization of FAM-labeled siRNA complexes were analyzed by fluorescence (Olympus America Inc., Melville, N.Y.) and confocal (Leica Microsystems Inc., Bannockburn, Ill.) microscopes as previously described (Patil et al. (2009) Biomacromolecules 10:258-266; Taratula et al. (2009) J. Controlled Release 140:284-293; Garbuzenko et al. (2009) Pharm. Res., 26:382-394). To assess cellular internalization and localization of siRNA, ten optical sections, known as a z-series, were scanned sequentially by a confocal microscope along the vertical (z) axis from the top to the bottom of the cell. Prior to the visualization, A549 and SKOV-3 cells were plated (20,000 cells/well) in 6-well tissue culture plate. The cells were treated with different formulations for 24 hours. The concentration of siRNA was 0.25 µM. After 24 hours of treatment cells were washed three times with phosphate buffered saline (PBS) and 1 mL of fresh medium was added to each well.

In Vitro Cytotoxicity

The cellular cytotoxicity of the formulated siRNA complexes was assessed as described above for Example 2. Briefly, A549 cells were separately incubated in 96-well plate with different concentrations of the studied formulations, which resulted in a total of seven separate series of experiments: (1) Control (fresh media); (2) Mixture of 5 nm SPIO nanoparticles and PPI G5 dendrimers; (3) 5 nm SPIO-PPI G5-siRNA complexes; (4) 5 nm SPIO-PPI G5-siRNA-PEG-LHRH complexes; (5) CIS; (6) Mixture of CIS and 5 nm SPIO-PPI G5-siRNA complexes and (7) Mixture of CIS and 5 nm SPIO-PPI G5-siRNA-PEG-LHRH complexes.

Gene Expression

Quantitative reverse transcription-polymerase chain reaction (RT-PCR) was performed as described above in Example 2.

In Vivo Study

NCR nude mice (female, 6 weeks, 20 g) were purchased from Taconic Farms, Inc. (Germantown, N.Y.). An animal model of human cancer xenografts was used (Taratula et al. (2009) J. Controlled Release 140:284-293; Chandna et al. (2007) Mol. Pharm., 4:668-678; Saad et al. (2008) J. Control Release 130:107-114). Briefly, A549 human cancer cells transfected with luciferase ($5 \times 10^6$) were subcutaneously transplanted into the flanks of female athymic nu/nu mice. According to the approved institutional animal use protocol, the tumors were measured by a caliper every other day and their volumes were calculated as $d^2 \times D/2$ where d and D are the shortest and longest diameter of the tumor in mm, respectively. When the tumor reached a mean size of 50 mm$^3$, mice were divided into seven groups and injected intratumorally 3 times within 10 days with 150 μL of the following formulations: (1) saline (control); (2) free non-bound LHRH; (3) free non-bound siRNA; (4) free non-bound CIS; (5) Mixture of CIS and SPIO-PPI G5; (6) Mixture of CIS and SPIO-PPI G5-siRNA; and (7) Mixture of CIS and SPIO-PPI G5-siRNA-PEG-LHRH complexes. The concentrations of CIS and siRNA in the formulations were 2.5 mg/kg and 30 μM, respectively. Changes in tumor size were monitored by real-time bioluminescence in anesthetized animals by IVIS imaging system (Xenogen Bioscience, Cranbury, N.J.).

Statistical Analysis

Data were analyzed as described hereinabove for Example 2. Ten animals were used in each group of in vivo experiments.

Results siRNA complexes were prepared with a mixture of SPIO nanoparticles and PPI G5 dendrimers, which introduced functional primary amino groups on the surfaces of formulated siRNA complexes for their further modification (FIG. 24). PPI dendrimers were covered with PEG polymers and LHRH peptide as a targeting moiety specific to cancer cells was conjugated to the distal end of the polymer. The efficiency of 5 nm and 10 nm SPIO nanoparticles to cooperatively provoke siRNA complexation with PPI G5 was studied by ethidium bromide dye displacement assay. The ratio of free amines (nitrogen) on PPI dendrimers and SPIO nanoparticles to phosphate on the siRNA (N/P ratio) was employed to quantify the efficacy of cooperative siRNA condensation. Quantitative analysis of the mixture's complexation efficiency reveals that the mixture of 5 nm SPIO and PPI G5 is more effective in provoking siRNA complexation (the apparent end point of complexation of N/P ratio=0.73) than PPI G5 dendrimer alone (N/P ratio=1.13) and 10 nm SPIO with PPI G5 (N/P ratio=1.3) (FIG. 25A, end points of complexation are denoted as circles in the insert). Therefore, the mixture of 5 nm SPIO and PPI G5 was the most effective complexation agent and was employed for the development of multifunctional nanomedicine platform for cancer specific delivery of siRNA. Agarose gel retardation assay was additionally involved to confirm the formation of 5 nm SPIO-PPI G5-siRNA complexes formed at N/P ratios which represented the apparent complexation end points obtained from ethidium bromide dye displacement assay. It was found that a complete binding of siRNA (without the presence of a trailing band) with the mixtures of 5 nm SPIO and PPI G5 dendrimers was observed in comparison to free siRNA (FIG. 25B).

DLS measurements at a 108° scattering angle were used to estimate the apparent hydrodynamic diameters of the resulting siRNA complexes. The results of DLS measurements demonstrate that the average diameter of 5 nm SPIO-PPI G5-siRNA complexes was 169.8±28.4 nm (FIG. 26A). In addition to DLS measurement, the formation of nanosized siRNA complexes has further been confirmed by AFM (FIG. 26B). AFM analysis verified that 5 nm SPIO nanoparticles cooperatively with PPI G5 dendrimers could effectively produce complexes with siRNA leading to the formation of discrete particles with an average diameter of 214.3±53.1 nm. The differences in the size of nanoparticles probably reflect the differences in a sample preparation for the size measurements by two different methods. DLS was performed on nanoparticles in a fully hydrated state in solution, whereas AFM studies were carried out on samples dried to the mica surface, which resulted in flattering of the nanoparticles on the mica surface during the drying process (Wang et al. (2008) Clin. Cancer Res., 14:3607-3616).

The PEGylation of SPIO-PPI G5-siRNA complexes was carried out by coupling of linear MAL-PEG-NHS to the amino groups on the surface of the complexes, which were introduced by PPI G5 dendrimers. The availability of the primary amines in the structure of the prepared siRNA complexes before PEGylation as well as the decrease in their concentration after PEGylation has been estimated by the TNBSA assay. The result reveals that the degree of PEGylation was 70% for SPIO-PPI G5-siRNA complexes.

To examine the influence of nanoparticles coating on their cellular uptake, PEGylated and non-PEGylated siRNA complexes were incubated with A549 cancer cells in a fresh medium. Fluorescence microscopy studies revealed the fact that PEG modification of SPIO-PPI G5-siRNA complexes enhance their sterical stability and prevent the aggregation of complexes that was abundant in non-PEGylated complexes (FIG. 27, compare panels A and B). On the other hand, non-PEGylated complexes provided for an effective delivery of labeled siRNA into the cells (FIG. 27A). As expected, PEGylation of the siRNA complexes decreased their internalization by cancer cells.

In order to evaluate the biological activity of the delivered siRNA, the siRNA targeted to BCL2 mRNA was used in the present study. FIG. 28 shows the expression of the BCL2 gene in A549 and SKOV-3 human cancer cells treated with siRNA delivered by different SPIO-PPI G5 complexes. The suppression of BCL2 mRNA by the PEGylated complexes was substantially lower when compared with the corresponding non-PEGylated system (lines 2 and 3). The sufficient decrease in gene silencing activity of the PEGylated complexes corroborate with cellular internalization data. To exclude nonspecific effects on gene expression by SPIO-PPI G5 complexes alone without bound siRNA, whether the mixtures of SPIO nanoparticles with dendrimers could impact the BCL2 gene expression was examined. RT-PCR analysis demonstrated that the employed siRNA delivery systems did not induce statistically significant changes in the expression of BCL2 mRNA in A549 cancer cells at the studied concentrations (FIG. 28, line 5). Similarly, a mocked siRNA duplex with a scrambled sequence having no significant homology to any known gene sequences was used in this series of the experiments as a negative control. RT-PCR data demonstrated that complexes with such mocked siRNA did not show any statistically significant inhibition of BCL2 mRNA expression confirming the specificity of BCL2 mRNA functional knockdown (FIG. 28, line 6).

In order to conjugate a targeting moiety (LHRH decapeptide) to the siRNA nanoparticles, the maleimide group at the distal end of the PEG-chain was coupled to thiol group presented by cysteine residue in modified LHRH sequence. The presence of LHRH peptide on the complex surface was confirmed by Bicinchoninic Acid (BCA) protein assay (Thermo Fisher Scientific Inc., Rockford, Ill.) according to manufacture protocol. As shown in FIG. 26A, DLS measurements reveal that the diameter of modified SPIO-PPI G5-siRNA complexes was 212.0±35.6 nm, respectively. The increase in the size of the modified siRNA complexes compared to non-modified ones could be explained by the presence of the polymer layer on the surface of siRNA complexes.

In vitro studies were performed to characterize the influence of LHRH peptide as a targeting moiety on the uptake and intracellular activity of the entrapped siRNA. The fluorescence microscopy images demonstrated a sufficient increase in the intracellular internalization of LHRH-targeted complexes by A549 cancer cells which overexpress LHRH receptors (FIG. 27C, D). In contrast, cellular uptake of tumor-targeted siRNA complex in LHRH negative SKOV-3 cells was substantially less when compared with non-targeted complexes (FIG. 27D). These experiments confirmed that the targeted shielded nanoparticles indeed delivered the siRNA specifically to the cancer cells, which overexpress the targeting receptors.

Theoretically, the formulated siRNA complexes could adhere to the surface of LHRH-positive cancer cells and erroneously be visualized on microscopic images as internalized within the cell. To exclude such errors, the distribution of LHRH targeted siRNA complexes was analyzed in different cellular layers from the upper to the lower surfaces of the cell using confocal fluorescent microscopy. In these experiments, the formulated complexes with FAM labeled siRNA were incubated with human A549 cancer cells. The cells were subjected to confocal microscopy. The z-section of single cells transfected with the modified complexes, formed by complexation of siRNA with the mixture of SPIO nanoparticles and PPI G5 dendrimer, and showed their homogeneous and uniform distribution in all layers of the cell from the top surface to the bottom (FIG. 29). To assess the ability of LHRH targeted complexes not only to deliver siRNA but knockdown targeted gene expression, complexes with BCL2-specific siRNA were prepared. In this series of the experiments, both LHRH positive (A549) and negative (SKOV-3) cancer cells were treated with the prepared siRNA complexes for 24 hours. The RT-PCR data obtained revealed that the LHRH modification of siRNA complexes restore the knockdown activity for siRNA complexes, which was decreased after PEGylation (FIG. 28, line 4). On the hand, the silencing effect of the BCL2-targeted siRNA was not significant in LHRH-negative cancer cells (FIG. 28, line 7), which is in good agreement with the siRNA cellular internalization result represented in FIG. 27. Therefore, as expected, LHRH peptide proved its capability to target effectively the siRNA complexes to the specific receptors in the plasma membrane of cancer cells.

The influence of the formulated siRNA delivery systems on cell viability was investigated in A549 human lung cancer cell line by the MTT assay. FIG. 30A shows the average data from three different experiments with increasing concentration of the complexes. One can see that over 95% average cell viability was observed for both 5 nm SPIO-PPI G5 and 5 nm SPIO-PPI G5-siRNA delivery systems at the concentrations used for in vitro and in vivo experiments of the present study. At a maximum available concentration, the mean cell viabilities for the targeted SPIO-PPI G5-PEG-LHRH complex was 85% compared with that of the control, respectively.

The ability of the developed siRNA delivery system to enhance efficiency of a chemotherapeutic drug such as CIS was evaluated in the current study both in vitro and in vivo. The cellular cytotoxicity of Cisplatin alone and in combination with non-targeted SPIO-PPI G5-siRNA or targeted SPIO-PPI G5-siRNA-PEG-LHRH delivery systems was assessed using a modified MTT assay. Data in FIG. 30B shows that cytotoxicity of CIS against multidrug resistant human cancer cells was sufficiently enhanced in the presence of non-targeted or LHRH targeted siRNA delivery vectors. The maximum enhancement of anticancer activity of CIS was observed at the lower concentration range of the drug (1 µg/mL-150 µg/mL).

Antitumor activities of the proposed formulations with corresponding controls were studied in vivo using subcutaneous xenograft model of human cancer. The progression of tumor growth was monitored by an IVIS imaging system and by measuring the tumor volume (FIG. 31, upper and bottom panels, respectively). It was found that free LHRH and non-conjugated naked siRNA did not significantly influence the growth of the tumor (FIG. 31, bottom panel, curves 2-3). Free CIS limited the growth of the tumor at the last day of the treatment on 36.2% when compared with untreated control (FIG. 31, image 4, curve 4). Simultaneous delivery of CIS and SPIO-PPI-G5 dendrimer complex slightly increased the antitumor activity of the drug (FIG. 31, image 5, curve 5). The suppression of cellular antiapoptotic defense by siRNA targeted to BCL2 mRNA, delivered by SPIO-PPI G5-siRNA complex simultaneously with CIS significantly enhanced the antitumor activity of the drug. In fact, the tumor volume decreased on 67.5% after the combinatorial treatment when compared with untreated control (FIG. 31, image 6, curve 6). Targeting of siRNA complexes specifically to the tumor by LHRH peptide led to the further enhancement of the antitumor activity of CIS. The tumor volume decreased on 75.5% when compared with untreated control (FIG. 31, image 7, curve 7).

Multifunctional nonviral vector have been for siRNA delivery based on SPIO nanoparticles modified with PDDA and PMAO, which contain quaternary ammonium and carboxylic functional groups on the periphery for siRNA condensation and endosomal release. These SPIO nanoparticles demonstrated high efficiency to form complexes with siRNA and to facilitate their internalization by the cancer cells. Cellular uptake of such SPIO-siRNA complexes most probably occurred by adsorptive-mediated endocytosis, which is triggered by electrostatic interactions between the negatively charged plasma membrane and the positively charged complexes. Targeting of the SPIO-siRNA complexes specifically to cancer cells by incorporating a ligand to the receptors overexpressed in the plasma membrane of cancer cells can offer at least three advantages. First, it switches the mechanism of cellular internalization toward more efficient receptor-mediated endocytosis. Second, specific targeting to cancer cells prevents rapid clearance of the siRNA cationic complexes by liver, spleen, and kidney after systemic administration (Taratula et al. (2009) J. Controlled Release 140:284-293; Fischer et al. (2004) Drug Metab. Disposit., 32:983-992). Third, the delivery of therapeutic payload specifically to cancer cells limits adverse side effects of the treatment on healthy organs by changing its organ distribution toward the preferential accumulation in the tumors (Taratula et al. (2009) J. Controlled Release 140:284-293; Chandna et al. (2007) Mol. Pharm., 4:668-678; Dharap et al. (2005) Proc. Natl. Acad. Sci., 102:12962-12967). Consequently, in the present study, tumor-targeted superparamagnetic iron oxide nanoparticles-dendrimer complexes have been characterized for simultaneous delivery specifically to tumor cells of siRNA and MRI-contrast agents. Therefore, the proposed complex multifunctional drug delivery platform can be used for simultaneous suppression of cellular resistance by siRNA and MRI imaging of the system itself, and primary tumor or metastases. Experimental data show the following advantages of the proposed delivery system.

It is well-known that siRNA complexes should have an optimal size and proper shape for effective gene delivery because that often governs the transfection efficiency, cytotoxicity, and tissue targeting of an entire system in vivo (Fischer et al. (2004) Drug Metab. Disposit., 32:983-992). Generally, in order to enable its effective penetration into tissue, the size of gene delivery vehicles should not exceed 250 nm (Wood et al. (2005) Angewandte Chemie-Intl. Ed., 44:6704-6708), although the optimal size of the particles is still under debate. Direct measurements by several independent approaches determined that the size of complexes developed in the present study was approximately 200 nm (with complexated siRNA). The nanoparticles were compact and close to spherical shape. Consequently, one could expect that such dendrimer-based systems will provide for an efficient delivery of its payload into cancer cells (Patil et al. (2009) Biomacromolecules 10:258-266; Taratula et al. (2009) J. Controlled Release 140:284-293; Patil et al. (2008) Bioconjugate Chem., 19:1396-1403). Further investigations confirmed this suggestion.

Cytotoxicity of gene transfection vectors including viral vectors, inorganic nanoparticles, cationic liposomes, and polymeric cations is a major barrier for their efficient use for the delivery of therapeutic genes (Bessis et al. (2004) Gene Ther., 11:S10-S17). Recently, it has been demonstrated that PPI dendrimers can intrinsically alter the expression of many endogenous genes, the nature and extent of which were dependent on the dendrimer generation, and cell type (Omidi et al. (2005) J. Drug Targeting 13:431-443). Although cytotoxicity of a nanocarrier itself is not an issue for the delivery of anticancer drugs with much more higher cytotoxicity, it was found that the proposed targeted and nontargeted SPIO-PPI G5 vehicles alone and in combination with siRNA possessed low cytotoxicity. Moreover, a mixture of SPIO with PPI G5 dendrimers alone without siRNA did not influence the expression of the targeted BCL2 gene. Such low toxicity of the modified siRNA complexes makes them attractive for in vivo delivery of nontoxic compounds. Consequently, similar drug delivery systems can be used for applications other than cancer chemotherapy.

It is known that siRNA complexes are usually easily opsonized and removed from the circulation long prior to completion of their main function (de Wolf et al. (2007) Intl. J. Pharm., 331:167-175; Dash et al. (1999) Gene Ther., 6:643-650). Chemical modification of siRNA delivery vector with certain synthetic polymers, such as PEG, is the most frequent way to increase the in vivo longevity in the systemic circulation of siRNA delivery vectors. The layer of hydrophilic polymer (in most cases PEG) sterically hinders interactions of blood components with the positively charged surface of siRNA complexes and enhances their stability in the blood stream (Schiffelers et al. (2004) Nuc. Acids Res., 32:e149; Mao et al. (2006) Bioconjugate Chem., 17:1209-1218). However, simultaneously while improving the pharmacokinetics, PEGylation usually limits cellular internalization in vivo (stealth effect) (Taratula et al. (2009) J. Controlled Release 140:284-293). It is known that neutral surface charge of PEGylated siRNA complexes limits their interactions with a negatively charged cell membrane when compared with positively charged non-modified siRNA complexes. To overcome these obstacles, the modification of sterically stabilized siRNA delivery carriers with cell targeting ligands is usually used in order to enhance its transfection activity. The different targeting moieties including, galactose, folate, RGD-peptide and antibodies were examined for the delivery of DNA and siRNA. Recently, it was found that the receptor for LHRH is overexpressed in many types of human cancer cells and was not detectably expressed in healthy human visceral organs (Dharap et al. (2003) Pharm. Res., 20:889-896; Dharap et al. (2003) J. Controlled Release 91:61-73). Furthermore, it has been shown that the use of the LHRH peptide for the targeting of a polymeric anticancer drug delivery system to cancer cells substantially limits its adverse side effects on healthy tissues and significantly enhances the antitumor efficacy of the anticancer drug. Therefore, based on these results the synthetic analog of LHRH peptide was selected as a targeting moiety to enhance the internalization of the developed siRNA delivery system specifically by cancer cells. The results of the in vitro and in vivo experiments of this tumor-targeted system showed that an incorporation of LHRH peptide substantially improved cellular internalization of siRNA, increased its transfection efficiency, and enhanced the antitumor activity of drug.

The data clearly show that the combinatorial delivery of siRNA with anticancer drug substantially enhanced the efficiency of chemotherapy leading to the more significant limitation of the tumor growth. Therefore, it is important to deliver siRNA inside tumor cells simultaneously with an anticancer drug. The delivery of siRNA requires an appropriate carrier because naked siRNA is unstable in the blood stream and poorly penetrates cells. The proposed in the present research delivery system significantly improves the stability of siRNA in plasma and provides for its efficient cellular internalization. In addition, an incorporation of a tumor-targeting moiety (LHRH peptide) into the DDS permits the delivery of siRNA specifically into tumor cells further enhancing antitumor effects of the drug and limiting adverse side effects of the treatment on healthy organs.

In summary, the designed siRNA delivery vector based on SPIO nanoparticles modified with PPI G5 dendrimers and PEG combines the cell-targeted selectivity with the specificity of siRNA. The modular chemical design of the proposed system allows for the substitution of used cancer targeting moiety with other ligands, or combinations of ligands, to selectively target other type of cancer cells.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A composition comprising at least one liposome or dendrimer comprising at least two chemotherapeutic agents with different mechanisms of action and at least two inhibitors of cellular drug resistance, and at least one pharmaceutically acceptable carrier, wherein said inhibitors of cellular drug resistance are an antisense molecule or an siRNA molecule, wherein said inhibitors of cellular drug resistance include an inhibitor of pump resistance and an inhibitor of nonpump resistance, wherein said inhibitor of nonpump resistance is an inhibitor of BCL2, wherein said inhibitor of pump resistance is an inhibitor of multidrug resistance protein (MRP) or P-glycoprotein encoded by the multidrug resistance 1 (MDR1), and wherein said liposome or dendrimer further comprises at least one cancer targeting ligand.

2. The composition of claim 1, wherein said chemotherapeutic agents are selected from the group consisting of doxorubicin, paclitaxel, and cisplatin.

3. The composition of claim 1, wherein said cancer targeting ligand is luteinizing hormone-releasing hormone (LHRH) or an analog thereof.

4. The composition of claim 3, wherein the LHRH analog is SEQ ID NO: 3.

* * * * *

UNITED STATES PATENT AND TRADEMARK OFFICE
CERTIFICATE OF CORRECTION

PATENT NO. : 9,289,505 B2
APPLICATION NO. : 13/817054
DATED : March 22, 2016
INVENTOR(S) : Tamara Minko et al.

It is certified that error appears in the above-identified patent and that said Letters Patent is hereby corrected as shown below:

In the Specification

At Column 1, Lines 15-18, please delete the paragraph:
"This invention was made with government support under grant Nos. CA138533, CA111766, and CA100098 awarded by the National Institutes of Health, National Cancer Institute. The government has rights in the invention."

And insert therefor:
--This invention was made with government support under grant numbers CA100098, CA111766 and CA138533 awarded by the National Institutes of Health. The government has certain rights in the invention.--

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*